(12) United States Patent
Matsumura et al.

(10) Patent No.: US 8,141,520 B2
(45) Date of Patent: Mar. 27, 2012

(54) LIVESTOCK STERILIZING METHOD, LIVESTOCK STERILIZING APPARATUS, AND LIVESTOCK OR LIVESTOCK MEAT

(76) Inventors: Eiji Matsumura, Kawasaki (JP); Nobuko Hagiwara, Chuo-Ku (JP)

( * ) Notice: Subject to any disclaimer, the term of this patent is extended or adjusted under 35 U.S.C. 154(b) by 980 days.

(21) Appl. No.: 11/816,197

(22) PCT Filed: Feb. 21, 2006

(86) PCT No.: PCT/JP2006/303085
§ 371 (c)(1), (2), (4) Date: Aug. 14, 2007

(87) PCT Pub. No.: WO2006/088210
PCT Pub. Date: Aug. 24, 2006

(65) Prior Publication Data
US 2010/0186680 A1    Jul. 29, 2010

(30) Foreign Application Priority Data

| Feb. 21, 2005 | (JP) | 2005-044867 |
| May 23, 2005 | (JP) | 2005-150180 |
| Jun. 6, 2005 | (JP) | 2005-164937 |
| Oct. 24, 2005 | (JP) | 2005-308726 |
| Nov. 23, 2005 | (JP) | 2005-337916 |

(51) Int. Cl.
*A01K 29/00* (2006.01)

(52) U.S. Cl. ......... 119/651; 119/650; 119/665; 119/667

(58) Field of Classification Search ................. 119/650, 119/651, 665, 667
See application file for complete search history.

(56) References Cited

U.S. PATENT DOCUMENTS

| 3,699,928 A * | 10/1972 | Cowan .......................... 119/667 |
| 3,949,709 A * | 4/1976 | Myers .......................... 119/667 |
| 4,176,061 A * | 11/1979 | Stopka .......................... 210/760 |
| 4,549,502 A * | 10/1985 | Namdari ....................... 119/664 |

(Continued)

FOREIGN PATENT DOCUMENTS

JP    3069986 U    4/2000

(Continued)

OTHER PUBLICATIONS

Masayoshi Takahashi, "Micro Bubble o Riyo Shita Kankyo Joka to Shoku no Anzen Kakuho," Bulletin of the Society of Sea Water Science, Japan, Feb. 1, 2005, vol. 59, No. 1, pp. 17-22.

*Primary Examiner* — Joshua J Michener
*Assistant Examiner* — Justin Benedik
(74) *Attorney, Agent, or Firm* — Burr & Brown

(57) ABSTRACT

By effectively inhibiting ozone escape from ozonized water, a livestock sterilizing method which does not have the possibility of having an adverse effect on man and livestock is provided. Sterilizing of livestock is performed by including an ozonized water producing step of producing ozonized water with a particle size R of a contained ozone bubble satisfying 0<R<50 nm and an ozone concentration of 3 ppm to 20 ppm by a gas-liquid mixing method, and a step of sterilizing livestock by using the ozonized water produced in the ozonized water producing step. Since the particle size R is 0<R<50 nm, the ozone bubbles hardly receive buoyancy of the ozonized water. Therefore, the ozone bubbles do not rise to the water level, but stay in the ozonized water. As a result, ozone escape is effectively inhibited.

57 Claims, 30 Drawing Sheets

U.S. PATENT DOCUMENTS

| | | | |
|---|---|---|---|
| 5,130,032 A * | 7/1992 | Sartori | 210/748.04 |
| 5,186,841 A * | 2/1993 | Schick | 210/760 |
| 5,709,799 A * | 1/1998 | Engelhard | 210/748.1 |
| 6,029,610 A * | 2/2000 | Ramsey et al. | 119/651 |
| 6,520,118 B2 * | 2/2003 | Swiegers et al. | 119/666 |
| 7,255,332 B2 * | 8/2007 | Osborn et al. | 261/28 |
| 2001/0010208 A1 * | 8/2001 | Greeson | 119/665 |
| 2003/0024485 A1 * | 2/2003 | Freidell | 119/665 |
| 2005/0005872 A1 * | 1/2005 | Greeson | 119/665 |

FOREIGN PATENT DOCUMENTS

| | | |
|---|---|---|
| JP | 2002-020211 A1 | 1/2002 |
| JP | 2002-306086 A1 | 10/2002 |
| JP | 2003-175324 A1 | 6/2003 |

* cited by examiner

LIVESTOCK STERILIZING METHOD, LIVESTOCK STERILIZING APPARATUS, AND LIVESTOCK OR LIVESTOCK MEAT

FIELD OF THE INVENTION

The invention relates to a livestock sterilizing method, a livestock sterilizing apparatus, and livestock or livestock meat.

BACKGROUND OF THE INVENTION

What becomes a problem in raising livestock (poultry) is foul odors from livestock and livestock barns, and diseases of the livestock. Most of these foul odors and diseases are brought about by pathogenic bacteria and viruses (hereinafter, properly referred to as "viruses and the like" generically) which are parasitic on excrement and residual food of livestock. Such a foul odor is a serious environmental problem, and the diseases may often become the causes of death and incomplete development of livestock. In fact, death of livestock greatly affects livestock raisers. For example, the death rate of pigs in the pig raising industry sometimes reaches several percent to 20% when it is high. Occurrence of Salmonellosis, Aujeszky disease, PRRS, mycoplasma Pocine Epidemic Diarrhea (PED), Transmissible Gastoenteritis (TGE) and the like tends to increase. In the poultry industry, the news that avian influenza prevailed and a large number of chickens were killed and disposed of is still fresh in our memory. In order to prevent such an event, it is essential to sterilize (disinfect) livestock and the livestock barns to sterilize or inactivate pathogenic bacteria and viruses.

As a method for sterilizing or inactivating such pathogenic bacteria and viruses, Patent Document 1 discloses the method for spraying ozonized water. The ozone concentration of the ozonized water disclosed in the Patent Document 1 is set at 0.05 to 0.10 ppm. However, according to the former Ministry of Health, Labor and Welfare Hygienic Control Laboratory Data (Non-patent Document 1, refer to Table 1), the ozone concentration required for exterminating main microorganisms is about 1 ppm. Accordingly, even if the ozonized water with the ozone concentration being in the above described range is sprayed, a doubt as to its sterilizing effect remains. According to the experiment conducted by Mie Prefectural Science and Technology Promotion Center, Agricultural Technology Center, (Livestock) Small and Medium Livestock Group, it was reported that sprayed ozonized water had no effect of sterilizing Salmonella, more specifically, Salmonella was not able to be sterilized in five minutes after spraying the ozonized water of 1 ppm and 4 ppm (refer to Non-patent Document 2). It is supposed that ozone escaped by spraying. On the other hand, Patent Document 2 discloses the art of spraying ozonized water for disease control. According to the Patent Document 2, the disclosed disease control method is for plants growing in greenhouses, and it poses a question about low-concentration ozonized water similarly as in the above description. Specifically, it finds a question as to practicality in controlling diseases and pest with low-concentration ozonized water, and in the above described disease control method, the ozonized water with an ozone concentration of 2 to 20 ppm is used. Patent Document 2 also describes that on the occasion of spraying high-concentration ozonized water, it is preferable that workers do not enter the greenhouse in which the ozonized water is sprayed. Patent Document 2 does not include the reason why it is preferable, but it is supposed that the case where gas-liquid separation occurs by spraying high-concentration ozonized water, and the ozone generated by the separation increases the ozone concentration in the greenhouse to have an adverse effect on the workers is conceivable, and therefore, Patent Document 2 takes such a case into consideration. In addition to these documents, Patent Document 3 discloses the art of washing horses by producing ozonized water of 2 ppm at the maximum and spraying it.

[Patent Document 1] Japanese Patent Application Laid-open No. 2002-306086 (paragraphs 0012 to 0016)

[Patent Document 2] Japanese Patent Application Laid-open No. 2002-20211 (paragraphs 0006, 0046)

[Patent Document 3] Registered Japanese Utility Model No. 3069986 (paragraphs 0012, 0013, 0016, 0017, FIG. 1)

[Non-patent Document 1] Former Ministry of Health, Labor and Welfare, Hygienic Control Laboratory Data (http://www.gendaikobo.co.jp/ecogoods/ecogoods01/eogoods01_1.htmL)

[Non-patent Document 2] Title of the Subject of the Study: "Establishment of Salmonella Contamination Prevention Technique for Securing Safety of Poultry Meat/Egg of Local Specialty" (http://www.affrc.go.jp/ja/db/seika/data_kan-tou/h12/narc00K240.html)

TABLE 1

| | EFFECT OF INACTIVATING MICROORGANISMS BY OZONIZED WATER | | | | | |
|---|---|---|---|---|---|---|
| KIND OF MICROORGANISM | UNDERWATER OZONE CONCENTRATION (ppm) | MICROORGANISM CONCENTRATION (NUMBER/ml) | TEMPERATURE (° C.) | Ph* | CONTACT TIME | DEATH RATE (%) |
| COLON *BACILLUS* | 0.96 | $10^5$ cells | 21 | 7 | 5 SECONDS | 100 |
| *STAPHYLOCOCCUS* | 1.08 | $10^5$ cells | 21 | 7 | 5 SECONDS | 100 |
| *BACILLUS* OF GREEN PUS | 1.01 | $10^5$ cells | 21 | 7 | 5 SECONDS | 100 |
| *CLOSTRIDIUM PERFRINGENS* | 0.96 | $10^5$ cells | 21 | 7 | 5 SECONDS | 100 |
| INFLUENZA VIRUS | 0.96 | $10^{33}$ TCID50 | 21 | 7 | 5 SECONDS | 100 |
| CANINE INFECTIOUS HEPATITIS VIRUS | 1.2 | $10^{15}$ TCID50 | 21 | 7 | 5 SECONDS | 100 |
| CANINE PARVOVIRUS | 0.96 | $10^{25}$ TCID50 | 21 | 7 | 5 SECONDS | 100 |
| *AVIAN COCCIDIUM* | 1.92 | $3 \times 10^3$ cells | 20 | 7 | 5 SECONDS | 100 |
| MOLD | 0.3-0.5 | $10^6$ cells | 20 | 6.5 | 5 SECONDS | 99.9 |

TABLE 1-continued

EFFECT OF INACTIVATING MICROORGANISMS BY OZONIZED WATER

| KIND OF MICROORGANISM | UNDERWATER OZONE CONCENTRATION (ppm) | MICROORGANISM CONCENTRATION (NUMBER/ml) | TEMPERATURE (° C.) | Ph* | CONTACT TIME | DEATH RATE (%) |
|---|---|---|---|---|---|---|
| YEAST | 0.3-0.5 | $10^6$ cells | 20 | 6.5 | 19 SECONDS | 99.9 |
| *BACILLUS SUBTILIS* | 0.3-0.5 | $10^6$ cells | 20 | 6.5 | 90 SECONDS | 99.9 |

*Ph OF STERILE DISTILLED WATER USED FOR DILUTION TO PREDETERMINED MICROORGANISM CONCENTRATION
MINISTRY OF HEALTH, LABOR AND WELFARE, HYGIENIC CONTROL LABORATORY (PRESENT: NATIONAL INSTITUTE OF INFECTIOUS DISEASE) DATA

However, high-concentration ozonized water has been considered to be incapable of being used for livestock, though it is usable for plants growing in greenhouses. This is because ozone occurring by spraying ozonized water has an adverse effect on livestock. Workers have not been allowed to enter a livestock barn at the time of spraying ozonized water for the same reason. If ozonized water is to be sprayed, it has to be sprayed after livestock is moved to another place to make the livestock barn vacant (all in-all out method), and the workers go outside the livestock barn. However, for an effective use of the space, as much livestock as possible is raised in the livestock barn. Specifically, in most cases, there is no room in the space. It is actually impossible to move the livestock altogether to another place under such a situation. This is the reason why sterilizing of livestock and a livestock barn by ozonized water has not been performed. Further, it can be cited as the reason that sprayed (sprinkled) ozonized water has been believed to have no sterilizing effect as described in the aforementioned Non-patent Document 2.

On the other hand, the art disclosed in Patent Document 3 does not take any measure to ozonized water spraying while there is the technological common sense that Salmonella cannot be sterilized even if ozonized water of 1 ppm and 4 ppm is sprayed as described in the aforementioned Non-patent Document 2. Therefore, according to the art disclosed in Patent Document 3, the ozone concentration after being sprayed cannot be said to be sufficient even when the ozone concentration of the ozonized water at the time when it is produced is 2 ppm at the maximum. Even if the ozone concentration of 2 ppm can be secured after being sprayed, it is extremely difficult to sterilize viruses and the like in the livestock-raising site with the ozonized water of 2 ppm. According to the above described Non-patent Document 1, the ozone concentration required for exterminating main microorganisms is about 1 ppm. However, this result was obtained from the experiment conducted in the test room of the laboratory, and at least 3 ppm which is three times as much as 1 ppm is required in the livestock-raising site. Specifically, microorganisms, viruses or the like in concrete, are parasite on the organic matters such as the excrement of livestock, residual food and the like attached to the body surface of the livestock, and the organic matters also react with ozone. Organic matters float in the air around livestock as dust, and such floating organic matters also the target of reaction with ozone. Sprayed or sprinkled ozonized water reacts with these organic matters immediately when contacting them, and most of it disappears. Therefore, the fact is that the sterilizing effect of ozone does not reach the viruses and the like attached to the livestock bodies.

SUMMARY OF THE INVENTION

Problems to be Solved by the Invention

Safety of ozonized water to a human body has been proven in the medical field, for example, and ozonized water is actually used for hand washing sterilization in medical institutions, cleaning at the time of bleeding accompanying extraction of teeth and the like in dentistry, eye washing before operation in ophthalmology and the like. The inventor, who considered that ozonized water which ought to be safe cannot be unusable for sterilizing livestock and a livestock barn, conducted the earnest researches on ozonized water, and as a result, the inventor acquired the knowledge that the reason why ozonized water cannot be used for sterilizing livestock and a livestock barn is as follows: First, since the use amount of ozonized water for sterilizing livestock and the like is much larger as compared with the use amount of ozonized water in the above described medical institutions, the amount of ozone escaping (going out of) or decomposing from the ozonized water is large, and the problem is that the large amount of ozone is filled in the atmosphere. Second, ozone escape mainly occurs by pressure change when the ozonized water is released from the pressure-fed state on the occasion of being sprayed with a hose (sprayed by using a hose). Third, ozone escape is especially remarkable when occurring at the instant when the ozonized water is sprayed from a nozzle when the ozonized water is intended to be sprayed from the nozzle. A problem to be solved by the present invention is to provide a livestock sterilizing method and its sterilizing apparatus which have no possibility of having an adverse effect on a human being and livestock by effectively inhibiting ozone escape from ozonized water, and livestock or meat of the livestock raised by using such a sterilizing method.

Means for Solving the Problem

The inventor pursued the research based on the above acquired knowledge, and obtained by the experiments the knowledge that the dissolution degree of ozone needs to be enhanced for effective inhibition of ozone escape, ozonized water can be used for livestock and a livestock barn since ozone escape can be effectively suppressed or prevented if the dissolution degree is increased, and in the ozonized water showing the above described characteristic, the ozone concentration of 3 ppm or more can be stably obtained, and the concentration is not easily reduced by being sprayed. Specifically, ozone escape is mainly caused by ozone bubbles contained in ozonized water rising to the liquid level by buoyancy and breaking. According to the understanding of the inventor, the ozone bubbles with the particle sizes of 50 nm or more receive enough buoyancy to raise them in the ozonized water. Conversely, ozone bubbles with the particle sizes of less than 50 nm hardly receive buoyancy, and therefore, has little fear of ozone escape. Ozonized water containing ozone bubbles with the particle sizes of less than 50 nm had not been able to be produced before. The inventor and the others succeeded in making the particle sizes of the contained ozone bubbles less than 50 nm by the ozonized water producing method which will be described later. The present invention is made based on the knowledge acquired from the success. The details of the invention will be described in the later paragraphs. The definition or the like of the terms which is made in explaining the invention set forth in any claim shall be also applied to the invention set forth in the other claims in the possible range in its characteristic irrespective of the difference in invention category, sequence of the description and the like.

According to a first aspect of the present invention, a livestock sterilizing method is provided, characterized by including an ozonized water producing step of producing ozonized water with a particle size R of a contained ozone bubble satisfying 0 nm<R<50 nm and an ozone concentration of 3 ppm to 20 ppm by a gas-liquid mixing method, and a step of sterilizing livestock by using the ozonized water produced in the ozonized water producing step. Ozone dissolution is performed by the method called a gas-liquid mixing method which mixes ozone gas into raw water (water to be treated). An ozonized water producing method by an electrolytic method (electrolysis) needs to add an additive (electrolysis aid) such as sodium chloride, the additive is capable of having an adverse effect on livestock, and therefore, this method is not the subject of the invention of the present application. Here, the raw water means the water immediately before ozone is dissolved in it, and, for example, tap water, ground water (well water) and the like are preferable. Rain water, river water, lake water and the like are usable unless there is no special reason. For example, the mixture of the water obtained from different water sources such as mixture water of tap water and ground water is also included in the raw water. The pH value of the raw water is generally neutral, but differs depending on the districts, and depending on the water sources such as ground water, tap water, rain water, river water and lake water. The raw water which is out of neutrality and inclined to an acid side or an alkaline side exists. Here, "neutrality" refers to pH6.5 to 7.5 (Food Sanitation Act of Japan, Food Additive Standards, Notification No. 370 of the former Ministry of Health and Welfare (the present Ministry of Health, Labor and Welfare) December, 28, 1959).

According to the sterilizing method of the first aspect, the particle sizes of the contained ozone bubbles are less than 50 nm, and therefore, the ozone bubbles hardly receive buoyancy in the ozonized water. Therefore, the ozone bubbles do not rise to the liquid level, but stay in the ozonized water. Namely, the above described ozonized water is the ozonized water with an extremely high ozone dissolution degree. Therefore, even when the ozonized water is used (sprayed, sprinkled, coated, wetted, immersed and the like) for sterilizing livestock, little ozone escapes from the ozonized water by its use. Accordingly, an adverse effect on the respiratory organ and the like of the livestock which will occur if ozone escapes can be effectively eliminated. When the ozone dissolution degree is high, production of high-concentration ozonized water is easy. Further, the above described ozonized water is produced by the gas-liquid mixing method for producing ozonized water by mixing ozone into raw water, and therefore, it does not require an additive as in production by an electrolysis method. Like this, the ozonized water according to the present invention is the ozonized water with high safety in the respect of requiring no additive. The reason why the lower limit of the ozone concentration after spraying is set at 3 ppm is that the ozone concentration required in the site of raising livestock is 3 ppm as described in the Background of the Invention section above. The reason why the upper limit is set at 20 ppm is that about 20 ppm is the limit of ozonized water production by the gas-liquid mixing method, and the production efficiency extremely reduces after the ozone concentration exceeds 20 ppm. The ozone concentration can be measured by, for example, an ultraviolet ray absorption device or the like.

According to a second aspect of the present invention, the livestock sterilizing method according to the first aspect is provided, and is further characterized in that pH of the aforesaid ozonized water is 6.5 to 7.5.

According to the sterilizing method of the second aspect, the sterilization of the first aspect can be made safer. Specifically, as shown by the experiment which will be described later, the ozonized water according to the present invention does not change pH of the raw water, and therefore, shows substantially neutrality. As it is known that ozone easily dissolves in neutral ozonized water, according to the ozonized water relating to the present invention, the ozonized water can be kept neutral without adjusting pH by adding an additive such as acetic acid. The ozonized water is high in safety for livestock in the respect of requiring addition of no additive.

According to a third aspect of the present invention, the livestock sterilizing method according to the first or second aspects is provided, and is further characterized in that the aforesaid ozonized water producing step causes a magnetic force to act on water to be treated and ozone when mixing the ozone into the water to be treated.

According to the sterilizing method of the third aspect, the ozonized water according to the sterilizing method of the first or second aspects is produced by the above described method. By mixing the water to be treated and ozone in the magnetic field, the ozone dissolution degree can be made extremely high. The action of the magnetic force which is exerted on not only the water to be treated but also ozone realizes the high dissolution degree of ozone.

According to a fourth aspect of the present invention, the livestock sterilizing method according to the third aspect is provided, and is further characterized in that in a magnetic field, hydraulic pressure of the water to be treated is increased until it reaches a pressure peak, and is reduced immediately after it reaches the pressure peak, and ozone is supplied to the water to be treated which reaches the pressure peak.

According to the sterilizing method of the fourth aspect, the operational effect of the sterilizing method of the third aspect is efficiently provided by increasing and decreasing the pressure of the water to be treated. The water to be treated is placed under an unstable state by increasing and decreasing the pressure, but the unstable state is considered to accelerate ozone dissolution.

According to a fifth aspect of the present invention, the livestock sterilizing method according to the fourth aspect is provided, and is further characterized in that the water to be treated is passed through a Venturi tube having a small-diameter path, and ozone is supplied through an ozone supply pipe having an open end disposed at a position facing the small-diameter path, and a magnetic force is caused to act on at least the small-diameter path and/or a vicinity of the small-diameter path of the Venturi tube.

According to the sterilizing method of the fifth aspect, the operational effect of the sterilizing method of the fourth aspect can be embodied by the above described constitution. Specifically, the pressure of the water to be treated when flowing into the Venturi tube abruptly increases as it is closer to the small-diameter path, and abruptly decreases after passing through the small-diameter path. The inside of the Ventri tube when the pressure decreases is under vacuum or in a negative pressure state close to a vacuum, and by this negative pressure state, the ozone supplied by the ozone supply pipe is sucked into the water to be treated. The sucked ozone is abruptly stirred and mixed as a result of complicated intertwinement of the above described pressure change, flow change of the water to be treated accompanying passage through the small-diameter path and the like. The gas-liquid mixing structure including the Venturi tube and the ozone supply pipe is also called an ejector.

According to a sixth aspect of the present invention, the livestock sterilizing method according to the fifth aspect is provided, and is further characterized in that the water to be treated which has passed through said Venturi tube is circulated, and is caused to pass through said Venturi tube at least once again while ozone is being supplied.

According to the sterilizing method of the sixth aspect, in addition to the operational effect of the sterilizing method of the fifth aspect, increase and decrease of the pressure, ozone supply and the like in the magnetic field effective for ozone dissolution can be repeated a desired number of times by circulating the water to be treated. By the repetition, the ozone dissolution degree into the water to be treated can be increased. The number of circulations can be determined by the user of the apparatus in accordance with the required ozone dissolution degree and ozone concentration.

According to a seventh aspect of the present invention, the livestock sterilizing method according to the sixth aspect is provided, and is further characterized in that the aforesaid circulated water to be treated is temporarily stored in a storage tank.

According to the sterilizing method of the seventh aspect, in addition to the operational effect of the sterilizing method of the sixth aspect, the water to be treated can be temporarily stored in the storage tank, and by this storage, the water to be treated can be placed in a stable state, whereby, the ozone dissolution into the water to be treated can be accelerated by the action of aging assimilation.

According to an eighth aspect of the present invention, the livestock sterilizing method according to the seventh aspect is provided, and is further characterized in that the water to be treated stored in the aforesaid storage tank is temporarily taken out and kept at a temperature in a range of 5° C. to 15° C.

According to the sterilizing method of the eighth aspect, in addition to the operational effect of the sterilizing method of the seventh aspect, the temperature of the water to be treated can be kept in the above described range. The raw water used for producing ozonized water is often conveyed in a long pipeline, and in such a case, the conveyed raw water is susceptible to the weather. An increase in water temperature in the summer season is especially significant. In order to circulate the water to be treated, energy for circulation is required, and as such an energy source, for example, a pump is cited. The above described energy source is generally accompanied by heat generation, and the heat may increase the temperature of the water to be treated. Ozone dissolution is susceptible to the temperature of water, and when the water temperature rises, reduction in dissolution degree is seen. Thus, by keeping the temperature of the water to be treated in the predetermined range, ozone dissolution is accelerated. The reason why the temperature of the ozonized water is set at 15° C. or lower is that at the temperature of 15° C. or higher, the dissolved ozone escapes and efficiency of the ozone dissolution reduces, as a result a high dissolution degree cannot be expected from the ozonized water. On the other hand, the reason why the temperature of the ozonized water is set at 5° C. or higher is that it is considered that the temperature of 5° C. is necessary in order not to allow the ozonized water to be frozen in the cold district or the like in the winter season since conveyance of the ozonized water to be sprayed to livestock and livestock barns is generally performed outdoors though it depends on the climatic environment, the kind of livestock and the like. If cooling or heating of the water to be treated is unnecessary, the step of keeping the temperature itself may be omitted.

According to a ninth aspect of the present invention, the livestock sterilizing method according to any one of the sixth to eighth aspects is provided, and is further characterized in that the water to be treated after ozone is mixed therein is temporarily stored in a dissolution accelerating tank to accelerate ozone dissolution.

According to the sterilizing method of the ninth aspect, in addition to the operational effect of the sterilizing method of any one of the sixth to eighth aspects, ozone dissolution into the water to be treated is accelerated by the function of the dissolution accelerating tank. The water to be treated stored in the dissolution accelerating tank is placed in the stable state by the storage. In the water to be treated placed in the stable state, ozone dissolution into it is accelerated by the action of aging assimilation.

According to a tenth aspect of the present invention, the livestock sterilizing method according to the ninth aspect is provided, and is further characterized in that ozone escaping from the water to be treated which is stored in the aforesaid dissolution accelerating tank is discharged to an outside of the dissolution accelerating tank.

According to the sterilizing method of the tenth aspect, in addition to the operational effect of the sterilizing method of the ninth aspect, the ozone which is not dissolved in the water to be treated in the process of circulating the water to be treated can be discharged outside the dissolution accelerating tank. By discharging the undissolved ozone, the ozone contained in the water to be treated has a high solubility, and the ozone with a low solubility is discharged. Accordingly, the ozonized water which really has a high ozone dissolution degree is produced.

According to an eleventh aspect of the present invention, the livestock sterilizing method according to any one of the first to tenth aspects is provided, and is further characterized by further including a spraying step of pressurizing the produced ozonized water to predetermined pressure and spraying it from a nozzle or a nozzle group to pour the produced ozonized water on livestock.

According to the sterilizing method of the eleventh aspect, in addition to the operational effect of the sterilizing method of any one of the first to tenth aspects, livestock can be sterilized by nozzle spraying. Nozzle spraying can spread the ozonized water to fine portions, and therefore, is especially preferable for sterilizing the body of livestock. For example, when the flat place such as a livestock barn floor is sterilized, it is sufficient to sprinkle the ozonized water to spread it all over the floor, but when livestock bodies are sterilized, it is not sufficient to simply sprinkle it since the surfaces of the livestock bodies have projections and recesses, in addition to which, the livestock bodies move around, and therefore, nozzle spraying is desired. However, it is assumed that the ozonized water sprayed from the nozzle abruptly has pressure release as compared with the ozonized water in the pressure-fed state before the spraying, and therefore, the contained ozone bubbles expand and are in the state in which they are easily broken. This breakage is considered to be the factor of ozone escape. Accordingly, it is conceivable that when the ozone dissolution degree is low, that is, when the particle sizes of the ozone bubbles are large, they are easily in a size large enough to break when they expand, and as a result, the ozone bubbles are broken. On the other hand, the ozone bubbles contained in the ozonized water according to the present invention have particle sizes of less than 50 nm, and are extremely minute, and therefore, most of them do not reach a size large enough to break even if they expand. Accordingly, ozone escape hardly occurs. Specifically, the ozonized water according to the present invention is the most suitable for nozzle spraying.

According to a twelfth aspect of the present invention, the livestock sterilizing method according to the eleventh aspect is provided, and is further characterized in that the predetermined pressure of the ozonized water at a time of pressurizing and spraying the aforesaid ozonized water is 0.2 MPa to 0.8 MPa.

According to the sterilizing method of the twelfth aspect, in addition to the operational effect of the sterilizing method of the eleventh aspect, the predetermined pressure of the ozonized water sprayed from the nozzle is set in the range of 0.2 to 0.8 MPa, and thereby, reduction in concentration of the ozonized water before nozzle spraying can be effectively realized. Specifically, when the pressure is below the above described range, the case where sufficient ozonized water spraying cannot be performed due to pressure shortage is assumed though it depends on the hole diameter, the number of holes and the like of the nozzle. On the other hand, when the ozonized water is pressurized at pressure exceeding the above described range, the ease where ozone escape occurs due to temperature rise in the pipeline, the nozzle and the like, and the pressure difference caused by the pressure abruptly returning to an atmospheric pressure at the time of spraying is conceivable. Therefore, this is the setting for suppressing such ozone escape as much as possible.

According to a thirteenth aspect of the present invention, the livestock sterilizing method according to the twelfth aspect is provided, and is further characterized in that an average particle size of the ozonized water which is sprayed in the aforesaid spraying step is 40 μm to below 200 μm or 200 μm to 1000 μm. Here, "the average particle size" can be measured by, for example, an immersion method and a laser method.

According to the sterilizing method of the thirteenth aspect, in addition to the operational effect of the sterilizing method of the twelfth aspect, ozonized water spraying corresponding to a purpose can be performed by setting the average particle size in the above described range. Specifically, when the average particle size is 40 to below 200 μm, the ozonized water is in the state close to mist, and therefore, this average size is favorable in the case where livestock is not desired to get extremely wet for preventing it from catching a cold, or the case where the ozonized water is desired to be sprayed to a wide area in a livestock barn. On the other hand, when the average particle size is 200 to 1000 μm, that is, when the average particle size is a particle size close to shower which is used daily by man, the average particle size of 200 to 1000 μm is convenient, for example, in the case where contamination on livestock bodies is desired to be washed out, the case where local spots of livestock bodies (for example, pubic regions) and the like are intensively cleaned and sterilized, or the case where the floor of a livestock barn is desired to be sterilized while being washed. In any case, the ozonized water sprayed from the nozzle can be efficiently spread to livestock or a livestock barn, and by selecting the particle size of the sprayed ozonized water in accordance with the use environment and the use purpose, the possibility of causing livestock to catch a cold or the like when the ozonized water is sprayed to the livestock can be extremely reduced. The ozonized water of the particle size less than the average particle size of 40 μm is relatively light since the particle size is small and easily flown by the natural flow of air after being sprayed though it depends on the environment such as the ventilation characteristic and temperature of the livestock barn. Accordingly, the ozonized water (ozone mist) may not sufficiently spread to the livestock (livestock bodies), the floor of the livestock barn and the like. On the other hand, the ozonized water of the particle size exceeding the average particle size of 1000 μm is practically equal to the ozonized water simply sprinkled with a hose. Accordingly, if it is directly sprayed to livestock, for example, if it is sprayed to a piglet before the weaning stage, there is the possibility of depriving the piglet of body temperature due to wetting since the particle size is too large, and causing the piglet to catch a cold, though it depends on the environment of the livestock barn. From the above reason, the average particle size of the sprayed ozonized water is set in the above described range.

According to a fourteenth aspect of the present invention, the livestock sterilizing method according to any one of the eleventh to thirteenth aspects is provided, and is further characterized by including a step of returning residual ozonized water, which is not sprayed in the aforesaid spraying step and remains, into the aforesaid storage tank by pressure feeding.

According to the sterilizing method of the fourteenth aspect, in addition to the operational effect of the sterilizing method of any one of the eleventh to thirteenth aspects, the residual ozonized water is returned to the storage tank. As a result, increase in efficiency of ozonized water production and regeneration and reuse of the residual ozonized water can be achieved. The residual ozonized water has a higher dissolution degree of ozone as compared with at least raw water though it depends on the environment in which the residual water is placed. Accordingly, as compared with the case of producing the ozonized water of a predetermined concentration from raw water, it is more efficient to regenerate the residual ozonized water to be the ozonized water of a predetermined concentration. Further, if the residual ozonized water is present, it is preferable to reuse it from the viewpoint of efficient use of water resources and produced energy.

According to a fifteenth aspect of the present invention, the livestock sterilizing method according to the fourteenth aspect is provided, and is further characterized by including a step of performing ozonized water spraying after returning the residual ozonized water which is outside the aforesaid storage tank to the aforesaid storage tank before start of the ozonized water spraying, when starting the ozonized water spraying again after temporarily stopping the ozonized water spraying in the aforesaid spraying step.

According to the sterilizing method of the fifteenth aspect, in addition to the operational effect of the sterilizing method of the fourteenth aspect, when restarting ozonized water spraying which is temporarily stopped, the ozonized water spraying is performed after the ozonized water outside the storage tank is returned into the storage tank, and thereby, the ozone dissolution degree (ozone concentration) of the ozonized water to be sprayed can be kept at a desired level. Specifically, the residual ozonized water outside the storage tank is generally in the state where ozone escapes from it though it depends on the environment, the length of the time and the like in which it is placed. Namely, the ozone dissolution degree (ozone concentration) of the residual ozonized water drops. If the ozonized water with the reduced ozone dissolution degree is directly sprayed, a favorable sterilizing effect cannot be expected. Thus, the residual ozonized water with the reduced ozone dissolution degree is reused by being mixed into the ozonized water with a high ozone dissolution degree by temporarily returning it into the storage tank, ozonized water spraying is stopped while the residual ozonized water is returned into the storage tank, and after the residual ozonized water is completely returned, the ozonized water with a high ozone dissolution degree is sprayed. By using the ozonized water with a high ozone dissolution degree which is taken out of the storage tank, the ozonized water at a desired level is sprayed.

According to a sixteenth aspect of the present invention, the livestock sterilizing method according to the eleventh aspect is provided, and is further characterized in that the aforesaid spraying step includes a step of directly spraying the ozonized water to a pubic region of livestock.

According to the sterilizing method of the sixteenth aspect, in addition to the operational effect of the sterilizing method of the eleventh aspect, it is extremely effective to sterilize the pubic region for keeping livestock healthy since saprophytic bacteria easily propagate in pubic regions in both male and female livestock. Especially, when female livestock expecting a baby keeps the pubic region unclean, there is the possibility of occurrence of abnormal delivery of the female livestock and various health troubles of baby livestock to be born. Since the ozonized water, which contacts the livestock body that is an organic substance, reacts with it, and instantly becomes ordinary water, it can be expected to sterilize not only a pubic region but also a vagina and the inside of a womb without side effects. The pubic region of livestock has been sterilized by using chemicals so far, and there has been some doubt as to safety of the chemicals and the side effects to baby livestock. In this respect, there is no doubt as to safety and side effects of ozonized water with a high ozone dissolution degree. Further, there is no possibility of the sprayed ozonized water disrupting the environment, and therefore, it is very favorable. Part of the ozonized water which is sprayed but does not reach the pubic region reaches a livestock body other than the pubic region and sterilizes the portion which it reaches, and the other part of it reaches the floor or the like of the livestock barn and also sterilizes the portion it reaches.

According to a seventeenth aspect of the present invention, the livestock sterilizing method according to the eleventh aspect is provided, and is further characterized in that the aforesaid spraying step includes a step of spraying the aforesaid ozonized water from a position higher than and a position lower than the livestock while letting the livestock move in a column, and a step of performing dewatering by air blow after finishing the ozonized water spraying. For example, the passage between one livestock barn and the other livestock barn is constituted so that livestock can move in a column in it, and sterilizing by the above described method can be performed in the passage. For moving livestock, livestock can be moved by being carried on a belt conveyor or the like, but it is preferable to move the livestock by letting it walk or the like for itself. For example, the livestock carried on the belt conveyor does not move its body so much for itself, but when it is let to walk, the exposed portions of the livestock body change by alternately moving the legs and the like.

According to the sterilizing method of the seventeenth aspect, in addition to the operational effect of the sterilizing method of the eleventh aspect, sterilizing of the entire livestock body can be efficiently performed while suppressing a harmful effect such as catching a cold. Specifically, when the ozonized water is sprayed from above and below livestock while it is being moved, the ozonized water is easily spread over the livestock body. Further, if the livestock is let to walk or the like as described above, the exposed portions change, and therefore, the ozonized water can be uniformly spread over. This enables efficient sterilizing. After the ozonized water is sprayed, dewatering by air blow is performed, and this prevents the livestock which finishes moving from being in a drenched state. This is extremely important to control a disease such as a cold.

According to an eighteenth aspect of the present invention, the livestock sterilizing method according to the seventeenth aspect is provided, and is further characterized in that the aforesaid air blow is performed for livestock at an angle of 20 degrees to 70 degrees with respect to horizontality from above a front with respect to the livestock.

According to the sterilizing method of the eighteenth aspect, in addition to the operational effect of the sterilizing method of the seventeenth aspect, dewatering can be performed more efficiently. Specifically, the hair of livestock generally lies in the direction of the above described angle though it differs depending on the characteristics, the size and the like of the livestock. By substantially matching the hair lying angle and the blow angle, the dewatering effect is enhanced, and this leads to a higher disease suppression rate.

According to a nineteenth aspect of the present invention, the livestock sterilizing method according to any one of the first to eighteenth aspects is provided, and is further characterized in that a livestock facility (for example, a livestock barn, equipment such as a feeder and a cage) and/or a livestock tool (a scoop for conveying feces and urine, clothing and shoes of a feeding worker, a vehicle coming in and going out of a feeding site) are/is sterilized at the same time by using the ozonized water for sterilizing the livestock.

According to the sterilizing method of the nineteenth aspect, in addition to the operational effect of the sterilizing method of any one of the first to eighteenth aspects, livestock is sterilized by pouring the ozonized water on only any one of or both of the facility and the tool for feeding the livestock, or by pouring the ozonized water on the livestock with any one or both of the above. If the facility and tool are sterilized, the livestock raised by using them can be protected from infection of viruses and the like and the livestock can be raised under the hygienic environment. If the livestock is poured the ozonized water at the same time, it is more hygienic and is preferable in keeping the livestock healthy.

According to a twentieth aspect of the present invention, the livestock or livestock meat according to the invention is characterized by being raised while sterilized by being subjected to the ozonized water usable for the livestock sterilizing method according to any one of the eleventh to nineteenth aspects of the present invention.

According to the livestock or the like of the twentieth aspect, it is raised while being sterilized by being subjected to the above described ozonized water, and therefore, it is raised under an extremely hygienic environment. Since the livestock or livestock meat is raised under the strictly controlled hygienic conditions, viruses and the like are inactivated, and the livestock has an extremely low possibility of becoming ill. With ozonized water sterilizing, a chemical disinfectant or the like does not remain in the livestock meat. Since the ozone dissolved in the ozonized water decomposes and disappears by contact with organic substances and the like, it does not remain in the livestock meat. Accordingly, the livestock meat is extremely safe.

According to a twenty-first aspect of the present invention, a livestock sterilizing apparatus is provided, which is constituted by including a pipeline for passing water to be treated through, a gas-liquid mixing structure provided halfway in the pipeline, an ozone supply structure for supplying ozone into the gas-liquid mixing structure, a circulation structure for circulating the water to be treated which has passed through the aforesaid gas-liquid mixing structure to cause the water to be treated to pass through the gas-liquid mixing structure again, a storage tank which is provided halfway in the aforesaid circulation structure and is for temporarily storing the water to be treated, a pressure pump taking out the water to be treated from the storage tank and pressurizing it to predetermined pressure, and a nozzle or a nozzle group for spraying ozonized water pressurized by the pressure pump. On the premise of the above described constitution, the sterilizing apparatus is characterized in that the gas-liquid mixing structure is provided with a magnet for exerting a magnetic force onto an inside, and in that ozonized water with a particle size R of an contained ozone bubble satisfying 0<R<50 and with a ozone concentration of 3 ppm to 20 ppm is capable of being sprayed from the nozzle or the nozzle group.

According to the sterilizing apparatus of the twenty-first aspect, the ozone which is supplied by the ozone supply structure is supplied to the water to be treated which has passed inside the pipeline. Ozone supply is performed in the gas-liquid mixing structure. The water to be treated which has passed through the gas-liquid mixing structure is circulated by the function of the circulation structure, temporarily stored in the storage tank, and passes through the gas-liquid mixing structure again. The gas-liquid mixing structure is provided with a magnet, and therefore, the magnetic force of the magnet is exerted in the process of mixing the water to be treated and ozone. Specifically, the magnetic force action is exerted on not only the water to be treated, but also ozone which is not dissolved in the water to be treated. The water to be treated on the occasion of mixing ozone therein contains ozone bubbles in various sizes large and small, and its flow is an extremely irregular turbulent flow. Therefore, the direction of the magnetic force which acts on the water to be treated and ozone is extremely irregular and unstable.

Whereas it is obvious from the later-described experimental result that the irregular and unstable magnetic force action is effective for production of high-concentration ozonized water having a high dissolution degree, the causal relation is under elucidation at present. The inventor assumes as follows. Specifically, the water to be treated (ozone), which is subjected to the action of the magnetic force, being a turbulent flow, means that the water to be treated is under the action of the magnetic force for a long time as compared with the water to be treated being a laminar flow. Further, the water to be treated (ozone) being a turbulent flow changes the distance from the magnet in rapid succession. Specifically, the magnetic force can be uniformly exerted onto the water to be treated flowing per unit time with much expenditure of time. It is conceivable that this accelerates cluster fragmentation of the water to be treated, and as a result, realizes efficient production of high-concentration ozonized water having a high dissolution degree. The ozonized water which reaches a high concentration of 3 to 20 ppm by production is pressurized by the pressure pump, and is sprayed from the nozzle or the nozzle group. Since the particle sizes of the ozone bubbles contained in the ozonized water are less than 50 nm, ozone stays in the ozonized water and does not escape even when the ozonized water is sprayed.

According to a twenty-second aspect of the present invention, the livestock sterilizing apparatus according to the twenty-first aspect is provided, wherein the aforesaid gas-liquid mixing structure is constituted by including a Venturi tube having a small-diameter path, and an ozone supply pipe having an open end at a position facing the small-diameter path, and the aforesaid ozone supply structure is connected to a connecting end of the ozone supply pipe.

According to the sterilizing apparatus of the twenty-second aspect, basically the same operational effect as the operational effect of the sterilizing apparatus of the twenty-first aspect is provided, and the operational effect in the gas-liquid mixing structure is as follows. Specifically, the pressure of the water to be treated when flowing into the Venturi tube from the pipeline abruptly increases as it is closer to the small diameter path, and after passing through the small diameter path, the pressure abruptly decreases. The inside of the Venturi tube when the pressure decreases is under vacuum or in a negative pressure state close to a vacuum, and by this negative pressure state, the ozone supplied by the ozone supply pipe is sucked into the water to be treated. The sucked ozone is abruptly stirred and mixed as a result of complicated intertwinement of the above described pressure change, flow change of the water to be treated accompanying passage through the small diameter path and the like.

According to a twenty-third aspect of the present invention, the livestock sterilizing apparatus according to the twenty-second aspect is provided, and the aforesaid magnet is constituted to be able to exert a magnetic force onto at least the small-diameter path and/or a vicinity of the small-diameter path of the aforesaid Venturi tube.

According to the sterilizing apparatus of the twenty-third aspect, in addition to the operational effect of the sterilizing apparatus of the twenty-second aspect, the magnetic force can be the most efficiently exerted on the water to be treated when passing through and/or before and after passing through the Venturi tube. According to the experiment of the inventor and the others, when the magnetic force is exerted as described above, high-concentration ozonized water having a high dissolution degree was able to be produced the most efficiently. The reason is supposed as follows. Specifically, when the same magnet is provided at the same Venturi tube, by providing the magnet so that the above described action occurs, a great change occurs to the state of the water to be treated such as occurrence of pressure change to the water to be treated, suction of ozone into the water and the like when or before and after the passage of the water through the small-diameter path of the Venturi tube. It seems to be the factor which realizes the high dissolution degree and high concentration to cause the magnetic force to act on the water to be treated to correspond to the change. Further, it is also assumed to contribute to realization of the high dissolution degree and high concentration to cause the magnetic force to act on ozone bubbles which are paramagnetic substances.

According to a twenty-fourth aspect of the present invention, the livestock sterilizing apparatus according to the twenty-second or twenty-third aspects is provided, and the aforesaid magnet is constituted of a magnetic circuit including one magnet piece and the other magnet piece, and the one magnet piece and the other magnet piece are opposed to each other with the aforesaid Venturi tube therebetween.

According to the sterilizing apparatus of the twenty-fourth aspect, in addition to the operational effect of the sterilizing apparatus of the twenty-second or twenty-third aspects, the magnetic force can be caused to act intensively on a required spot inside the Venturi tube by constituting the magnetic circuit.

According to a twenty-fifth aspect of the present invention, the livestock sterilizing apparatus according to any one of the twenty-second to twenty-fourth aspects is provided, and the magnetic force of the aforesaid magnet is set at 3000 gausses to 20000 gausses.

According to the sterilizing apparatus of the twenty-fifth aspect, in addition to the operational effect of the sterilizing apparatus of any one of the twenty-second to twenty-fourth aspects, the constitution of the magnet can be simply and economically carried out. Specifically, the magnets having the above described magnetic force are easily available on the market, and therefore, special magnets do not have to be prepared. The magnets are inexpensive because they are not special magnets. It goes without saying that this does not intend to inhibit adoption of the magnets having the magnetic force exceeding the above described range.

According to a twenty-sixth aspect of the present invention, the livestock sterilizing apparatus according to any one of the twenty-first to twenty-fifth aspects is provided, and is further provided with a temperature keeping structure for keeping the ozonized water in the aforesaid storage tank at a temperature in a range of 5° C. to 15° C.

According to the sterilizing apparatus of the twenty-sixth aspect, in addition to the operational effect of the sterilizing apparatus of any one of the twenty-first to twenty-fifth aspects, the temperature of the water to be treated can be kept in the above described range by including the temperature keeping structure. The raw water used for producing ozonized water is often conveyed in a long pipeline, and in such a case, the conveyed raw water is susceptible to the weather. An increase in water temperature in the summer season is especially significant. In order to circulate the water to be treated, energy for circulation is required, and as such an energy source, for example, a pump is cited. The above described energy source is generally accompanied by heat generation, and the heat may increase the temperature of the water to be treated. Ozone dissolution is susceptible to the temperature of water, and when the water temperature rises, reduction in dissolution degree is seen. Thus, by keeping the temperature of the water to be treated in the predetermined range, ozone dissolution is accelerated. On the other hand, for example, when the water to be treated is likely to be frozen in a cold district, the sterilizing apparatus may be constituted to heat the water to be treated by providing a heater. If cooling or heating of the water to be treated is unnecessary, the temperature keeping structure itself may be omitted, or the operation of the temperature keeping structure provided therein may be stopped.

According to a twenty-seventh aspect of the present invention, the livestock sterilizing apparatus according to any one of the twenty-first to twenty-sixth aspects is provided, and is further provided with a dissolution accelerating tank for temporarily storing the water to be treated passing through the circulation structure to accelerate ozone dissolution, downstream from the aforesaid gas-liquid mixing structure and upstream from the aforesaid storage tank halfway in the aforesaid circulation structure.

According to the sterilizing apparatus of the twenty-seventh aspect, in addition to the operational effect of the sterilizing apparatus of any one of the twenty-first to twenty-sixth aspects, ozone dissolution into the water to be treated is accelerated by the function of the dissolution accelerating tank. The water to be treated stored in the dissolution accelerating tank is placed in the stable state by the storage. In the water to be treated placed in the stable state, ozone dissolution into it is accelerated by the action of aging assimilation. The ozone which is dynamically dissolved in the gas-liquid mixing structure is statically dissolved in the dissolution accelerating tank, and dissolution of ozone into the water to be treated is dramatically accelerated by the actions of both of them.

According to a twenty-eighth aspect of the present invention, the livestock sterilizing apparatus according to the twenty-seventh aspect is provided, and is further provided with a degassing structure that is capable of discharging ozone, which escapes from the stored water to be treated, at a top portion of the aforesaid dissolution accelerating tank.

According to the sterilizing apparatus of the twenty-eighth aspect, in addition to the operational effect of the sterilizing apparatus of the twenty-seventh aspect, the ozone which is not dissolved in the water to be treated in the process of circulating the water to be treated can be discharged outside the apparatus. By discharging the undissolved ozone, the ozone contained in the water to be treated has a high solubility, and the ozone with a low solubility is discharged. Accordingly, the ozonized water which really has a high ozone dissolution degree is produced.

According to a twenty-ninth aspect of the present invention, the livestock sterilizing apparatus according to any one of the twenty-first to twenty-eighth aspects is provided, and the predetermined pressure by pressurization of the aforesaid pressure pump is set at 0.2 MPa to 0.8 MPa.

According to the sterilizing apparatus of the twenty-ninth aspect, in addition to the operational effect of the sterilizing apparatus of any one of the twenty-first to twenty-eighth aspects, the predetermined pressure is set in the range of 0.2 to 0.8 MPa, and thereby, reduction in concentration of the ozonized water before nozzle spraying can be effectively realized. Specifically, when the pressure is below the above described range, the case where sufficient ozonized water spraying cannot be performed due to pressure shortage is assumed, though it depends on the hole diameter, the number of holes and the like of the nozzle. On the other hand, when the ozonized water is pressurized at pressure exceeding the above described range, the case where ozone escape occurs due to temperature rise in the pipeline, the nozzle and the like and the pressure difference caused by the pressure abruptly returning to an atmospheric pressure at the time of spraying is conceivable, and therefore, this is the setting for suppressing such ozone escape as much as possible.

According to a thirtieth aspect of the present invention, the livestock sterilizing apparatus according to the twenty-ninth aspect is provided, and an average particle size of the ozonized water which is sprayed from the aforesaid nozzle or nozzle group is 40 μm to below 200 μm or 200 μm to 1000 μm.

According to the sterilizing apparatus of the thirtieth aspect, in addition to the operational effect of the sterilizing apparatus of the twenty-ninth aspect, ozonized water spraying corresponding to a purpose can be performed by setting the average particle size in the above described range. Specifically, when the average particle size is 40 to below 200 μm, the ozonized water is in the state close to mist, and therefore, this average size is favorable in the case where livestock is not desired to get extremely wet for preventing it from catching a cold, and the case where ozonized water is desired to be sprayed to a wide area in a livestock barn. On the other hand, when the average particle size is 200 to 1000 μm, that is, when the average particle size is a particle size close to shower which is used daily by man, the average particle size of 200 to 1000 μm is convenient, for example, in the case where contamination on livestock bodies is desired to be washed out, the case where local spots of livestock bodies (for example, pubic regions) and the like are intensively cleaned and sterilized, and the case where the floor of a livestock barn is desired to be sterilized while being washed.

In any case, the ozonized water sprayed from the nozzle or nozzle group can be efficiently spread to livestock or a livestock barn, and by selecting the particle size of the sprayed ozonized water in accordance with the use environment and the use purpose, the possibility of causing livestock to catch a cold or the like when the ozonized water is sprayed to the livestock can be extremely reduced. The ozonized water of the particle size less than the average particle size of 40 μm is relatively light since the particle size is small and easily flown by the natural flow of air after being sprayed though it depends on the environment such as the ventilation characteristic and temperature of a livestock barn. Accordingly, there can be the case where the ozonized water (ozone mist)

does not sufficiently spread to the livestock (livestock bodies), the floor of the livestock barn and the like. On the other hand, the ozonized water of the particle size exceeding the average particle size of 1000 μm is practically equal to the ozonized water simply sprinkled with a hose. Accordingly, if it is directly sprayed to livestock, for example, if it is sprayed to a piglet before the weaning stage, there is the possibility of depriving the piglet of body temperature due to wetting since the particle size is too large, and causing the piglet to catch a cold, though it depends on the environment of the livestock barn. From the above reason, the average particle size of the sprayed ozonized water is set in the above described range.

According to a thirty-first aspect of the present invention, the livestock sterilizing apparatus according to any one of the twenty-first to thirtieth aspects is provided, and is constituted by including a water supply line disposed between the storage tank and an intake port of the aforesaid pressure pump to feed the ozonized water stored in the aforesaid storage tank, a spray line connected to a discharge port of the pressure pump at one side and including the aforesaid nozzle or nozzle group, a return line disposed between the other side of the spray line and the storage tank to return residual ozonized water remaining in the spray line to the storage tank, and a line valve provided in the return line to pressurize the ozonized water in the spray line by closing to spray the ozonized water from the nozzle or nozzle group, and the ozonized water is capable of being sprayed from the nozzle or nozzle group with increase of pressure in the spray line by the closing of the line valve.

According to the sterilizing apparatus of the thirty-first aspect, in the sterilizing apparatus of any one of the twenty-first to thirtieth aspects, the circulation route in which the ozonized water in the storage tank is fed by the pressure pump via the water supply line, and thereafter, passes through the return line via the spray line and is returned to the storage tank is formed. The line valve allows circulation of the ozonized water in the circulation route when it opens, while it stops return of the ozonized water and increases the pressure of the ozonized water in the spray line when it closes. Specifically, the pressure pump pressure-feeds the ozonized water in the state in which the return of the ozonized water is stopped, and thereby, the ozonized water in the spray line is pressurized. When the pressure of the ozonized water reaches the sufficient pressure for causing the nozzle or nozzle group to spray the ozonized water, ozonized water spraying is performed. When the line valve is opened again, the pressure of the ozonized water inside the spray line reduces, and the ozonized water spraying is stopped. At this time, the ozonized water passes without being sprayed from the nozzle or nozzle group, and is returned to the storage tank. When the pressure pump is stopped, circulation of the ozonized water is stopped.

According to a thirty-second aspect of the present invention, the livestock sterilizing apparatus according to any one of the twenty-first to thirty-first aspects is provided, and instead of spraying by the aforesaid nozzle or nozzle group, or in combination with the nozzle spraying, hose spraying is performable.

According to the sterilizing apparatus of the thirty-second aspect, in the sterilizing apparatus of any one of the twenty-first to thirty-first aspects, hose spraying can be performed singly by being switched from nozzle spraying or in combination with the nozzle spraying. Nozzle spraying or hose spraying is properly selected in consideration of the spot to which the ozonized water is sprayed, the amount of the ozonized water required for sterilizing, and the like.

According to a thirty-third aspect of the present invention, the livestock sterilizing apparatus according to any one of the twenty-first to thirty-second aspects is provided, and is characterized by including a moving structure for making the livestock sterilizing apparatus movable. The moving structure refers to a device or a member such as, for example, a truck or a manually-operated tractor capable of conveying the aforesaid sterilizing apparatus by its own power or outside help.

According to the sterilizing apparatus of the thirty-third aspect, in addition to the operational effect of the sterilizing apparatus of any one of the twenty-first to thirty-second aspects, the sterilizing apparatus can be easily conveyed to a place requiring it by the function of the moving structure. Accordingly, if the sterilizing apparatus loaded on a truck (moving structure) is prepared instead of providing the large-scaled water supply line for the ozonized water, a sterilizing operation can be performed by conveying the sterilizing apparatus to the place requiring it in accordance with necessity. The place requiring it may be inside the same feeding facility, or may be in a different feeding facility. Specifically, providing the moving structure enables the sterilizing apparatus to move between different feeding facilities. It is convenient and economical, for example, when one sterilizing apparatus is shared by a plurality of feeding facilities.

Effect of the Invention

According to the sterilizing method and the sterilizing apparatus of livestock and/or a livestock barn according to the present invention, by effectively inhibiting ozone escape from ozonized water, a livestock sterilizing method and its sterilizing apparatus which do not have the possibility of having an adverse effect on man and livestock, and livestock or livestock meat which is raised by using such a sterilizing method can be provided. Accordingly, livestock or a livestock barn, and both of them can be effectively sterilized by ozonized water. As a result, occurrence of foul odors and occurrence of diseases of livestock can be effectively prevented. Further, hygienic livestock or livestock meat can be provided.

Figure 1:
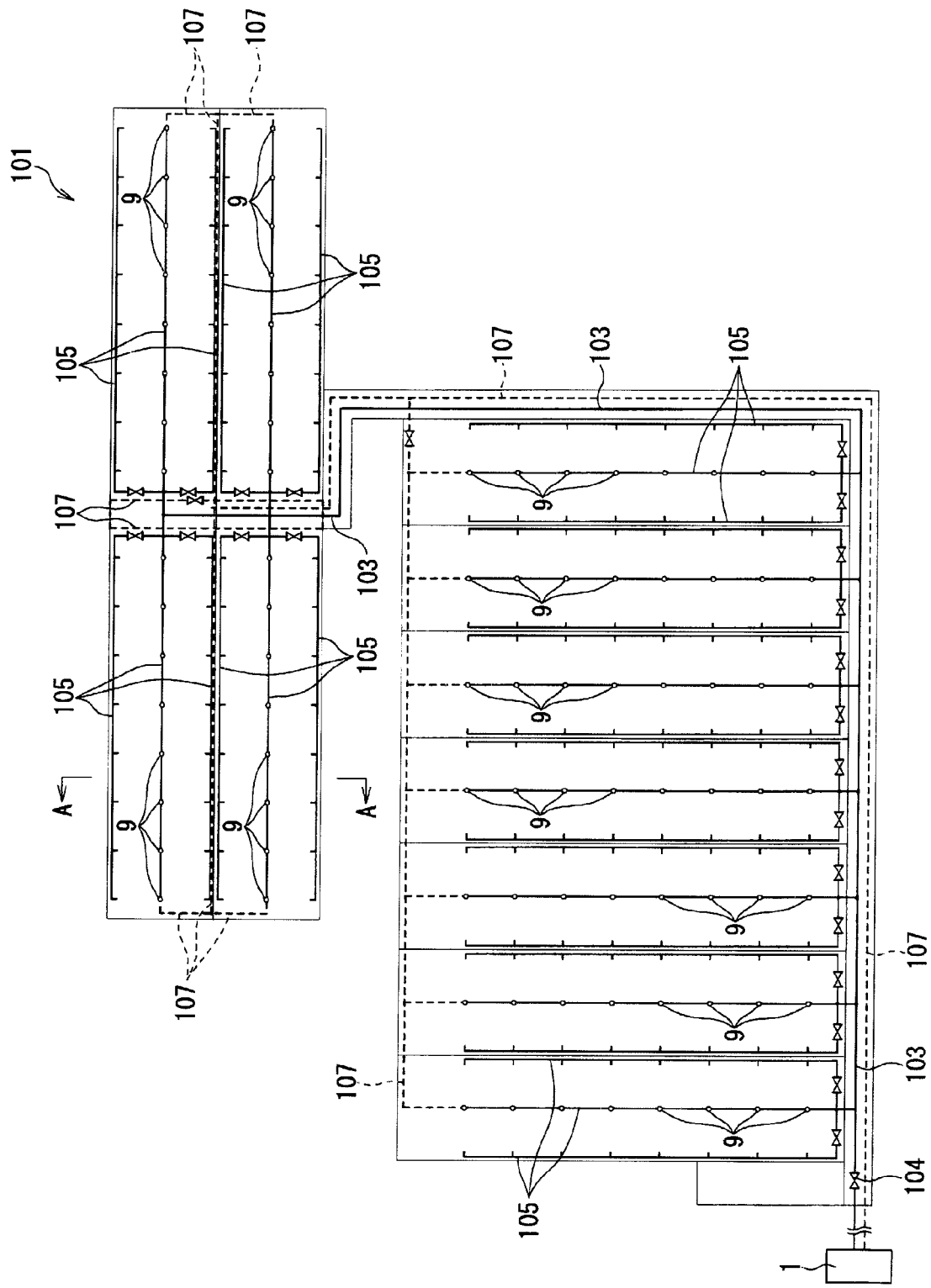
FIG. 1 is a plane view of a pigpen.

DETAILED DESCRIPTION OF THE INVENTION (Sterilizing Method of Livestock and Livestock Barn)

A best mode for carrying out the present invention (hereinafter, properly referred to as "the present embodiment") is as follows. Specifically, sterilizing of livestock and/or a livestock barn can be carried out by an ozonized water producing process of producing ozonized water with particle sizes R of contained ozone bubbles satisfying 0<R<50 nm, and a ozone concentration of 3 to 20 ppm by a gas-liquid mixing method, and a process of sterilizing livestock by using the ozonized water produced in the ozonized water producing process. The ozone concentration of the produced ozonized water needs to be the concentration of 3 to 20 ppm after spraying. The method for dissolving ozone in raw water is also called a gas-liquid mixing method. Other than the gas-liquid mixing method, for example, an electrolysis method is cited, but since an electrolysis method requires an electrolyte such as sodium, and the sodium is likely to do harm to livestock, and therefore, an electrolysis method cannot be used. The reason of requiring the ozone concentration of 3 to 20 ppm will be described in the following paragraph.

The reason of requiring the ozone concentration of 3 to 20 ppm is as follows. Specifically, the ozonized water with the ozone concentration of 3 to 20 ppm sprayed from a nozzle or a hose can cause the sprayed (mist of) ozonized water to reach livestock bodies and cages and the like of a livestock barn in the state of the ozone concentration of substantially 1 ppm, though it may differ depending on the conditions such as the distance from the nozzle to livestock or (equipment or the like in) the livestock barn, the amount of dissolved ozone (ozone dissolved in the raw water) decomposed in accordance with the presence or absence, or a large or small amount of odor gas or the like floating in the air when it is sprayed, and ventilation state inside the livestock barn. As described above in the Background of the Invention section, with the ozonized water having the ozone concentration of 1 ppm, a sufficient sterilizing effect can be obtained, and therefore, foul odors and diseases can be effectively prevented by spraying the above described ozonized water. According to the experiment conducted by the inventor and the others, for efficient production of ozonized water by a gas-liquid mixing method for dissolving ozone in raw water, about 20 ppm is the limit. It is possible to produce ozonized water exceeding 20 ppm, but it has been found out that such ozonized water is not suitable for sterilizing livestock in which a large amount of ozonized water is required because the production efficiency of such ozonized water is significantly low. In this case, an additive or the like for enhancing the ozone concentration is not used. The ozone concentration before spraying for making the ozone concentration after the spraying 3 to 20 ppm is substantially in a range of 3 to 20 ppm though it is susceptible to the pressure of the ozonized water when sprayed, the particle size of ozonized water when sprayed, the use environment such as outside temperature and the like. In the case of nozzle spraying, the pressure change at the time of spraying is larger as compared with the pressure change at the time of hose spraying, and ozone is likely to escape correspondingly at the time of spraying though in a very small amount. Accordingly, in the case of nozzle spraying, ozonized water with a slightly higher concentration than the ozone concentration required after spraying is preferably produced, though this is hardly required in the case of hose spraying. When verifying the additional effect by using the sterilizing method according to the present embodiment, the inventor has found out that the ozonized water with the ozone concentration increased to about 7 to 8 ppm is extremely effective for envelope viruses (helpes virus, paramyxovirus, orthomyxovirus, coronavirus, and the like) which are generally regarded as difficult to disinfect, further, large viruses without envelopes (adenovirus, reovirus, papovavirus and the like), and even small viruses without envelopes (picornavirus, parvovirus and the like).

In concrete, when 0.5 ml of a virus liquid (culture medium containing 2% of fetal bovine serum) was inoculated into 100 ml of ozonized water, the disinfection effect (inactivation) was able to be obtained substantially instantly. Accordingly, though it depends on the presence, absence or the like of the above described odor gas flowing in the atmosphere, when ozonized water with a high concentration of 9 to 10 ppm, for example, is sprayed in view of the amount of ozone which will be decomposed by reacting with the odor gas after sprayed, so that ozonized water of 7 to 8 ppm can reach livestock or a livestock barn, envelope viruses and the like can be effectively disinfected (inactivated). The concentration of the ozonized water after being sprayed may be properly selected from the range of 3 to 20 ppm in accordance with the kinds of apprehended germs and viruses, the use environment, the kind of target livestock, the production cost of the ozonized water and the like.

The sterilizing method using ozonized water includes spraying, sprinkling, coating, wetting and the like, and in the case of spraying ozonized water, a method of spraying like shower, and a method of spraying in a fine mist form (misting) are cited. Further, there is a method for spraying by using a hose. They may be properly used in accordance with the sterilizing purposes. For example, when livestock is desired to be poured in a large amount of ozonized water, and when the floor, cages and the like of a livestock barn are intensively sterilized, it is convenient to sterilize them by a shower method and a hose method. On the other hand, when the entire livestock barn in which livestock is present is desired to be sterilized, a method by misting is suitable. The average particle size of ozonized water when carrying out misting can be properly set in the range of 40 to below 200 μm or 200 to 1000 μm in accordance with the sterilizing targets, use environments and the like. The ozonized water differing in particle size may be properly sprayed at the same time or at different times in such a manner that the ozonized water with a small particle size is used for sterilizing young livestock, and the ozonized water with a large particle size is for sterilizing parent livestock and the floor of a livestock barn. This is for the reason that since the pressure of the ozonized water to be sprayed needs to be set in the above described range of 0.2 to 0.8 MPa, in order to spray the ozonized water in such a pressure range, the average particle size has a fixed limit, and this is also for the reason that such a particle size is considered to be suitable for causing the ozonized water sprayed from the nozzle to spread efficiently to livestock and the livestock barn, and preventing the livestock from catching a cold.

It is important that the ozonized water used for sterilizing livestock has a high ozone dissolution degree. The ozonized water with a high ozone dissolution degree refers to the ozonized water with the particle sizes of the contained ozone bubbles being less than 50 nm. This is because the ozone bubbles having the particle sizes of less than 50 nm hardly receive buoyancy from the ozonized water, and therefore, ozone does not float on a free surface of the ozonized water, but stay in the ozonized water. Staying means not escaping. It is supposed that the ozonized water kept at high pressure for pressure feeding before being sprayed is abruptly released from pressure by spraying, and the impact due to the pressure change on the occasion of the spraying causes ozone to escape from the ozonized water, but the ozone bubbles with the particle sizes of 50 nm do not expand enough to be broken by the pressure release, and therefore, the ozone bubbles stay in the ozone water. Specifically, ozone escape does not occur. Production of the ozonized water containing ozone bubbles of particle sizes of less than 50 nm can be achieved by mixing the water to be treated and ozone in a magnetic field. Ozone dissolution by the above described method does not change the pH values of the raw water and the produced ozonized water. It is said that when ozonized water is neutral, ozone hardly escapes from it, and the ozonized water according to the present invention does not require an additive for adjusting the pH value. In the case of using nozzle spraying for sterilizing livestock and a livestock barn, the average particle size of the ozonized water suitable for nozzle spraying is preferably set at 40 to below 200 μm or about 200 to 1000 μm. This is because the particle size in this range is favorable for uniformly spreading the ozonized water to livestock bodies and the livestock barn. The predetermined pressure of the ozonized water when the ozonized water is sprayed by pressure is set at 0.2 to 0.8 MPa. This is because if the pressure is too low, smooth spraying cannot be performed, and if it is too high, the pressure difference before and after spraying becomes so large that the dissolved ozone is likely to escape.

The ozonized water which is produced or is being produced is temporarily stored in a storage tank, and the stored ozonized water is preferably kept in the range of 5 to 15° C. to suppress ozone escape. If the ozonized water temporarily stored in the storage tank is left as it is, ozone will gradually escape naturally or by means of self-decompose. Therefore, the ozonized water is let out of the storage tank, after which, it is circulated by pressure feeding and returned to the storage tank, and gas-liquid mixing is preferably repeated for keeping the ozone of the ozonized water at a predetermined concentration in the circulation process. Ozone does not necessarily have to be supplied continuously, and ozone is supplied only when the ozone concentration becomes lower than the predetermined concentration while monitoring the ozone concentration of the ozonized water in the storage tank. The residual ozonized water remaining without being sprayed reduces in its ozone concentration with the lapse of time, but can be reused by dissolving ozone in it again. For reuse, ozonized water needs to be passed through (circulate) the above described circulation process at least once (twice or more may be adoptable) by being pressure-fed, and ozone needs to be dissolved to a predetermined concentration. This is especially important when ozonized water spraying is started again after the ozonized water spraying is temporarily stopped. This is because if ozonized water spraying is performed after the residual ozonized water which is outside the storage tank is returned to the storage tank by pressure feeding before starting the ozonized water spraying, it can be avoided to spray the residual ozonized water with the ozone concentration reduced, that is, with a low sterilizing effect.

Figure 17:
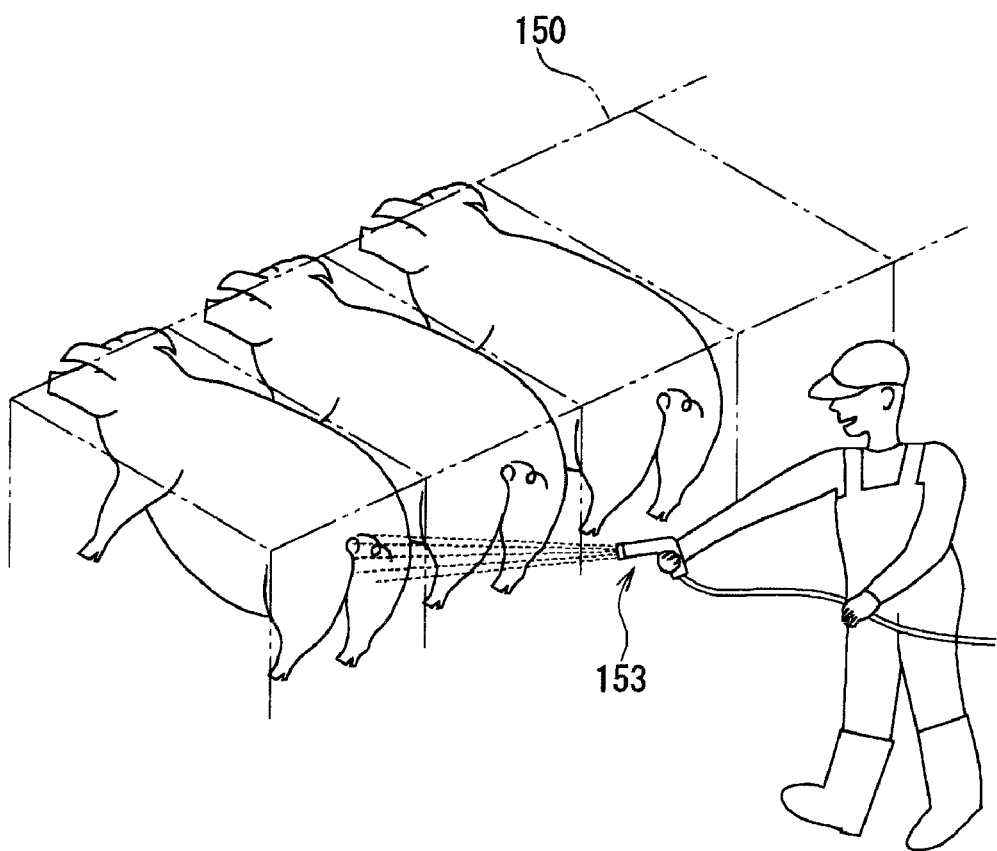
FIG. 17 is a view showing a state of washing livestock.
Figure 18:
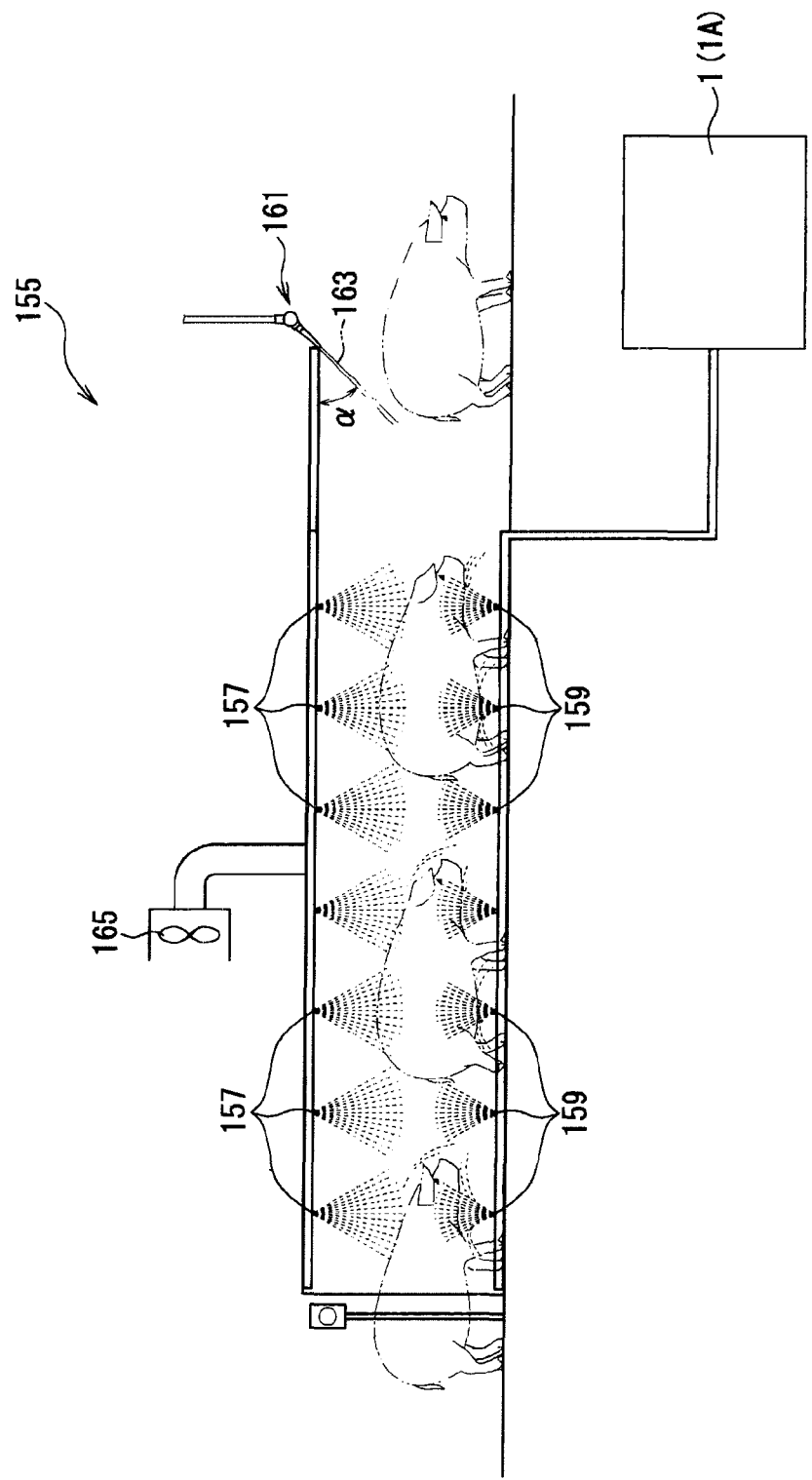
FIG. 18 is a view showing the state of washing the livestock.

The ozonized water is basically sprayed so as to spread uniformly to livestock and the livestock barn, but it is suitable to spray the ozonized water directly to a pubic region of livestock which tends to be unclean at the same time. On this occasion, it is effective to let the livestock into a cage 150 as shown in FIG. 17, and to perform ozonized water spraying from a nozzle 153 with the livestock standing in row. When this sterilizing method is applied to female livestock expecting its baby, it is extremely effective for keeping health of both the female livestock and its newborn baby livestock. Further, while the livestock is moved in a column in a sterilizing passage 155 as shown in FIG. 18, the ozonized water is sprayed from nozzles 157, 157, 159 and 159 provided at positions higher and lower than the livestock, and it is desired to blow air from a blower 161 to perform dewatering after finishing spraying the ozonized water so as to prevent the livestock from catching a cold after spraying the ozonized water. Air blow is performed for the livestock with an angle α (the angle of the air 163 shown in FIG. 18 and horizontality) of 20 to 70 degrees with respect to the horizontality from above the front with respect to the livestock. Depending on the kind of livestock, this is for enhancing the dewatering effect by matching the angle to the angle of the lie of hair of the livestock. In order to confirm the effect of carrying out the above described sterilizing method of livestock and a livestock barn, the following experiment was conducted. Reference numeral 165 denotes a ventilation device for ventilating the sterilizing passage 155. The amount of ozone escaping from the sprayed ozonized water satisfies the safety standards, but in order to secure greater safety, the ventilation device 165 is preferably provided. The sterilizing passage 155 can be installed in an appropriate place, and if it is arranged between livestock barns, infection between the livestock barns can be effectively prevented.

(Experiment 1)

As described in the above described Non-patent Document 2, the dissolved ozone easily escapes or decomposes by spraying the ozonized water, but the inventor and the others confirmed by experiment 1 that the escape or decomposition can be effectively suppressed by fragmenting the clusters of raw water (activation of the raw water) as the method for suppressing the speed of escape or decomposition on the occasion of pressurizing and spraying. The result of the experiment 1 is as shown in Tables 2 and 3.

TABLE 2

|  | TIME TO REACH CONCENTRATION 2 ppm | TIME TO REACH CONCENTRATION 4 ppm |
|---|---|---|
| PRODUCE OZONIZED WATER DIRECTLY FROM TAP WATER | 32 min 50 sec | 72 min 10 sec |
| FRAGMENT CLUSTERS | 25 min 20 sec | 60 min 20 sec |

RECORDED BY TIME AT THE TIME POINT WHEN ULTRAVIOLET RAY ABSORPTION TYPE OZONIZED WATER DENSITOMETER VALUE SHOWS PREDETERMINED CONCENTRATION CONTINUOUSLY FOR 10 SEC OR MORE.

Table 2 shows the comparison of the times until the ozonized water reaches the ozone concentrations of 2 ppm and 4 ppm after ozone is dissolved in raw water (tap water). At this time, the capacity of the tank for storing the ozonized water was one ton, the ozone gas generation amount was 10 g/h, and the water temperature was 22 to 23° C. The time to reach the concentration is the time until the point of time when the numerical value of the ultraviolet ray absorption type ozonized water densitometer shows a predetermined concentration for 10 seconds or more from the start of ozone dissolution. While the time to reach 2 ppm when generating the ozonized water by directly using tap water (raw water) without mounting a raw water fragmenting structure for fragmenting the clusters of the raw water was 32 minutes and 50 seconds, the time to reach 2 ppm when producing the ozonized water after fragmenting the clusters by mounting a raw water fragmenting structure 11 which will be described in the section of the present embodiment which will be described later was 25 minutes and 20 seconds. Reduction in percentage by about 22.8%, and in time by 7 minutes and 30 seconds was achieved. While the time to reach 4 ppm of the raw water under the same conditions was 72 minutes and 10 seconds, the time to reach 4 ppm after fragmenting the clusters was 60 minutes and 20 seconds. Reduction in percentage by about 16.4%, and in time by 11 minutes and 50 seconds in time was achieved. From the above experiment, it is assumed that ozone was easily dissolved in the raw water by fragmenting the clusters.

TABLE 3

|  | TIME TO REDUCE BY ONE HALF FROM 4 ppm →2 ppm |
|---|---|
| PRODUCE OZONIZED WATER DIRECTLY FROM TAP WATER | 44 min |
| FRAGMENT CLUSTERS | 69 min |

OUTSIDE AIR TEMPERATURE 18° C.

Table 3 shows the comparison of the times until the ozone concentration of 4 ppm produced by the experiment 1 reduced by half to 2 ppm. In the case of producing the ozonized water without mounting the later-described raw water fragmenting structure 11 (production of the ozonized water directly from tap water), the time to reduce by half was 44 minutes, but in the case of producing the ozonized water by mounting the raw water fragmenting structure 11 (cluster fragmentation), the time to reduce by half was 69 minutes, which was found to be long by about 36%. Taking a long time to reduce by half means that even when using the ozonized water of the same concentration of 4 ppm, the ozonized water that is subjected to cluster fragmentation has a high ozone dissolution degree, that is, ozone hardly escapes or decomposes. The ozonized water at this time showed very slight acidity or neutrality of pH5 to 7.5.

(Experiment 2)

In the experiment 2, the ozonized water was sprayed in the test room in which the ozonized water used in the experiment 1 was sealed, and the ozone concentration in the test room was measured with the lapse of time. The comparison targets were the ozonized water which was not subjected to cluster fragmentation, and the ozonized water produced by an electrolytic method. The test room was formed by partitioning the space of a depth of 1700 mm, a width of 2800 mm and a height of 2050 mm with a resin sheet. The inside of the test room had no wind or odor. The ozone water of 4 ppm was pressurized to the pressure of 0.4 MPa (4 kg/cm$^2$) and the average particle size was made 110 to 150 μm. The spraying angle was made about 90° downward from the test room ceiling. The experimental result is as shown in Table 4 and FIG. 29, which is a graphic plot of what is shown in Table 4.

TABLE 4

| | OZONIZED WATER PRODUCING METHOD AND INDOOR OZONIZED GAS CONCENTRATION (UNIT: ppm) | | |
|---|---|---|---|
| ELAPSED TIME (sec) | ① CLUSTER FRAGMENTATION | ② ORDINARY GAS-LIQUID MIXING | ③ ELECTROLYTIC METHOD |
| 20 | 0.02 | 0.07 | 0.06 |
| 30 | 0.02 | 0.09 | 0.10 |
| 40 | 0.02 | 0.13 | 0.10 |
| 50 | 0.03 | 0.12 | 0.14 |
| 60 | 0.03 | 0.17 | 0.18 |
| 70 | 0.03 | 0.24 | 0.27 |
| 80 | 0.04 | 0.38 | 0.40 |
| 90 | 0.05 | 0.50 | 0.60 |
| 120 | 0.07 | 1.20 | 1.30 |
| 140 | 0.08 | 1.40 | 1.20 |
| 160 | 0.09 | 1.80 | 1.90 |
| 180 | 0.10 | 1.90 | 2.00 |
| 210 | 0.12 | 2.20 | 2.30 |
| 240 | 0.14 | 2.40 | 2.60 |
| 270 | 0.13 | 2.70 | 3.00 |
| 300 | 0.16 | 2.60 | 3.20 |

* REGARDLESS OF PRODUCING METHODS OF ① TO ③, OZONIZED WATER CONCENTRATION IN TANK BEFORE DISCHARGE IS 4 ppm (VARIATION/ERROR RANGE LESS THAN ±10%)
* WHEN MISTING IN BARN, USUALLY WITHIN 30 SEC TO 120 SEC. EXPECTABLE MAXIMUM TIME WAS REGARDED AS 300 sec (5 min).

Figure 29:
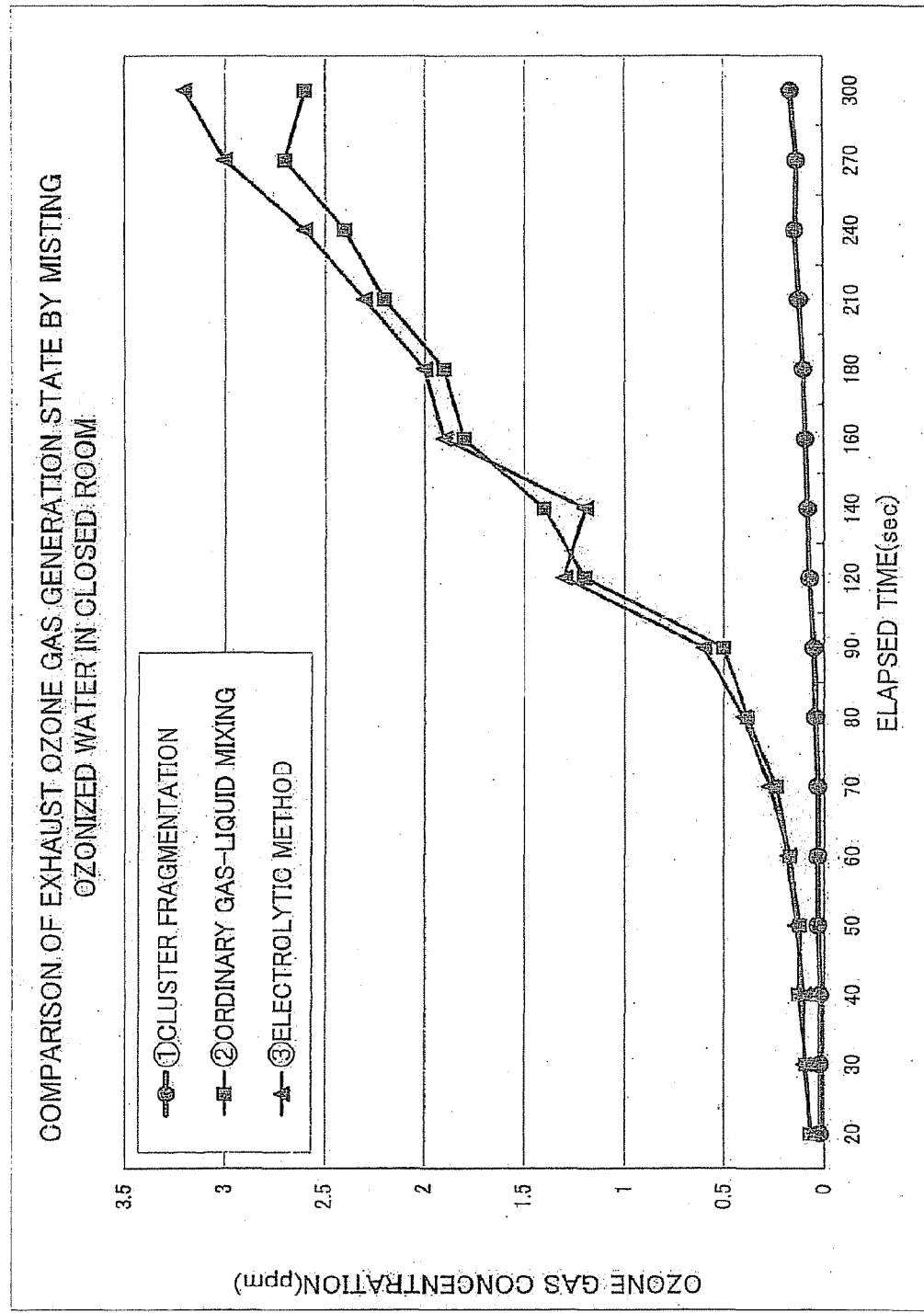
FIG. 29 is a graphic plot of the data in Table 4.

As shown in Table 4 and FIG. 29, it has been found out that the ozone concentration in the test room when the fragmented raw water in which the clusters were fragmented was sprayed was 0.1 ppm or less which is the safety standard of ozone gas until 180 seconds elapsed after spraying. 180 seconds is sufficient time for the sprayed ozonized water to spread livestock and to every corner of the livestock barns. Further, even after 300 sec elapsed after the spraying, the ozone concentration was only 0.16 ppm which slightly exceeded the safety standard. The experiment 2 was the experiment conducted in the closed room with no wind and no odor. Therefore, if it is conducted in an actual livestock barn, a more preferable result can be obtained, and thus the ozone concentration has no problem in actual use. This is because the above described experiment was conducted in the narrow closed space without wind or odor, but the inside of the actual livestock barn cannot be windless, and various organic matters are floating, so that the sprayed ozonized water reacts with these organic matters and decomposes to make the ozone concentration lower. From the experiment 2, it has been found out that the ozonized water produced in the experiment 1 does not increase the ozonized concentration inside the livestock barn to the safety standard or more, and the livestock and workers are safe in the livestock barns. On the other hand, in the other two kinds of ozonized water without using the fragmented raw water, the ozone concentration when 40 seconds elapses at latest after the spraying exceeded 0.1 ppm.

(Experiment 3)

In the experiment 3, the comparison experiment of the produced ozone concentration for producing the ozonized water of which ozone concentration after spraying is 3 ppm or more was conducted in the relationship with the pressure of the ozonized water before spraying. The ozone concentration after spraying was measured by the ultraviolet ray absorption device by extracting the sprayed ozonized water. Since the sprayed ozone easily reacts with the organic matters and the like in the atmosphere into which it is sprayed and decomposes, it was extracted at the position of about 10 cm from the nozzle in order to prevent the reaction with them as much as possible. The ozone concentration (produced concentration) of the produced ozonized water was changed stepwise from 2 to 20 ppm, and nozzle spraying of it was performed by the pumps having different discharge pressures. The average particle size of the sprayed ozonized water was 80 μm at 0.5 MPa (5 kg/cm$^2$), and was 40 at 1.5 MPa (15 kg/cm$^2$). The result of the experiment 3 is as shown in Table 5.

TABLE 5

| PRODUCED CONCENTRATION | PUMP CONDITION OZONIZED WATER CONCENTRATION AFTER DISCHARGE (UNIT ppm) | | | | |
| --- | --- | --- | --- | --- | --- |
| | 0.3 MPa | 0.5 MPa | 0.8 MPa | 1.5 MPa | 3 MPa |
| 2 ppm | 1.8 | 1.6 | 0.7 | 0.0 | 0.0 |
| 3 ppm | 2.7 | 2.4 | 1.1 | 0.0 | 0.0 |
| 4 ppm | 3.6 | 3.2 | 1.5 | 0.0~0.3 | 0.0 |
| 5 ppm | 4.3 | 3.8 | 1.8 | 0.0~0.5 | 0.0 |
| 6 ppm | 4.8 | 4.2 | 2.0 | 0.5~1.0 | 0.0 |
| 8 ppm | 5.8 | 5.0 | 2.5 | 0.0~1.0 | 0.0 |
| 10 ppm | 6.5 | 5.5 | 2.8 | 0.0~1.0 | 0.0 |
| 12 ppm | 7.1 | 6.3 | 3.1 | 0.0~0.5 | 0.0 |
| 15 ppm | 8.2 | 7.3 | 3.8 | 0.0~0.5 | 0.0 |
| 18 ppm | 9.1 | 8.3 | 4.4 | 0.0~0.5 | 0.0 |
| 20 ppm | 10.0 | 9.1 | 5.0 | 0.0~0.5 | 0.0 |

*MEASURE CONCENTRATION BY EXTRACTING OZONIZED WATER INTO CONTAINER AT SPOT 100 mm FROM NOZZLE.
SINCE NUMERICAL VALUE OF DISSOLVED OZONE CONCENTRATION DELICATELY VARIES, CENTER OF MEASURED NUMERAL VALUE WAS READ AND WRITTEN.

When spraying was performed by using the pump with the discharge pressure of 1.5 MPa, all the produced concentrations were below 3 ppm, as shown in Table 5. In the spraying using the pump with the discharge pressure of 3 MPa, ozone completely escaped or decomposed and did not remain. On the other hand, when spraying was conducted by using the pumps at 0.3 MPa, 0.5 MPa and 0.8 MPa, the ozone concentration after spraying of about 3 ppm or more was obtained. From the above experimental result, it has been found out that the lower the discharge pressure was made, the higher the ozone concentration after spraying became. Considering the result of the experiment 2 and the fact that the minimum required discharge pressure (spraying cannot be performed at pressure which is too low) for spraying ozonized water is about 0.2 MPa, it has been found out that livestock and the livestock barn can be sterilized at the same time or separately if the discharge pressure, that is, the pressure of the ozonized water to be sprayed is set in the range of 0.2 to 0.8 MPa, when the spraying concentration is set at 3 to 20 ppm.

(Experiment 4)

In the experiment 4, the relationship between the water temperature and the ozone concentration was studied. First, Table 6 shows the relationship of the ozone concentration of the ozonized water with a high ozone dissolution degree, that is, the ozonized water with particle sizes of the contained ozone bubbles being less than 5 nm, and the time required to establish the ozone concentrations shown in Table 6 by dissolving ozone in the raw water (that is, zero ppm). As is read from Table 6, when the water temperature is, for example, 10° C., the ozone concentration reaches 2.5 ppm within ten minutes after starting production, and reaches 14.8 ppm which is about 15 ppm 250 minutes later. It has been found out that when the water temperature is kept at 10° C., the ozonized water with the required highest concentration can be obtained in about 250 minutes. The ozone concentration 250 minutes later in the case of dissolving ozone under the same conditions except for the water temperature was 9.6 ppm at water temperature of 20° C., and was 4.7 ppm at water temperature of 30° C. Studying the experimental result from the different angle, the ozone concentration of 9.6 ppm which requires 250 minutes at the water temperature of 20° C. was obtained in 70 and several minutes (between 70 minutes and 80 minutes in Table 6) which is about one third when the water temperature was set at 10° C. to obtain the ozonized water of the same concentration. Similarly, the ozone concentration of 4.7 ppm at the water temperature of 30° C. is achieved in less than 30 minutes, which is one eighth, at the water temperature of 10° C. From the above, it has been found out that when ozone is dissolved by using the same apparatus, the water temperature exerts a large influence on the ozone concentration, shorter time is required for producing the ozonized water of the same concentration at lower water temperature, and if the production is performed by taking the same time, the ozonized water of a higher concentration can be obtained at lower water temperature.

Table 7 shows the relationship of the reduction in ozone concentration and the time when the ozonized water shown in Table 6 was left standing with the ozonized water producing apparatus stopped. In the case of the water temperature set at 10° C., it took 430 minutes for the ozone concentration which was 14.8 ppm to decrease to zero. In other words, the ozonized water kept the dissolved state without allowing ozone to escape for 430 minutes after stopping ozone supply. On the other hand, when the water temperature was set at 20° C., it took 190 minutes, and when the water temperature was set at 30° C., it took 60 minutes. Considering the experimental result from the different angle, the time taken for the ozone concentration of 9.6 ppm to reach zero, which was 190 minutes at the water temperature of 20° C., was 270 minutes which was from 160 minutes after stopping (the ozone concentration at this time was 9.6 ppm) to 430 minutes at the water temperature of 10° C., that is, about 1.42 times (≈270÷190) as long as 190 minutes. Similarly, the time for the ozone concentration 4.7 ppm to reach zero which was 60 minutes at the water temperature of 30° C. was 340 minutes which was from 90 minutes after stopping (the ozone concentration at this time was 4.8 ppm) to 430 minutes at the water temperature of 10° C., that is, about 5.7 times (≈340÷60) as long as 60 minutes. From the above, it has been found out that as the water temperature is lower, ozone can be kept without escaping for a longer time.

TABLE 6

| TIME (min) | 10° C. PPM | 20° C. PPM | 30° C. PPM |
| --- | --- | --- | --- |
| 0 | 0 | 0 | 0 |
| 10 | 2.5 | 1.5 | 0.8 |
| 20 | 3.7 | 2.4 | 1.3 |
| 30 | 5.2 | 3.3 | 1.7 |
| 40 | 6.5 | 4.1 | 2.1 |
| 50 | 7.6 | 4.8 | 2.4 |
| 60 | 8.5 | 5.4 | 2.7 |
| 70 | 9.3 | 5.8 | 2.9 |
| 80 | 9.9 | 6.2 | 3.1 |
| 90 | 10.6 | 6.6 | 3.3 |
| 100 | 11.2 | 7.0 | 3.5 |
| 110 | 11.7 | 7.3 | 3.7 |
| 120 | 12.2 | 7.5 | 3.8 |
| 130 | 12.6 | 7.8 | 3.9 |
| 140 | 13.2 | 8.0 | 4.0 |
| 150 | 13.6 | 8.2 | 4.1 |
| 160 | 13.75 | 8.4 | 4.2 |
| 170 | 13.85 | 8.6 | 4.3 |
| 180 | 14.0 | 8.9 | 4.4 |
| 190 | 14.2 | 9.1 | 4.5 |
| 200 | 14.3 | 9.2 | 4.6 |
| 210 | 14.4 | 9.4 | 4.7 |
| 220 | 14.6 | 9.5 | 4.7 |
| 230 | 14.7 | 9.5 | 4.7 |
| 240 | 14.8 | 9.5 | 4.8 |
| 250 | 14.8 | 9.6 | 4.7 |

TABLE 7

| TIME (min) | 10° C. PPM | 20° C. PPM | 30° C. PPM |
| --- | --- | --- | --- |
| 0 | 14.8 | 9.6 | 4.7 |
| 10 | 14.5 | 9.1 | 3.8 |
| 20 | 14.1 | 8.5 | 2.7 |
| 30 | 13.8 | 7.9 | 1.7 |
| 40 | 13.5 | 7.4 | 0.8 |
| 50 | 13.2 | 6.9 | 0.2 |
| 60 | 13.0 | 6.3 | 0.0 |
| 70 | 12.6 | 5.8 | |
| 80 | 12.2 | 5.3 | |
| 90 | 11.9 | 4.8 | |
| 100 | 11.5 | 4.3 | |
| 110 | 11.1 | 3.7 | |
| 120 | 10.7 | 3.2 | |
| 130 | 10.5 | 2.7 | |
| 140 | 10.2 | 2.3 | |
| 150 | 9.8 | 1.8 | |
| 160 | 9.6 | 1.3 | |
| 170 | 9.2 | 0.8 | |
| 180 | 8.8 | 0.3 | |
| 190 | 8.6 | 0.0 | |
| 200 | 8.3 | | |
| 210 | 8.0 | | |
| 220 | 7.7 | | |
| 230 | 7.3 | | |
| 240 | 6.9 | | |
| 250 | 6.5 | | |
| 260 | 6.2 | | |
| 270 | 5.8 | | |
| 280 | 5.5 | | |
| 290 | 5.1 | | |
| 300 | 4.7 | | |
| 310 | 4.1 | | |
| 320 | 3.7 | | |
| 330 | 3.3 | | |
| 340 | 3.0 | | |
| 350 | 2.7 | | |
| 360 | 2.3 | | |
| 370 | 2.0 | | |
| 380 | 1.7 | | |
| 390 | 1.4 | | |
| 400 | 1.0 | | |
| 410 | 0.7 | | |
| 420 | 0.2 | | |
| 430 | 0.0 | | |

(Sterilizing Apparatus)

Figure 2:
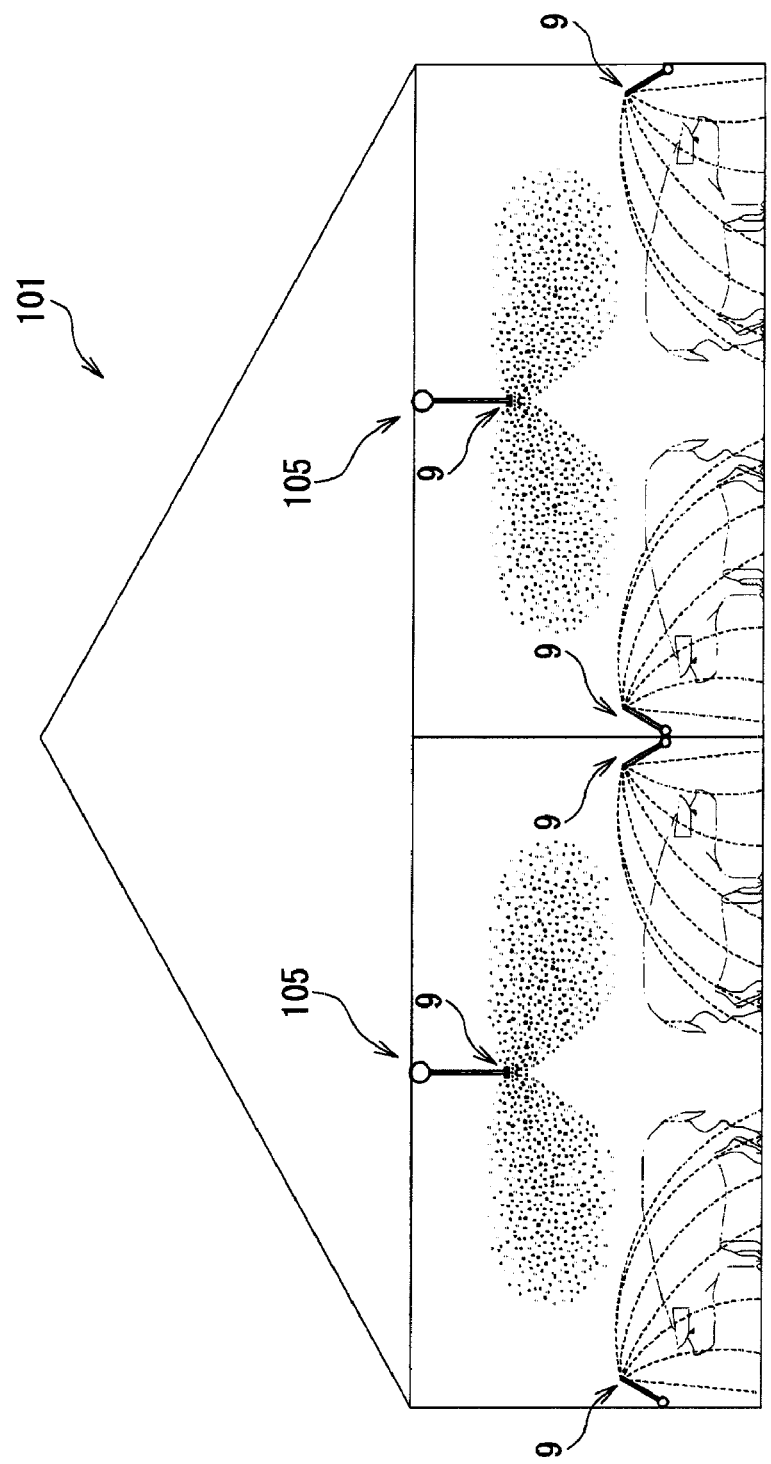
FIG. 2 is a sectional view taken along the line A-A of the pigpen shown in FIG. 1.
Figure 3:
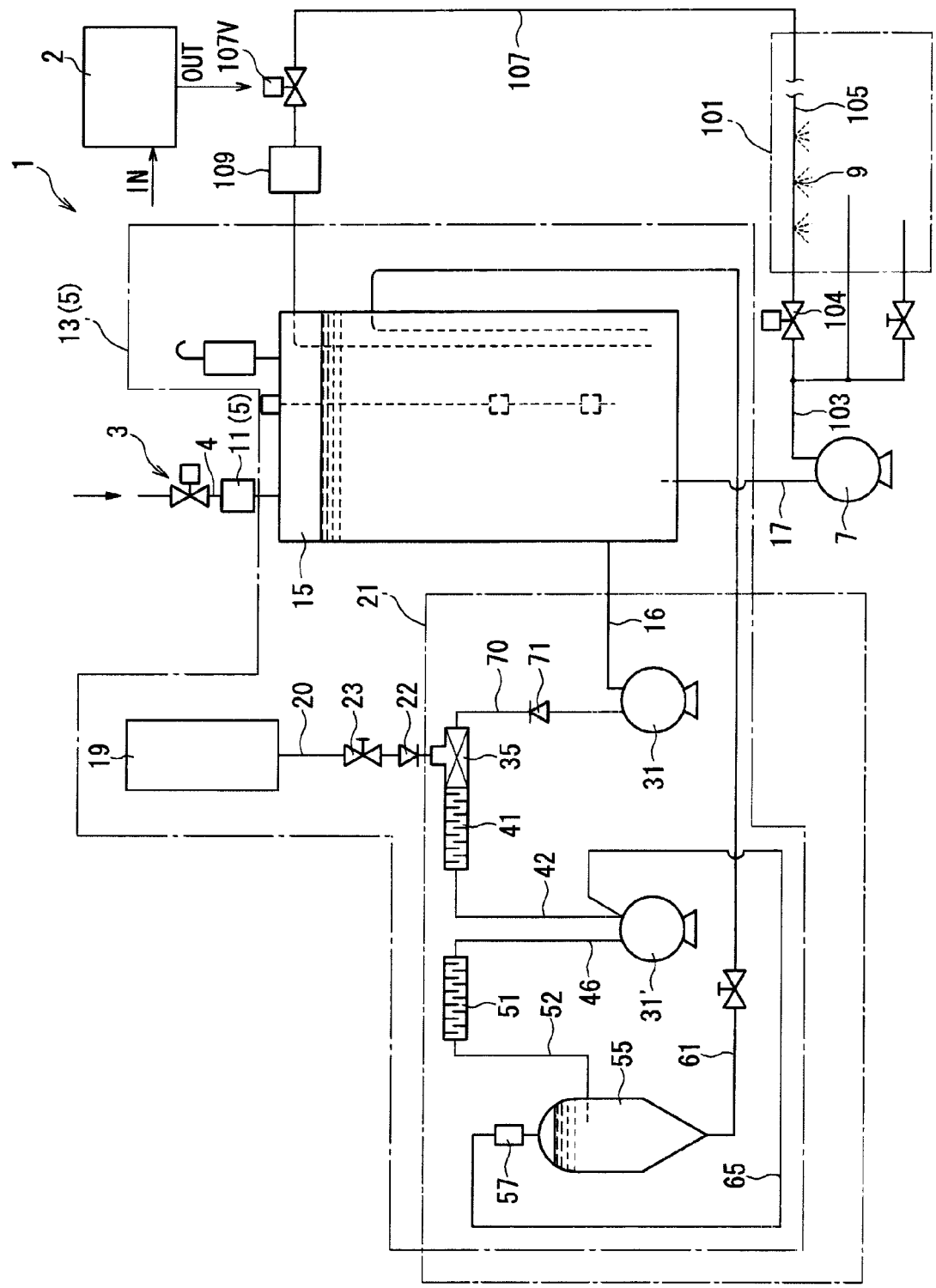
FIG. 3 is a schematic block diagram of a sterilizing apparatus capable of producing and spraying ozonized water.
Figure 4:
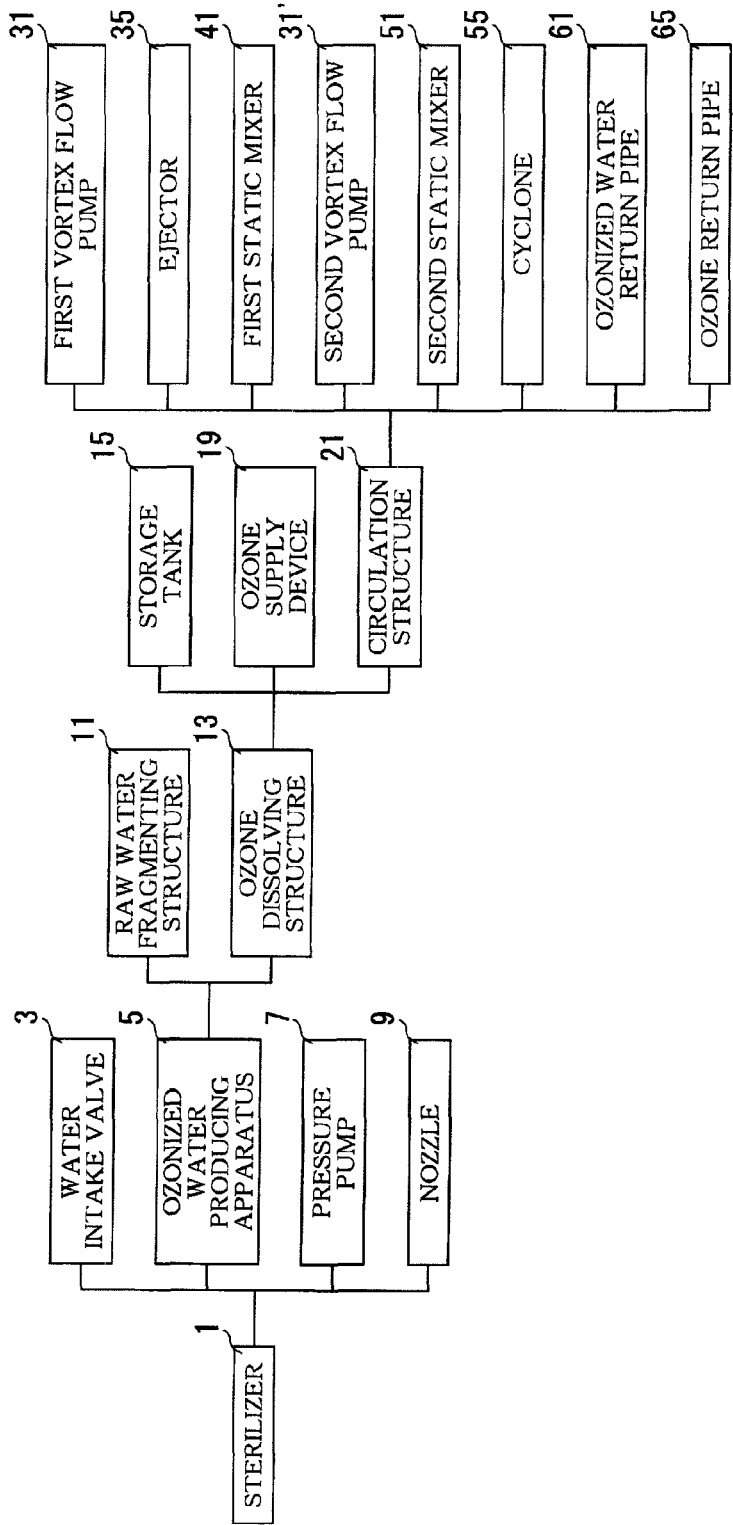
FIG. 4 is a correlation diagram of members and structures constituting the sterilizing apparatus.
Figure 5:
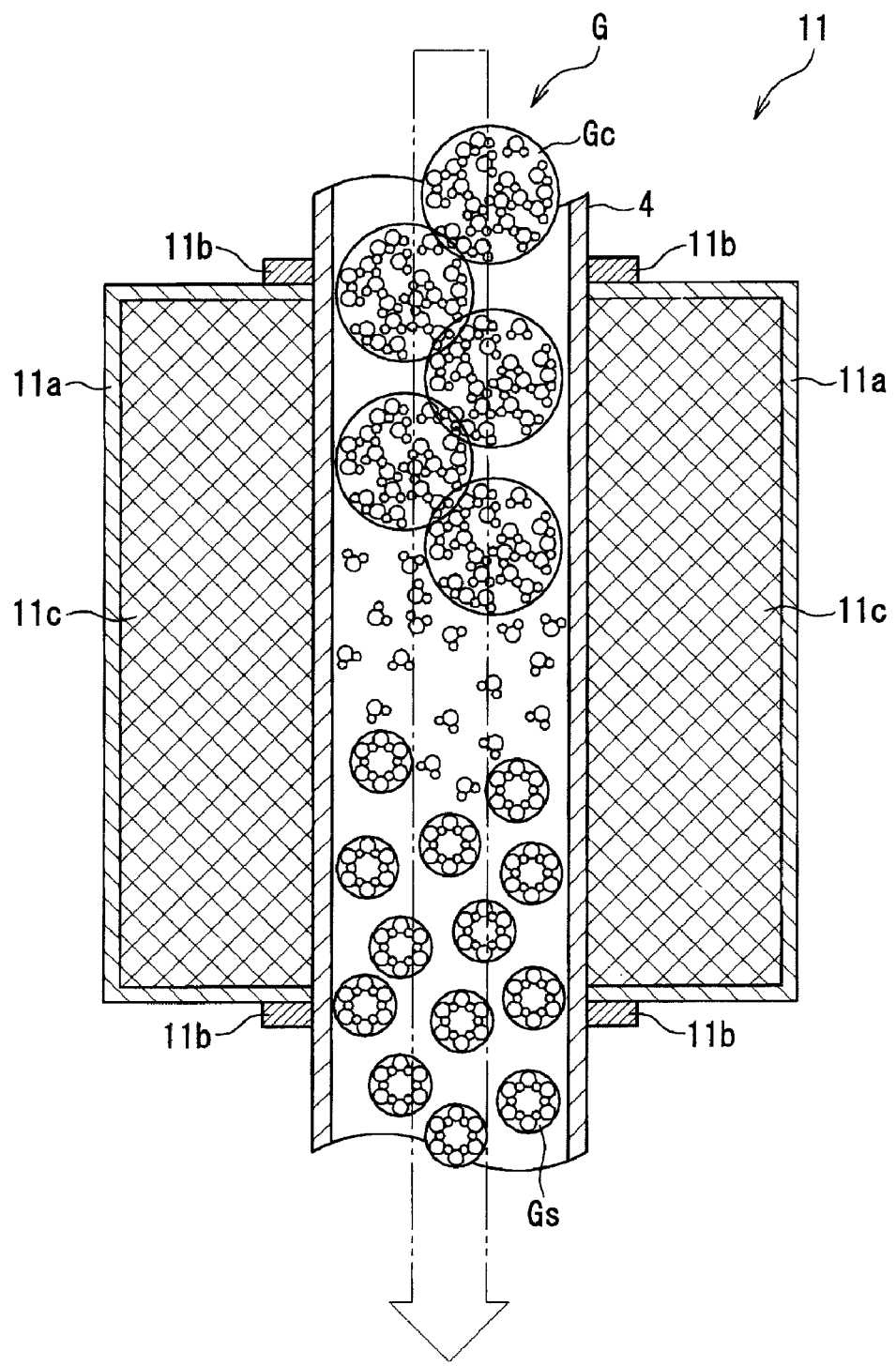
FIG. 5 is a vertical sectional view of a raw water fragmenting structure shown in FIG. 3.
Figure 6:
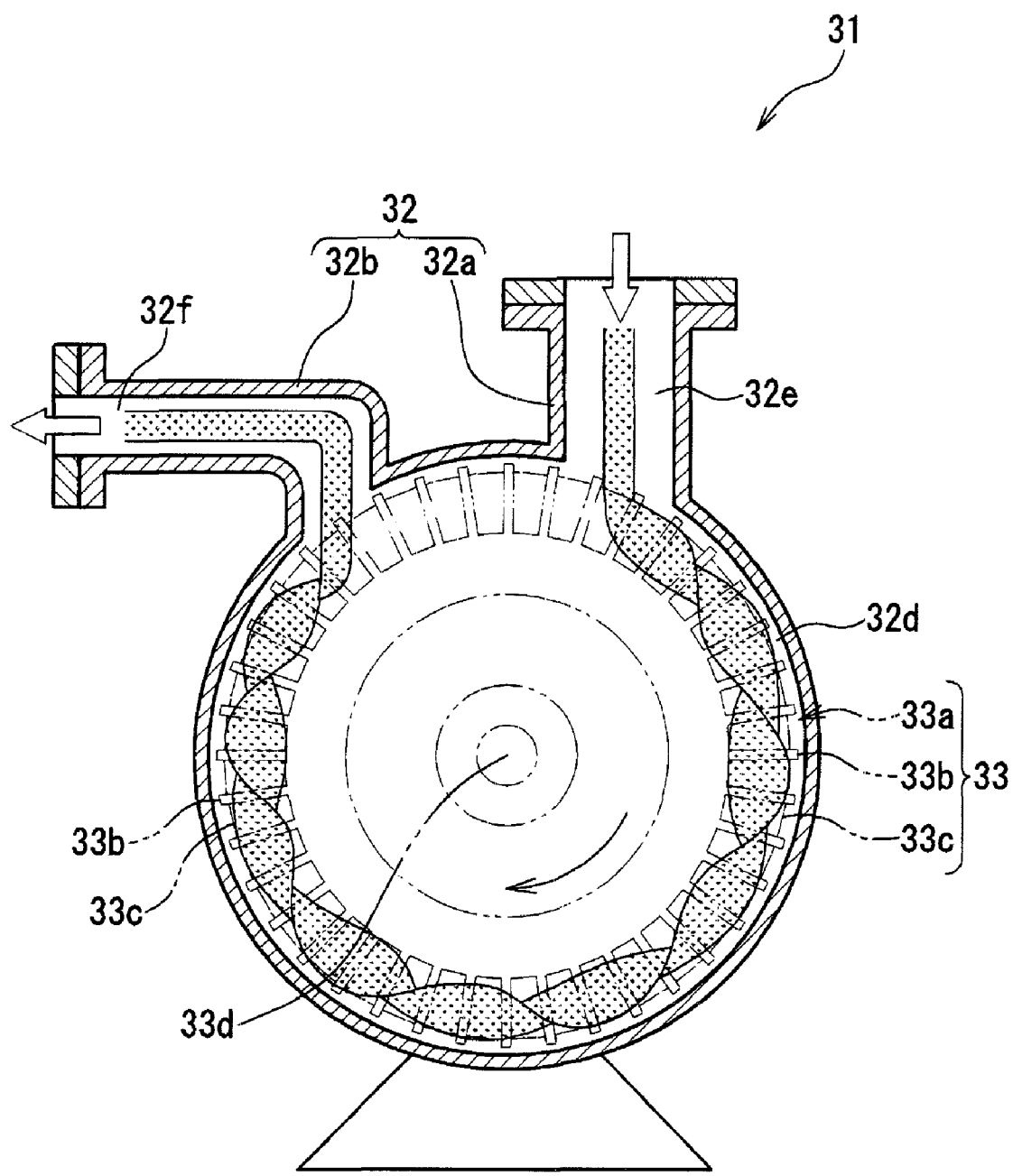
FIG. 6 is a vertical sectional view of a first vortex flow pump.
Figure 7:
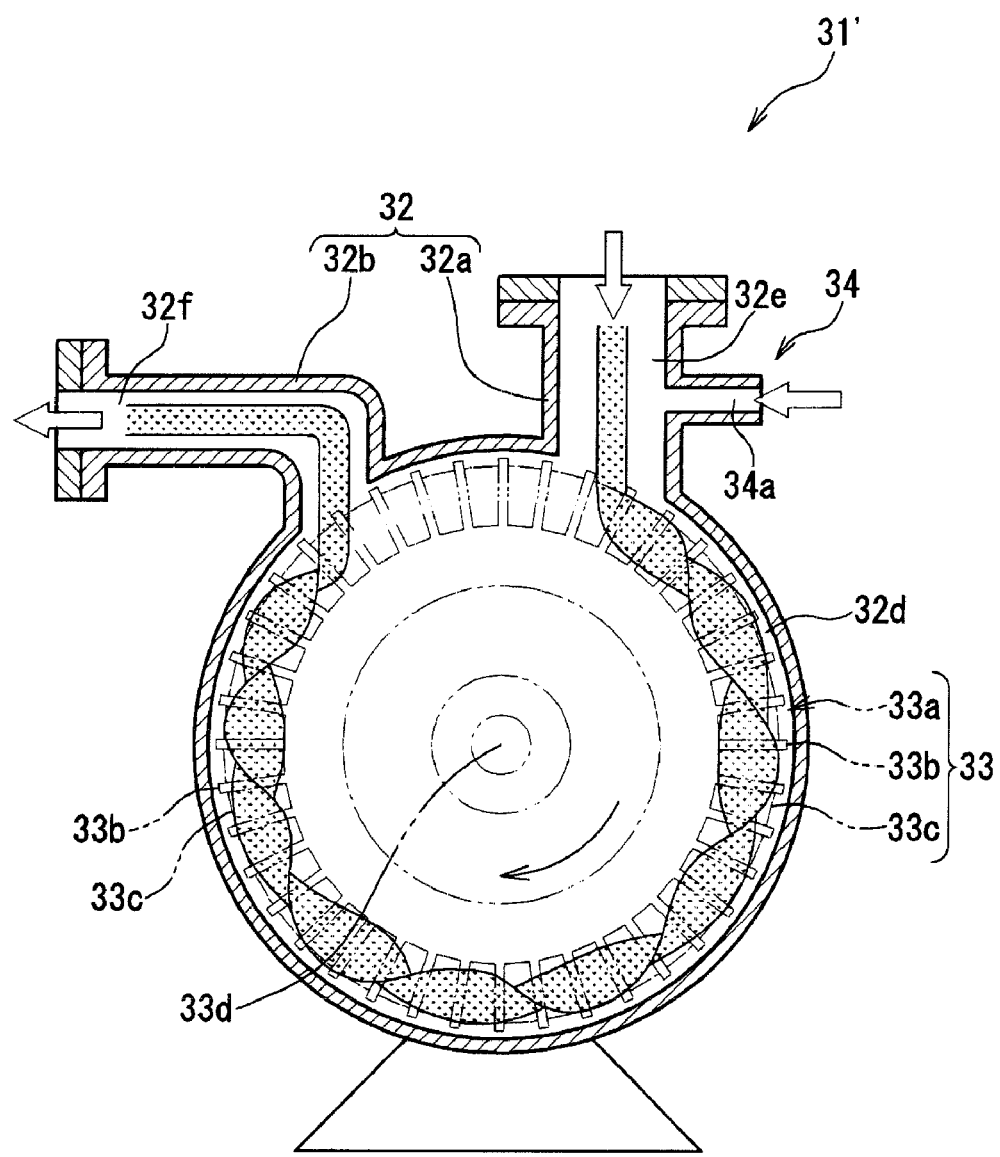
FIG. 7 is a vertical sectional view of a second vortex flow pump.
Figure 8:
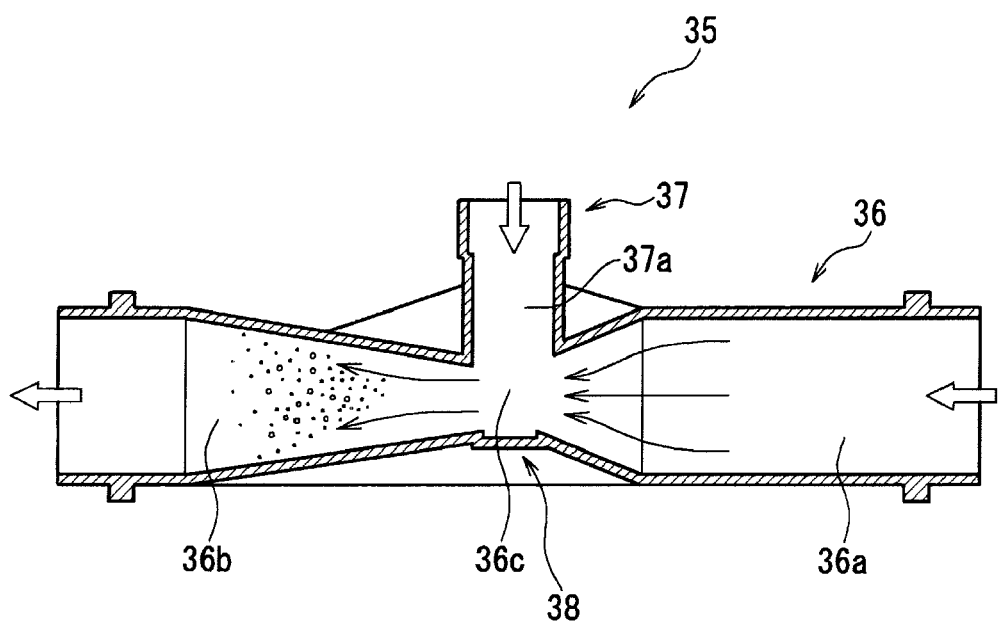
FIG. 8 is a vertical sectional view of an ejector.
Figure 9:
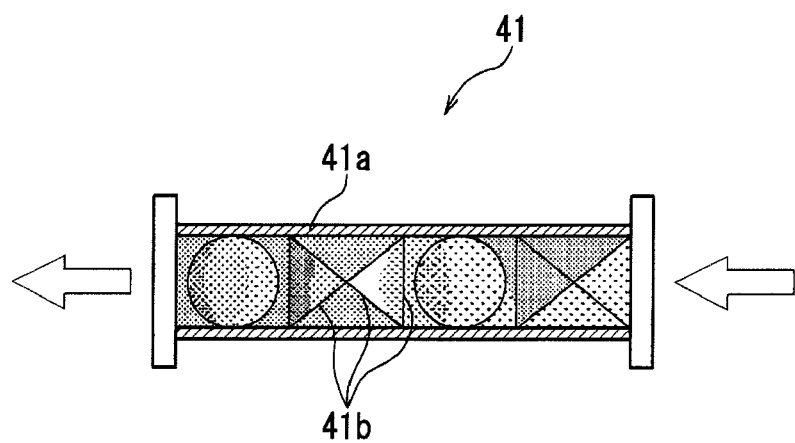
FIG. 9 is a vertical sectional view of a static mixer.
Figure 10:
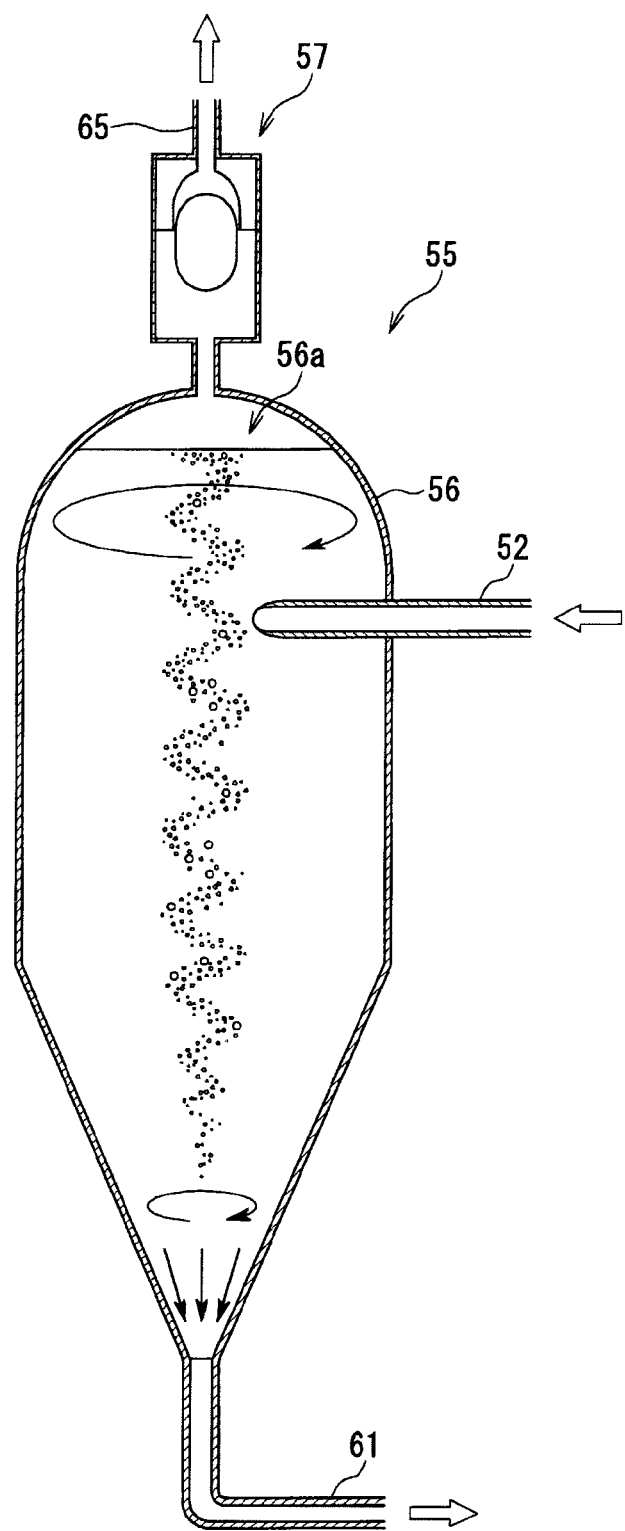
FIG. 10 is a vertical sectional view of a cyclone.
Figure 11:
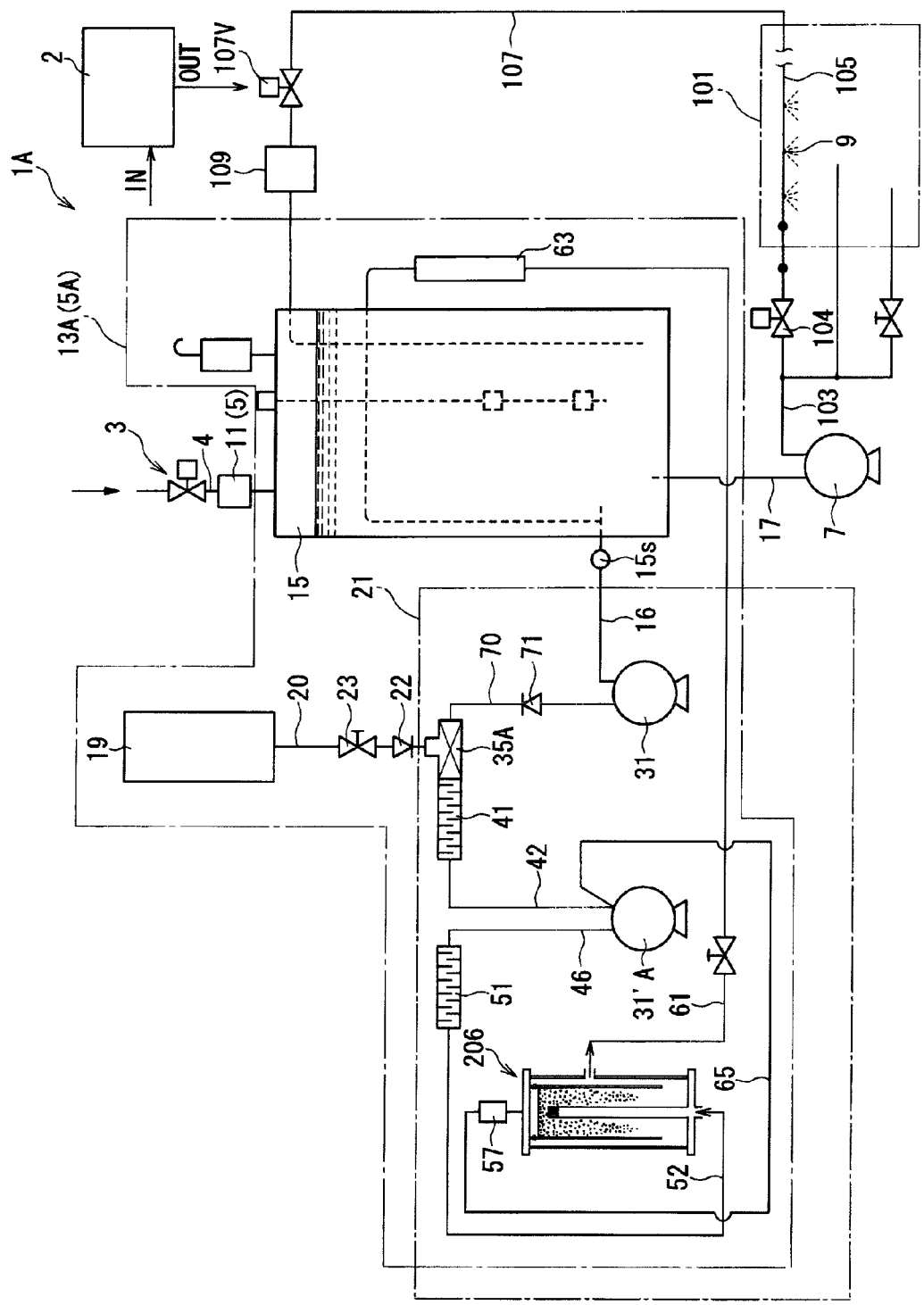
FIG. 11 is a schematic block diagram showing a modified example of the sterilizing apparatus.
Figure 12:
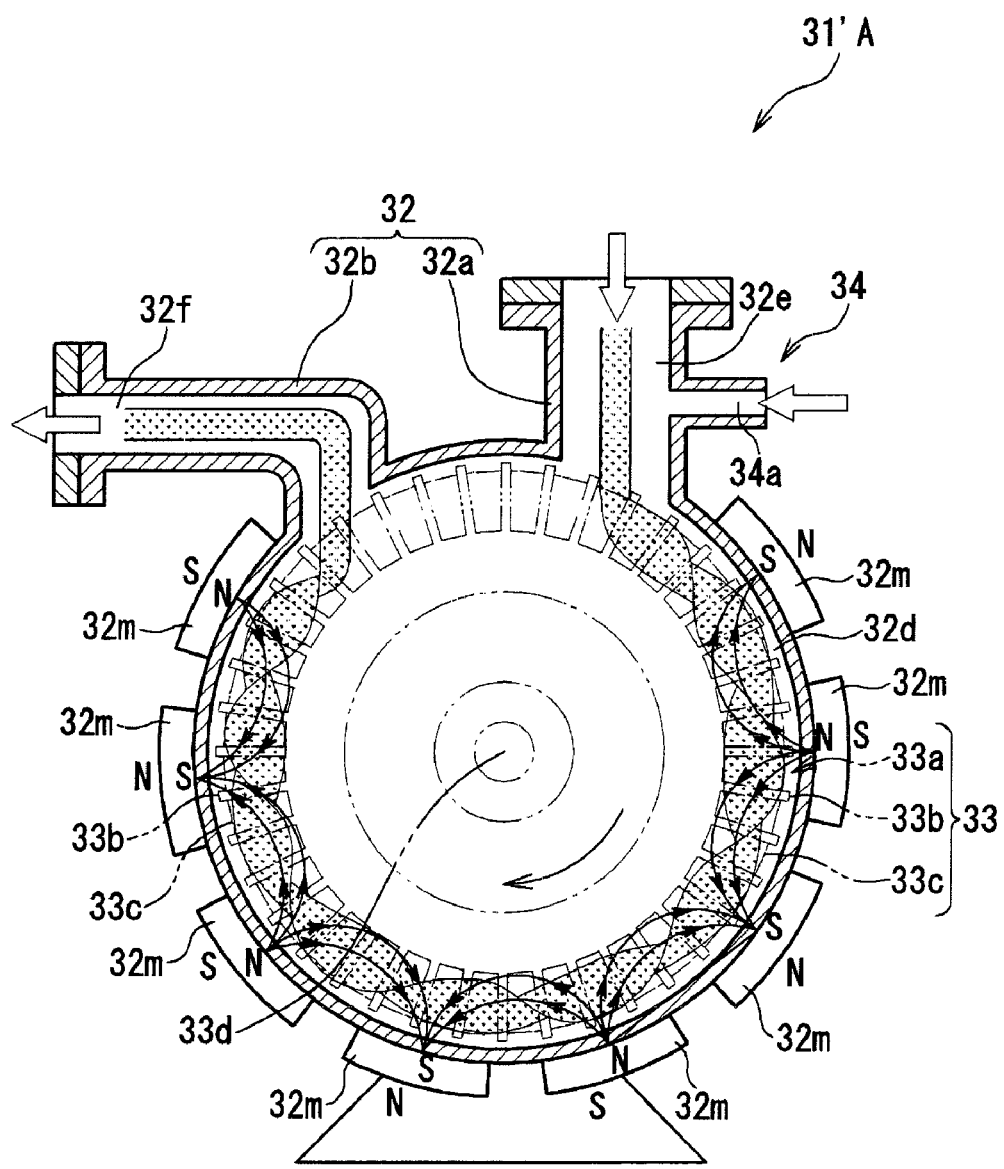
FIG. 12 is a vertical sectional view showing a modified example of the vortex flow pump.
Figure 13:
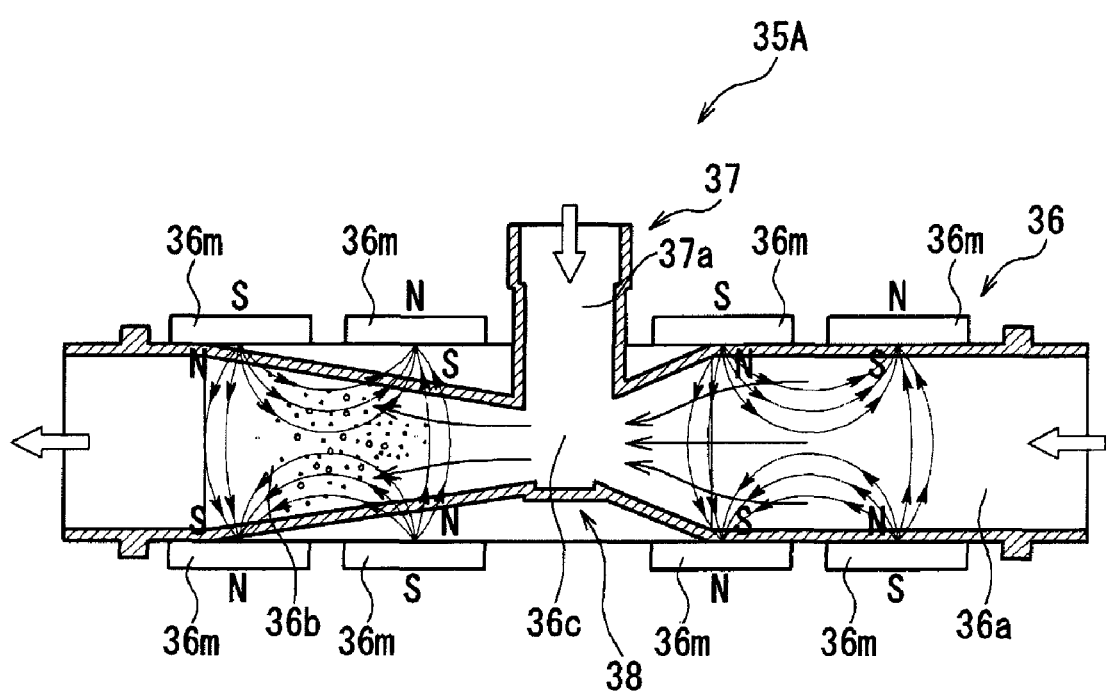
FIG. 13 is a vertical sectional view showing a modified example of the ejector.
Figure 14:
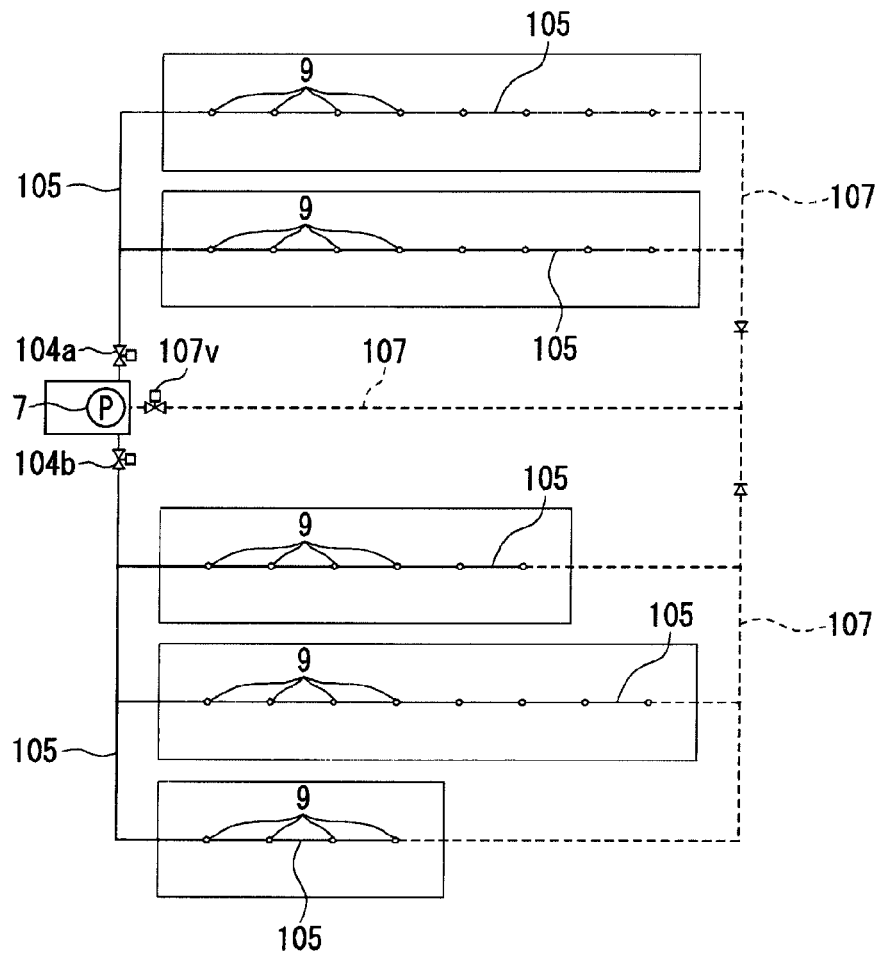
FIG. 14 is a schematic plane view of an ozonized water spray line.
Figure 15:
FIG. 15 is a diagram showing the timing of opening and closing valves.
Figure 15:
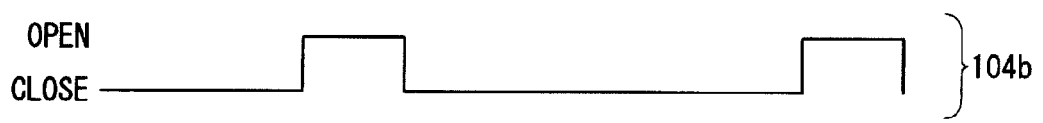
Figure 16:
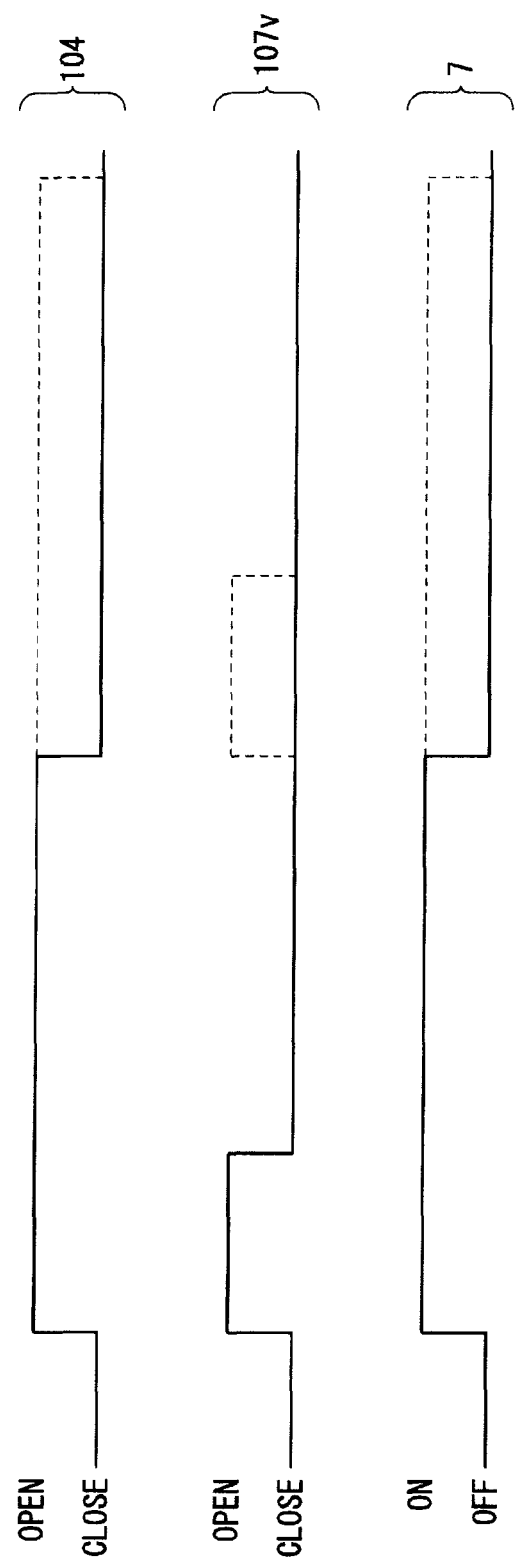
FIG. 16 is a diagram showing the timing of opening and closing valves.
Figure 21:
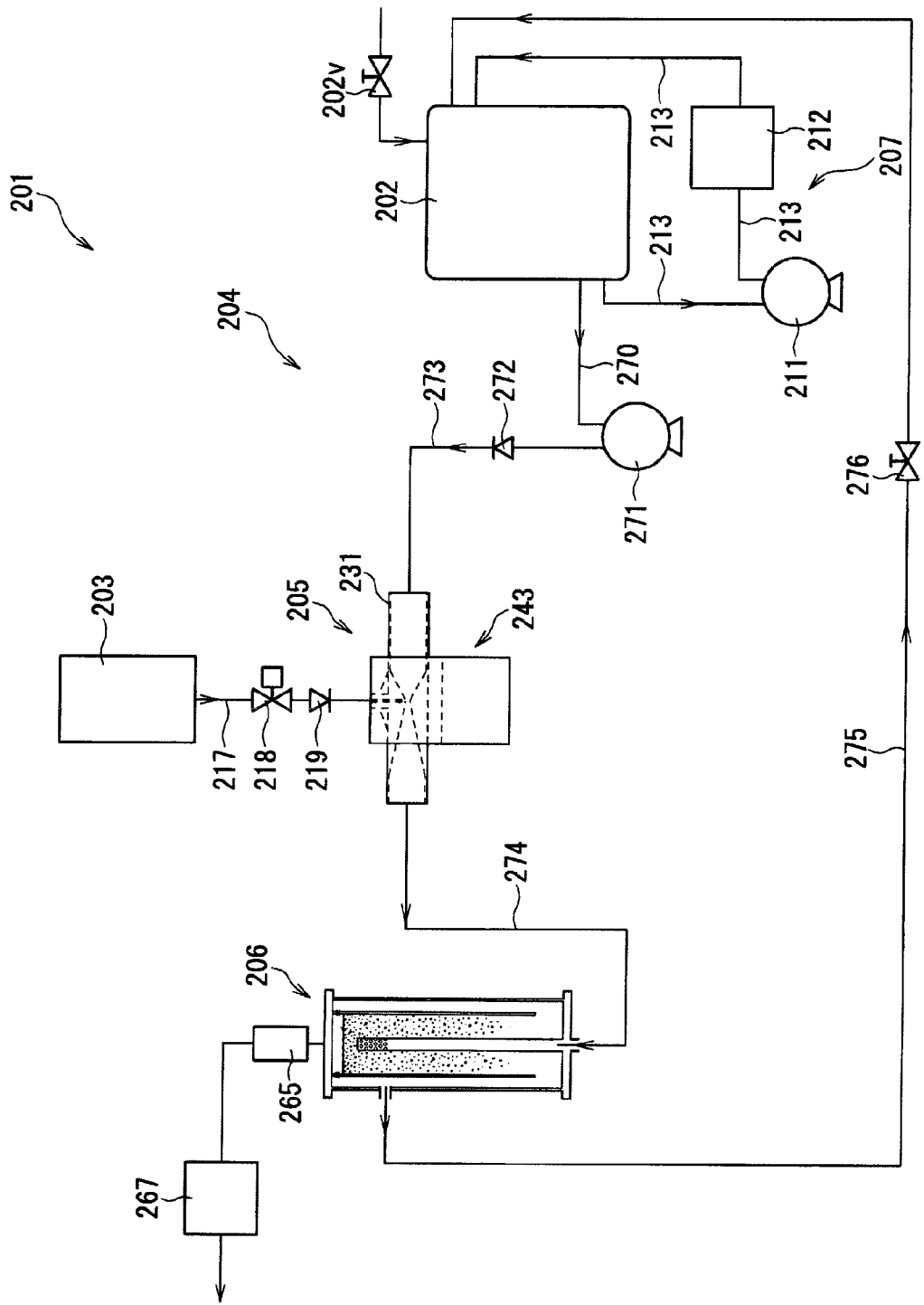
FIG. 21 is a schematic block diagram showing a modified example of the ozonized water producing apparatus which the sterilizing apparatus has.
Figure 22:
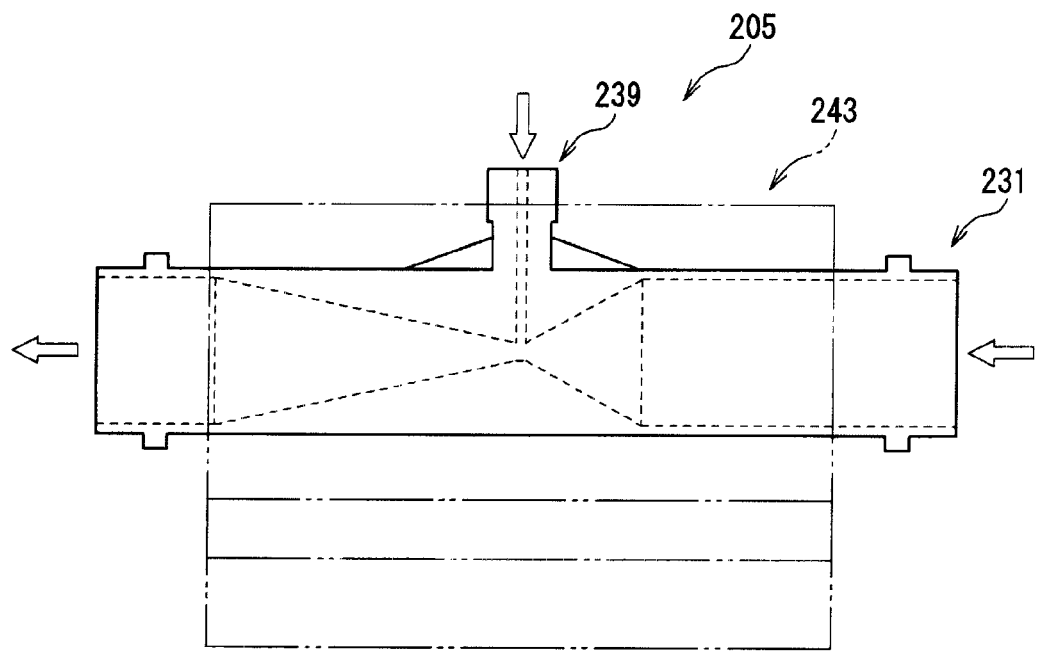
FIG. 22 is a front view of a gas-liquid mixing structure.
Figure 23:
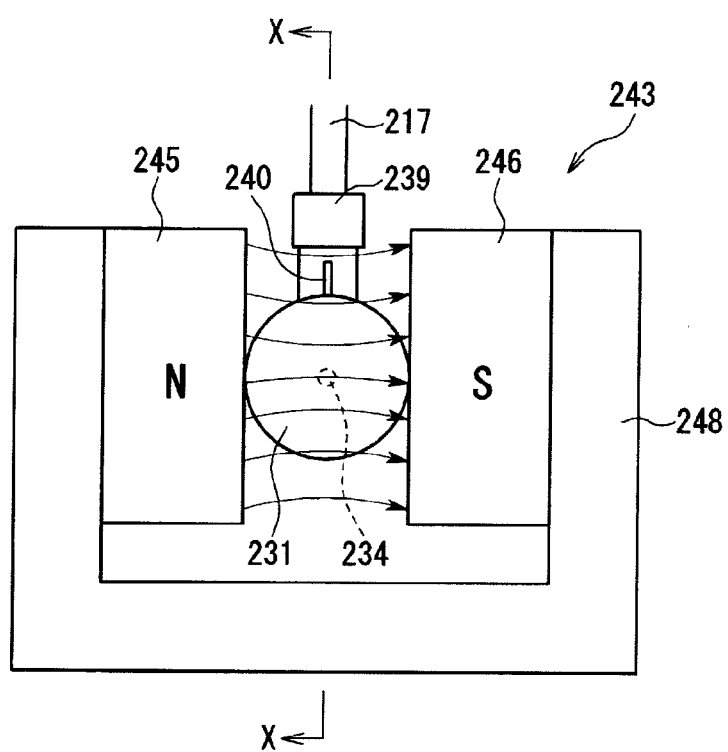
FIG. 23 is a left side view of the gas-liquid mixing structure shown in FIG. 22.
Figure 24:
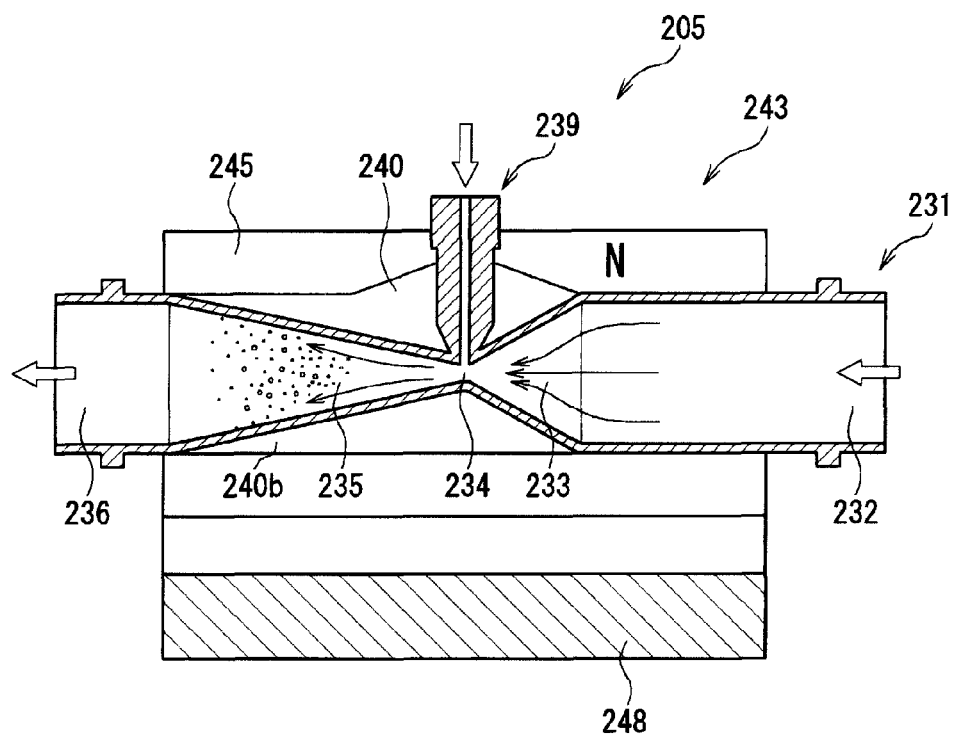
FIG. 24 is a sectional view taken along the X-X line of the gas-liquid mixing structure shown in FIG. 23.
Figure 25:
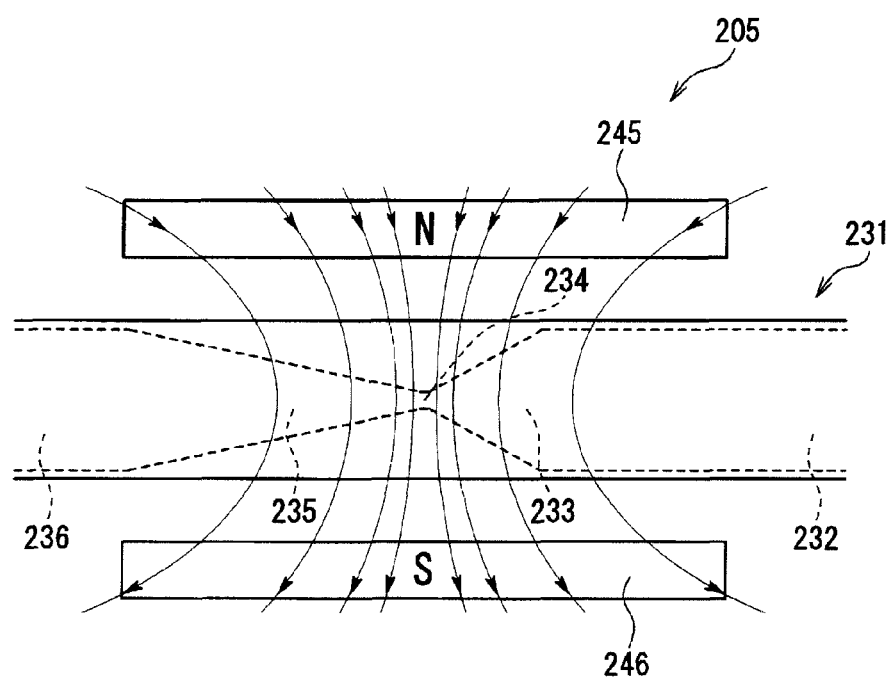
FIG. 25 is a plane view of a partially omitted gas-liquid mixing structure.
Figure 26:
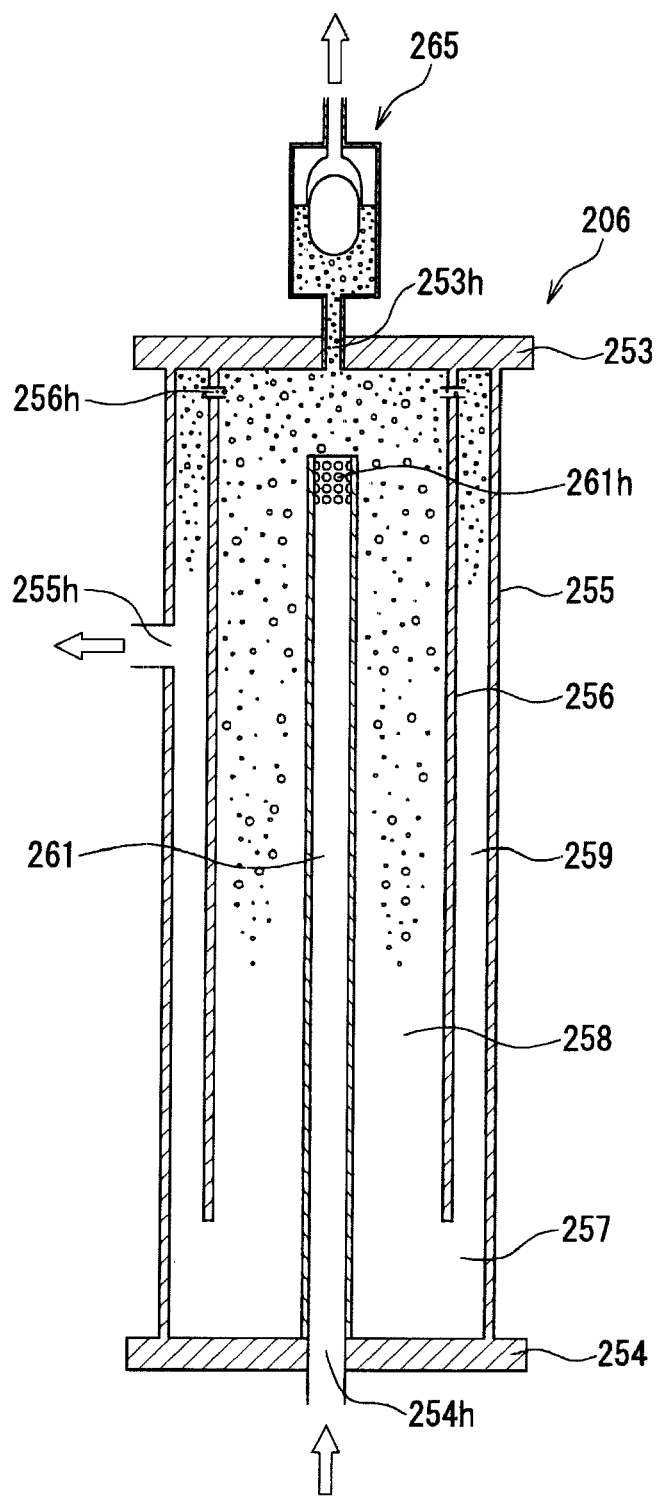
FIG. 26 is a vertical sectional view of a dissolution accelerating tank.
Figure 27:
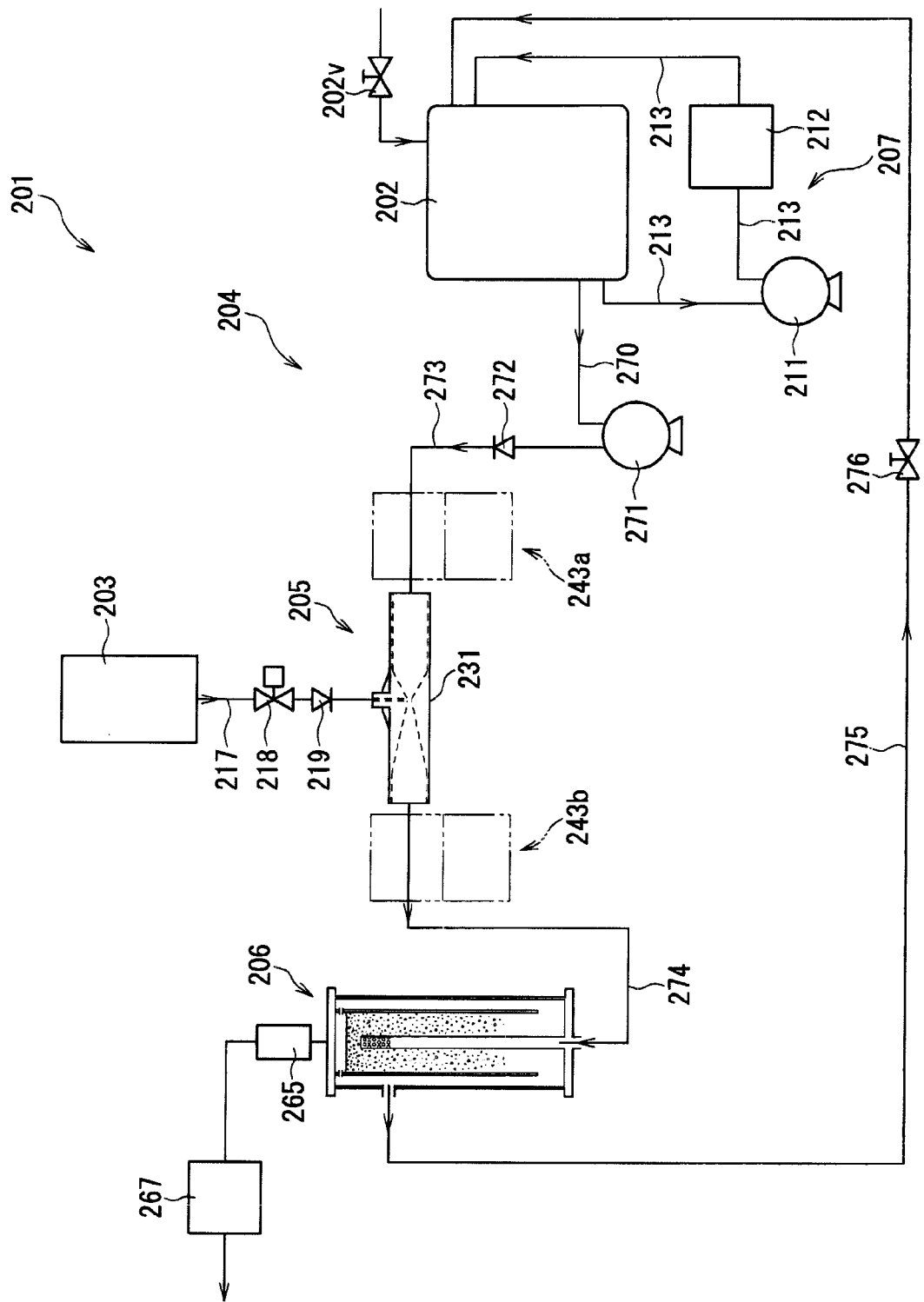
FIG. 27 is a schematic block diagram of the ozonized water producing apparatus for conducting a comparative experiment.
Figure 28:
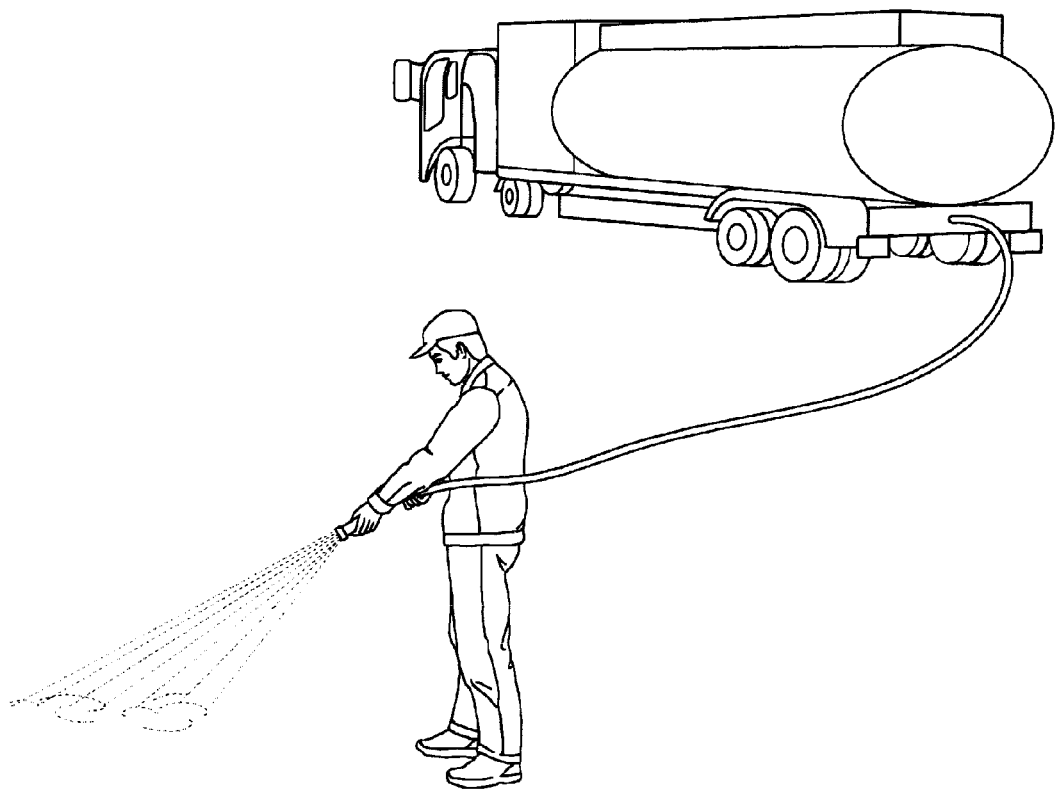
FIG. 28 is a perspective view of the sterilizing apparatus loaded on a conveying structure.

In order to carry out the above described sterilizing method of livestock and/or a livestock barn, in the present embodiment, a sterilizing apparatus for livestock and/or a livestock barn is constituted as follows. Explanation will be made with reference to each of the drawings. FIG. 1 is a plane view of a pigpen. FIG. 2 is a sectional view taken along the line A-A of the pigpen shown in FIG. 1. FIG. 3 is a schematic block diagram of a sterilizing apparatus capable of producing and spraying ozonized water. FIG. 4 is a correlation diagram of members and structures constituting the sterilizing apparatus. FIG. 5 is a vertical sectional view of a raw water fragmenting structure shown in FIG. 3. FIG. 6 is a vertical sectional view of a first vortex flow pump. FIG. 7 is a vertical sectional view of a second vortex flow pump. FIG. 8 is a vertical sectional view of an ejector (gas-liquid mixing structure). FIG. 9 is a vertical sectional view of a static mixer. FIG. 10 is a vertical sectional view of a cyclone. FIG. 11 is a schematic block diagram showing a modified example of the sterilizing apparatus shown in FIG. 3. FIG. 12 is a vertical sectional view showing a modified example of the vortex flow pump. FIG. 13 is a vertical sectional view showing a modified example of the ejector. FIG. 14 is a schematic plane view of an ozonized water spray line. FIGS. 15 and 16 are diagrams showing the timing of opening and closing a valve. FIGS. 17 to 20 are views showing the states of cleaning livestock. FIG. 21 is a schematic block diagram showing a modified example of the ozonized water producing apparatus which the sterilizing apparatus has. FIG. 22 is a front view of a gas-liquid mixing structure. FIG. 23 is a left side view of the gas-liquid mixing structure shown in FIG. 22. FIG. 24 is a sectional view taken along the line X-X of the gas-liquid mixing structure shown in FIG. 23. FIG. 25 is a plane view of a partially omitted gas-liquid mixing structure. FIG. 26 is a vertical sectional view of a dissolution accelerating tank. FIG. 27 is a schematic block diagram of the ozonized water producing apparatus for conducting a comparative experiment. FIG. 28 is a perspective view of the sterilizing apparatus loaded on a conveying structure. In the present embodiment, the sterilizing apparatus is installed in a pigpen for the purpose of sterilizing pigs and/or the pigpen, but it goes without saying that the sterilizing apparatus is applicable to livestock other than pigs and livestock barns other than pigpens.

(Installation of Sterilizing Apparatus)

Explanation will be made based on FIGS. 1 to 3. A pigpen 101 is provided with a water supply line 103 for feeding ozonized water, a spray line 105 for spraying the ozonized water, a return line 107 for returning excessive ozonized water after spraying, and a sterilizing apparatus 1 which will be described later. The ozonized water produced by the sterilizing apparatus 1 is fed by pressure to the spray line 105 through the water supply line 103, and is sprayed by the nozzle 9 (nozzle group 9) connected to the spray line 105 (refer to FIG. 2). The excessive ozonized water after spraying is returned to the sterilizing apparatus 1 through the return line 107. Reference numeral 109 shown in FIG. 3 denotes a filter (strainer) for removing impurities from the return line 107. Reference numeral and character 107V denotes a line valve provided in the return line 107. The line valve 107V is a valve which allows or shuts off movement of the ozonized water in the return line 107. When the later-described pressure pump 7 is operated, if the line valve 107V is opened, the ozonized water returns to a later-described storage tank 15, and if the line valve 107V is closed, the pressure inside the spray line 105 rises and ozonized water is sprayed from the nozzle group 9.

(Schematic Structure of Sterilizing Apparatus)

Explanation will be made based on FIGS. 3 and 4. The sterilizing apparatus 1 is generally constituted of a water intake valve 3, an ozonized water producing structure 5, the pressure pump 7 and the nozzle 9. The water intake valve 3 is an electromagnetic valve and is connected to a supply source of tap water or well water to be raw water. The ozonized water producing apparatus 5 is for producing ozonized water with a high dissolution degree and a high concentration which will be described later. The pressure pump 7 is a pump which pressurizes the produced ozonized water to predetermined pressure for spraying. The ozonized water pressurized by the pressure pump 7 is sprayed via the nozzle 9 (nozzle group 9). The nozzle 9 is treated as singular for convenience of explanation, but may be plural, and in the case of being plural, the nozzles 9 may differ in shape, hole diameter and the like from one another. The sterilizing apparatus 1 is usually used by being installed in a pigpen for which ozonized water spraying is performed, but, it can be constituted to be alternately usable for a plurality of pigpens by being loaded on a vehicle. The sterilizing apparatus 1 includes a controlling device (controller) 2 for controlling the entire system (see FIG. 3).

(Raw Water Fragmenting Structure)

Explanation will be made based on FIGS. 3 and 5. The raw water fragmenting structure 11 is for producing fragmented raw water by fragmenting clusters of the raw water taken in from the water intake valve 3. The raw water fragmenting structure 11 is constituted of a metal casing 11a which is fixed to an outer periphery of a pipeline 4 in which raw water G flows to be concentric with the pipeline 4, a packing 11b, magnets 11c and 11c which are enclosed in the casing 11a. The magnets 11c and 11c are for causing a magnetic force to act on the raw water. The magnetic force of the magnets 11c and 11c is preferably about 1 to 1.5 T (10000 to 15000 gausses), for example. Water like the raw water G is known to form clusters Gc, and the raw water fragmenting structure 11 has the function of fragmenting the clusters Gc of the raw water into clusters Gs by applying energy to the clusters Gc. The clusters Gc and Gs shown in FIG. 3 are shown in the schematic view strictly for the purpose of explanation. They are not necessarily fragmented as shown in the drawing, and the measuring method is not established. However, it is phenomenally obvious that reduction in time to reach the concentration and elongation of the time for ozone to reduce by one-half are possible as shown in Tables 2 and 3 by providing the raw water fragmenting structure 11, and this shows that the speed at which ozone escapes and is decomposed from the ozonized water at the time of pressurization and spray is effectively reduced. Instead of the magnet 11c, a carbon chip group capable of exerting a far infrared radiation effect, an ultrasonic wave generating device capable of applying microvibration and the like can be used. The position at which the raw water fragmenting structure 11 is provided may be at the upstream side or the downstream side of the water intake valve 3. Further, it goes without saying that the pipeline 4 should be constituted of a material which does not interfere with transmission of far infrared rays, a magnetic force and the like, for example, vinyl chloride or the like. The raw water fragmenting structure can be properly provided at the upstream side and/or the downstream side of a vortex flow pump, an ejector and a static mixer as will be described later.

(Ozone Dissolving Structure)

Reference is made to FIGS. 3 and 4. The ozone dissolving structure 13 is constituted of a storage tank 15, an ozone supply device 19, and a circulation structure 21. The storage tank 15 is a tank for storing raw water injected via the water intake valve 3 and/or ozonized water, and has a storage amount of about three tons, for example. The ozone supply structure 19 is the device for producing and supplying ozone, and is not limited in its ozone generation principle or the like at all if only it is capable of supplying a required ozone amount. The circulation structure 21 is for returning the fragmented raw water and/or ozonized water taken out of the storage tank 15 to the storage tank 15 after ozone dissolution, and is constituted of a plurality of members and structures which will be described later.

(Circulation Structure)

Explanation will be made with reference to FIGS. 3, 4 and 5 to 10. The circulation structure 21 is constituted of a first vortex flow pump 31, an ejector 35, a first static mixer 41, a second vortex flow pump 31', a second static mixer 51, a cyclone 55, an ozonized water return pipe 61 and an ozone return pipe 65, and a pipe group connecting the above described respective members. Of the above described constitution, the components except for the ozone return pipe 65 constitute a circulation path which dissolves ozone in the fragmented raw water and/or ozonized water taken out of the storage tank 15 and returns them or it to the storage tank 15, and the ozone return pipe 65 is the circulation path which returns excess ozone taken out of the cyclone 55 to the second vortex flow pump 31'. The respective components will be described hereinafter. It is as described above that fragmenting the clusters of raw water is preferable from the viewpoint of ozone dissolution. Meanwhile, the fragmentation of the clusters is effective ozone dissolving means for not only raw water but also ozonized water. Therefore, it is preferable to provide the same or similar magnets as or to the aforementioned magnet 11c at the suitable spots of the respective members and devices constituting the circulation structure 21 and cause the magnetic force to act on circulating ozonized water.

(Vortex Flow Pump)

Based on FIGS. 3 and 6, the first vortex flow pump will be described. The first vortex flow pump 31 is generally constituted of a thick disc-shaped pump main body 32, an intake part 32a and a discharge part 32b which protrude from the pump main body 32 as part of the pump main body 32, and an impeller 33 which rotates in the pump main body 32. The intake part 32a is connected to the storage tank 15 via a pipeline 16, and the discharge part 32b is connected to the ejector 35 via a check-valve 71 and a pipeline 70. An annular pressure raising passage 32d is formed in the pump main body 32, and an intake path 32e in the intake part 32a and a discharge path 32f in the discharge part 32b are communicated with the pressure raising passage 32d. The impeller 33 includes an impeller main body 33a, a plurality of blade pieces 33b, extending in a radial direction from an outer peripheral portion of the impeller main body 33a, and blade grooves 33c, which open between the respective blade pieces 33b and 33b. The impeller 33 is rotated in the pump main body 32 by a motor (not illustrated) connected to a rotary shaft 33d provided in a center of the impeller main body 33a. Rotation of the impeller 33 causes each of the blade pieces 33b and each of the blade grooves 33c to rotate in the pressure raising passage 32d, and at this time, the raw water (ozonized water) taken into the pressure raising passage 32d via the intake path 32e is force-fed while being stirred and is discharged from the discharge path 32f. Each of the blade pieces 33b feeds the raw water (ozonized water) in each of the blade grooves 33c by pressure while accelerating ozone dissolution by stirring the raw water (ozonized water) in each of the blade grooves 33c by rotation of each of the blade pieces 33b. Specifically, the first vortex flow pump 31 includes the functions of ozone dissolution and pressure feeding.

The second vortex flow pump 31' shown in FIG. 7 has basically the same structure as the first vortex flow pump 31, and only differs from it in the respect that the second vortex flow pump 31' has an ozone return part 34 which the first vortex flow pump 31 does not have. Specifically, the ozone return part 34 is provided at the intake part 32a of the second vortex flow pump 31', and a return path 34a in the ozone return part 34 is communicated with the intake path 32e. Since the members other than the ozone return part 34 do not have any different point as described above, the same reference numerals and characters as those shown in FIG. 6 are used for these members in FIG. 7, and the explanation of them will be omitted. The intake part 32a of the second vortex flow pump 31' is connected to the first static mixer 41 via a pipeline 42, and the discharge part 32b of the same is connected to the second static mixer 51 via a pipeline 46, respectively through the pipelines. One end of the ozone return pipe 65 is connected to the ozone return part 34.

(Ejector)

Reference is made to FIGS. 3 and 8. The ejector 35 is a device for dissolving ozone in fragmented raw water (ozonized water), and is generally constituted of a Venturi tube 36 having a small-diameter portion 38, and an ozone supply portion 37 for supplying ozone in the vicinity of the small-diameter portion 38. Ozone which is sucked from a supply path 37a in the ozone supply portion 37 is mixed into the fragmented raw water (ozonized water) fed by pressure into an inlet path 36a of the Venturi tube 36 by negative pressure which occurs when the raw water passes through a small-diameter path 36c in the small-diameter portion 38, and ozone dissolution is carried out. The ozonized water which passes through the small-diameter path 36c is fed by pressure to outside from an outlet path 36b. Ozone is supplied from the ozone supply device 19 (see FIG. 3) connected to the ozone supply portion 37 via a pipeline 20, a valve 23 and a check-valve 22 which are provided at the pipeline 20.

(Static Mixer)

Explanation will be made based on. FIGS. 3 and 9. The first static mixer 41 and the second static mixer 51 are constituted to have the same structures, and therefore, the structure of the first static mixer 41 will be described here. The first static mixer 41 is constituted of a cylindrical stream tube 41a, and a baffle board group 41b installed in the stream tube 41a. This is a device for mechanically shearing the fragmented raw water (ozonized water) to accelerate dissolution of ozone which is fed at the same time. Pressure-feed of the ozonized water to the first static mixer 41 is performed by the first vortex flow pump 31, and pressure-feed of the ozonized water to the second static mixer 51 is performed by the second vortex flow pump 31'. The discharge side of the second static mixer 51 is connected to the cyclone 55 via a pipeline 52.

(Cyclone)

Reference is made to FIGS. 3 and 10. The cyclone 55 is constituted of a cylindrical enclosed cyclone main body 56, and a gas-liquid separating device 57 connected to an upper portion of the cyclone main body 56. The cyclone main body 56 is constituted to generate a cyclone effect by rotationally flowing the ozonized water, which is fed by pressure from the static mixer 51 through the pipeline 52, inside the cyclone main body 56, and to be capable of accelerating dissolution of ozone. The ozone in the ozonized water rises while rotating, and excess ozone escaping from the ozonized water comes out to an upper space 56a of the cyclone main body 56 and is fed to the ozone return pipe 65 via the gas-liquid separating device 57. The ozone in the ozone return pipe 65 is sucked by the negative pressure of the second vortex flow pump 31' and is mixed into ozonized water again.

(Pressure Pump and Nozzle)

As for the pressure pump 7 and the nozzle 9 (nozzle group), as described in the explanation of the sterilizing method, the average particle size of the ozonized water when sprayed is suitably set in the range of 40 to below 200 μm or of 200 to 1000 μm in accordance with the use purpose or the like. This is for the reason that since the pressure of the ozonized water to be sprayed needs to be set in the above described range of 0.2 to 0.8 MPa, in order to spray the ozonized water in such a pressure range, the average particle size has a fixed limit, and this is also for the reason that the ozonized water of sprayed into such a particle size from the nozzle is efficiently spread to livestock and the barn, and has less risk of piggy or the like catching a cold. The ozonized water taken out of the storage tank 15 via a pipeline 17 is sucked into the pressure pump 7 from an intake port, where it is pressurized to be fed by pressure to a water supply line 103 from a discharge port, and it is further fed by pressure to a spray line 105 via an electromagnetic valve 104. The ozonized water which is fed by pressure from one side of the spray line 105 in this way is partially sprayed from the nozzle 9 as described above, and the excess ozonized water remaining after the spraying can be returned to the storage tank 15 via a return line 107 communicating with the other side of the spray line 105. The electromagnetic valve 104 is a valve for stopping supply of the ozonized water to the spray line 105, but supply and shutoff of it are controllable by only operation and stoppage of the pressure pump 7, and therefore, the electromagnetic valve 104 can be omitted.

(Operation of the Sterilizing Apparatus)

Reference is made to FIG. 3. Tap water (raw water) taken in through the water intake valve 3 is poured into the storage tank 15 through the raw water fragmenting structure 11. At this time, the clusters of the poured tap water is fragmented by the far infrared radiation action of the raw water fragmenting structure 11, and the tap water becomes fragmented raw water. The fragmented raw water taken out of the storage tank 15 by the first vortex flow pump 31 is fed by pressure to the ejector 35 by the first vortex flow pump. Ozone is supplied into the ejector 35 by the ozone supply device 19, and ozone dissolution into the fragmented raw water is performed. The ozonized water which has passed through the ejector 35 is accelerated in ozone dissolution by the first static mixer 41, and is fed by pressure to the second static mixer 51 by the second vortex flow pump 31'. The ozonized water which is further accelerated in ozone dissolution by the second static mixer 51 is poured into the cyclone 55. The ozonized water in the cyclone 55 is rotationally flown and is further accelerated in ozone dissolution by the cyclone effect. The ozonized water taken out of the cyclone 55 is returned to the storage tank 15 through the ozonized water return pipe 61. At this point of time, the fragmented raw water poured into the storage tank 15 becomes ozonized water. The above described process is repeatedly carried out until the ozone concentration of the ozonized water stored in the storage tank 15 becomes a predetermined concentration (in concrete, 3 to 20 ppm). The ozonized water which reaches the predetermined concentration is taken out of the storage tank 15 and fed by pressure by the pressure pump 7 and is sprayed from the nozzle group 9.

The ozonized water remaining after the spraying is returned to the storage tank 15 through a filter 109 and is subjected to reuse as described above.

In this case, the first vortex flow pump 31 and the second vortex flow pump 31' mix the water by assisting each other with pressure. Specifically, the first vortex flow pump 31 and the second vortex flow pump 31' basically have the same structures and capacities, but by assisting each other with pressure, the discharge side of the second vortex flow pump 31' is at a pressure slightly higher than the discharge side of the first vortex flow pump 31 (the ozone return pipe 65 which returns to the storage tank 15 through the gas-liquid separating device 57 and the cyclone 55 are the same pressure), but excess ozone is returned to the second vortex flow pump 31' by the negative pressure of the second vortex flow pump 31'. Namely, occurrence of excess ozone is extremely a little, and thereby, burden on the ozone supply structure 19 can be made small.

(Modified Example of the Sterilizing Apparatus)

A sterilizing apparatus 1A which is a modified example of the aforementioned sterilizing apparatus 1 will be described with reference to FIGS. 11 to 13. The sterilizing apparatus 1A basically has a common constitution to the sterilizing apparatus 1, and they mainly differ from each other in the respect that the sterilizing apparatus 1A has a cooling device 63 which the sterilizing apparatus 1 does not have, the respect that the shape of the cyclone 55 and the shape of a cyclone 55A which they have differ from each other, the respect that a second vortex flow pump 31'A has a magnet 32m which the second vortex flow pump 31' does not have, and the respect that an ejector 35A has a magnet 36m which the ejector 35 does not have. Though not illustrated, the static mixer 51 provided with a magnet can be adopted.

Based on FIG. 12, the respect that the second vortex flow pump 31'A according to this modified example differs from the second vortex flow pump 31' according to the present embodiment will be described. As for the points common to them, the reference numerals and characters used for the second vortex flow pump 31' are used in FIG. 12, and the explanation of the points will be omitted. Specifically, on the outer side of the pump main body 32 which the second vortex flow pump 31'A has, a plurality of magnets 32m, are mounted at predetermined spaces along the rotational direction of the impeller 33 as described above. Each of the magnets 32m is for fragmenting the clusters by causing the magnetic force to act on the ozonized water in the pump main body 32, and thereby enhancing the ozone dissolution degree. Accordingly, the pump main body 32 is formed of a material which can transmit the magnetic force of each of the magnets 32m (for example, a metal such as stainless steel and a synthetic resin which are capable of transmitting a magnetic force). Though not illustrated, magnets may be provided at the first vortex flow pump 31 as in the second vortex flow pump 31'A.

Based on FIG. 13, the respect in which the ejector 35A according to this modified example differs from the ejector 35 according to the present embodiment will be described. As for the points common to them, the same reference numerals and characters as those used in the ejector 35 are used in FIG. 13, and the explanation of the points will be omitted. Specifically, on the outer side of the Venturi tube 36 of the ejector 35A, a plurality of magnets 36m, are mounted at predetermined spaces from each other along the longitudinal direction as described above. Each of the magnets 36m is for fragmenting clusters by causing the magnetic force to act on the ozonized water in the Venturi tube 36, and thereby, enhancing the ozone dissolution degree. Therefore, the Venturi tube 36 is formed of a material which can transmit the magnetic force of each of the magnets 36m (for example, a metal such as stainless steel and a synthetic resin capable of transmitting a magnetic force). As the device for mixing gas and liquid, a device of a dissolving membrane method (not illustrated) in which hollow fiber type permeation membranes which ozone gas can pass through are bundled in a membrane module, and water is passed inside the permeation membranes and mixed with ozone can be used instead of the ejector. The clusters of water can be fragmented by providing magnets in the device of the dissolving membrane method.

Referring to FIGS. 14 to 16, the timing of spraying the ozonized water will be described. Of the members shown in FIG. 14, the same members as those shown in FIG. 1 are assigned with the same reference numerals and characters as those used in FIG. 1. In FIG. 14, a circulation route in which the ozonized water stored in the storage tank 15 outside the drawing (refer to FIGS. 3 and 11) is fed by pressure to the spray lines 105, . . . via electromagnetic valves 104a and 104b by the pressure pump 7, and the ozonized water which passes through the spray lines 105, is returned to the storage tank via the return lines 107, is formed. The electromagnetic valves 104a and 104b are for making two circulation routes usable alternately by alternately opening and closing them as shown in FIG. 15. Here, by closing the line valve 107V which is in an open state so far, circulation of the ozonized water in any of the above described circulation routes is allowed at the time of its opening, and at the time of its closing, return of the ozonized water is stopped to increase the pressure of the ozonized water in the spray lines 105 . . . . Specifically, by the pressure pump 7 feeding the ozonized water by pressure in the sate in which the return of the ozonized water is stopped, the ozonized water in the spray lines 105, . . . is pressurized. When the pressure of the ozonized water reaches the pressure high enough to allow the nozzle group 9 to spray the ozonized water, ozonized water spraying is performed. When the line valve 107V is opened again, the pressure of the ozonized water in the spray lines 105, . . . reduces and the ozonized water spraying is stopped. At this time, the ozonized water is not sprayed from the nozzle group 9, but passes in the spray lines and is returned to the storage tank. If the pressure pump 7 is stopped, circulation of the ozonized water is stopped.

Here, the case where the ozonized water circulation is stopped and the ozonized water is circulated again, for example, the case where the ozonized water was sprayed in the morning of a certain day, and thereafter, the ozonized water is circulated again for spraying the ozonized water in the afternoon on the same day is assumed. In this case, the temperature of the ozonized water inside the spray lines 105, . . . and the return lines 107, . . . is raised by sunlight or the like especially in the summer season, and ozone is in the escaping state or hardly kept dissolved to escape easily at the time of spraying or the dissolved ozone decomposes by itself by heating to be unable to keep a sufficient concentration in many cases. Thus, the line valve 107V is brought into an open state (specifically, a spraying disabled state), and the pressure pump 7 is operated for circulating the ozonized water again. Subsequently, after the ozonized water which flows out of the storage tank after operation of the pressure pump 7 passes through the nozzle 9 which the ozonized water reaches the latest of the respective nozzles 9 constituting the above described nozzle group 9, the line valve 107V is closed so that the above described ozonized water is sprayed from the nozzle group 9. The control device 2 of the sterilizing apparatus 1 (1A) is constituted so that the ozonized water spraying is performed in the above described timing. This is because in the ozonized water left in the line, ozone may escape as described above, and even if such degassed ozonized water is sprayed, effective sterilizing cannot be performed. A time chart shown in FIG. 16 shows the above described spraying timing.

Referring to FIGS. 17 to 20, a preferable spraying method of the ozonized water to livestock will be described. First, as shown in FIG. 17, the ozonized water is directly sprayed to the pubic region of livestock. This is because sterilizing a pubic region is extremely effective in keeping health of livestock since saprophytic bacteria easily propagate in pubic regions in both male and female of livestock. A plurality of domestic animals are let into a sterilizing cage 150 capable of accommodating them to stand side by side in the same orientation, and ozonized water spraying is intensively performed for a pubic region of each domestic animals through a nozzle 153. This is because this sterilizing method is convenient since even if the livestock moves violently, a livestock body does not have to be moved greatly, and a number of domestic animals can be sterilized at the same time only by directing the nozzle 153 to the left and the right.

Figure 19:
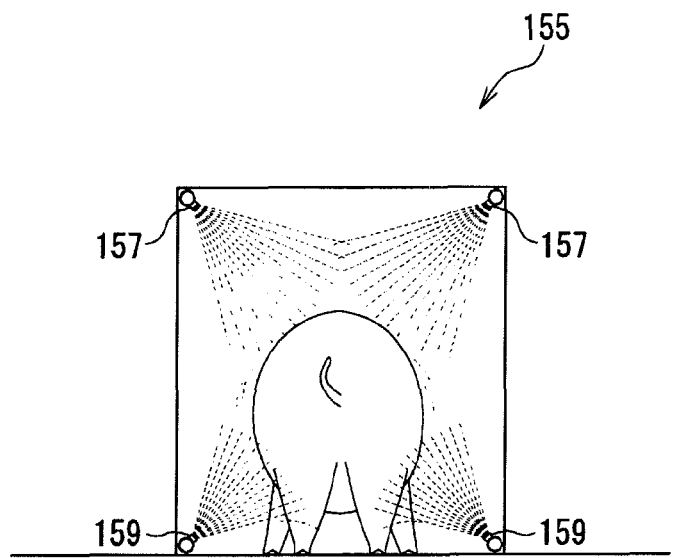
FIG. 19 is a view showing the state of washing the livestock.
Figure 20:
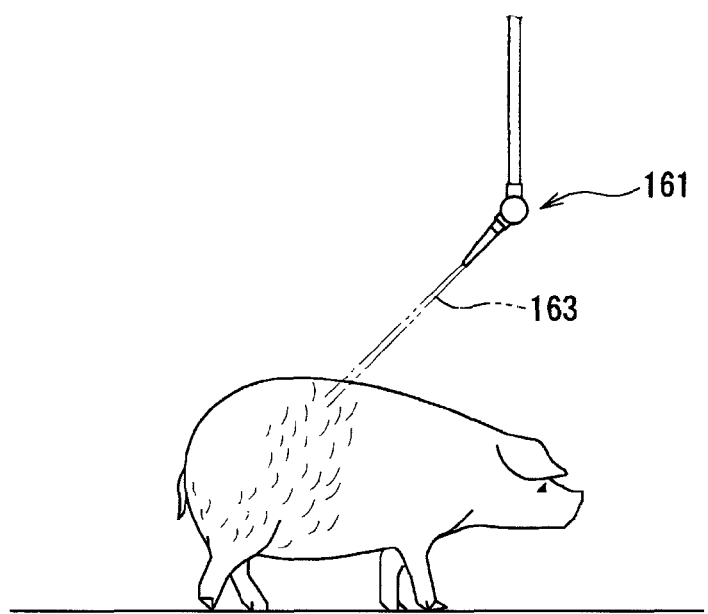
FIG. 20 is a view showing the state of washing the livestock.

Another preferable sterilizing method is shown in FIGS. 18 to 20. Here, livestock is sterilized while it is moved in a column. For example, a passage 155 between a livestock barn and the other livestock barn is constituted so that the livestock can move in a column, nozzles 157, 157, 159 and 159 are installed at the positions higher and lower than the livestock in the passage 155, so that the ozonized water can be sprayed from them. Reference numeral 165 denotes a ventilation fan provided in the passage 155, and reference numeral 1 (1A) denotes a sterilizing apparatus. After ozonized spraying, dewatering by air blow is preferably performed. This is for preventing the livestock which finishes moving from being drenched. This is extremely important for preventing the livestock from catching a cold or the like. Air blow is performed through an air nozzle 161. Reference numeral 163 denotes air which is blown. Air blow is effective when it is performed for the livestock with an angle α of 20 to 70 degrees (see FIG. 18) with respect to the horizontality from above the front with respect to the livestock. This is because the dewatering effect can be enhanced by substantially matching the hair lying angle of the livestock and the blow angle.

It is strongly desired to sterilize livestock facilities (for example, a livestock barn, equipment such as feeders and cages), livestock tools (scoops for conveying feces and urine, clothing and shoes of feeding workers, vehicles coming in and going out of the feeding site), and the like at the same time by using the ozonized water which sterilizes the livestock. By sterilizing the livestock facilities, livestock tools and the like at the same time, the hygienic state of livestock can be actually kept.

(Modified Example of Ozonized Water Producing Apparatus)

Referring to FIGS. 21 to 26, a modified example of the ozonized water producing apparatus 5 included by the sterilizing apparatus shown in FIG. 1 or 11 will be described. An ozonized water producing apparatus 201 according to the modified example is generally constituted of a storage tank 202, an ozone supply structure 203 for generating and supplying ozone, a circulation structure 204 for returning water to be treated taken out of the storage tank 202 to the storage tank 202, a gas-liquid mixing structure 205 and the dissolution accelerating tank 206 which are provided halfway in the circulation structure 204, and a temperature keeping structure 207 annexed to the storage tank 202, as shown in FIG. 21. In the following description, for convenience of explanation, the circulation structure 204 will be finally described after the storage tank 202, the temperature keeping structure 207, the ozone supply structure 203, the gas-liquid mixing structure 205 and the dissolution accelerating tank 206 are described.

(Structure of Storage Tank and its Periphery)

As shown in FIG. 21, the storage tank 202 is constituted so that raw water as water to be treated can be poured into the storage tank 202 through a water intake valve 202v. The storage tank 202 is for storing the raw water which is taken in, and water to be treated (ozonized water) which is circulated through the circulation structure 204 which will be described later. The water to be treated stored in the storage tank 202 is kept at a temperature in the range of, for example, 5 to 15° C. by the temperature keeping structure 207. The reason of setting the temperature in the above described range is that the temperature in this range is suitable for efficiently performing ozone dissolution and preventing the dissolved ozone from easily escaping. The temperature keeping structure 207 is generally constituted of a pump 211 for taking out the water to be treated from the storage tank 202, and a cooler 212 for cooling the water to be treated which is taken out. The storage tank 202 and the pump 211, the pump 211 and the cooler 212, and the cooler 212 and the storage tank 202 are connected by a pipeline 213 in which the water to be treated is passed. According to the above described constitution, the water to be treated (raw water and/or ozonized water) stored in the storage tank 202 is taken out of the storage tank 202 by the action of the pump 211 and is fed to the cooler 212. The cooler 212 cools the water to be treated, which is fed thereto, to a temperature in a predetermined range and returns the water to the storage tank 202. The pump 211 operates only when the temperature of the water to be treated in the storage tank 202 which is measured by a thermometer outside the drawing exceeds the predetermined range and cooling is required. The reason of providing the storage tank 202 is to enable the above described cooling by temporarily storing the water to be treated, and to place the water to be treated in a stable state, thereby accelerating ozone dissolution in the water to be treated by the action of aging assimilation. When the water to be treated has the possibility of being frozen in a cold district or the like, for example, the water to be treated can be adapted to be heated by using a heater instead of the above described cooler, or with the above described cooler.

(Ozone Supply Structure)

The ozone supply structure 203 is a device for generating and supplying ozone. The ozone generation principle or the like on which the ozone supply structure 203 works is not limited, if only it can supply a required ozone amount. The ozone generated by the ozone supply structure 203 is supplied to the gas-liquid mixing structure 205 through an electromagnetic valve 218 and a check-valve 219 which are provided halfway in an ozone supply pipe 217.

(Gas-Liquid Mixing Structure)

The details of the gas-liquid mixing structure 205 will be described with reference to FIGS. 21 to 25. The gas-liquid mixing structure 205 is generally constituted of a Venturi tube 231, an ozone supply pipe 239 and a magnetic circuit 243. The Venturi tube 231 has a pipe-shaped appearance for passing the water to be treated fed from the upstream side (the right side of FIG. 24 as one faces it) to the downstream side (the left side of FIG. 24 as one faces it) (refer to FIG. 22). A hollow part which penetrates through the Venturi tube 231 in the longitudinal direction communicates with an upstream side large path 232, a contracting inclined path 233, a small-diameter path 234, an opening inclined path 235 and a downstream side large path 236 in this sequence from the upstream side to the downstream side. The upstream side large path 232 is connected to the small-diameter path 234 via the contracting inclined path 233 inclined in the contracting direction at a steep angle of about 50 degrees with respect to the axial direction, and thereafter, is opened at a gentle angle of about 30 degrees with respect to the same axial direction by the opening inclined path 235. The opening inclined path 235 is connected to the downstream side large path 236 having the same outside diameter as the upstream side large path 232. On the other hand, to the small-diameter path 234, an open end of the ozone supply pipe 239 is faced. The ozone supply pipe 217 which communicates with the ozone supply structure 203 is connected to a supply end of the ozone supply pipe 239. The inside of the small-diameter path 234, or the vicinity of it is under vacuum or in the state close to a vacuum due to pressure change of the water to be treated, and therefore, ozone reaching the open end is sucked and diffused into the water to be treated being a turbulent flow. Reference numeral 240 denotes a rib for reinforcing the region between the Venturi tube 231 and the ozone supply pipe 239.

The magnetic circuit 243 is fixed to the Venturi tube 231 with a screw (not illustrated). The magnetic circuit 243 is constituted of one magnet piece 245 and the other magnet piece 246 which are opposed to each other with the Venturi tube 231 therebetween, and a connecting member 248 U-shaped in section (refer to FIG. 23) which connects the one magnet piece 245 and the other magnet piece 246, and has the function of mounting the magnet pieces to the Venturi tube 231. The magnet piece 245 and the magnet piece 246 are preferably arranged so that the largest number of magnetic forces (magnetic field) pass through the small-diameter path 234 (shown by the broken line in FIG. 25. Refer to FIG. 24 in combination) and/or its vicinity (especially, the downstream side). However, concentration of the magnetic forces on only the small-diameter path 234 is actually accompanied by technical difficulties, and therefore, the magnetic forces are passed through both the small-diameter path 234 and the vicinity of the small-diameter path 234. This is because it is conceivable that ozone can be dissolved in the water to be treated with the highest efficiency by causing the magnetic force to act on both the water to be treated and ozone. The magnet piece 245 and the magnet piece 246 are formed by a neodymium magnet having a magnetic force of about 7000 gausses. It is conceivable that the stronger the magnetic force, the higher the ozone dissolving effect, but the magnet of at least 3000 gausses or more is desired. The reason of adoption of the magnet of 7000 gausses is its easiness in acquisition and economical efficiency. This does not intend to prevent adoption of the magnets having magnetic forces of 7000 gausses or more (natural magnets, electromagnets and the like). The connecting member 248 is formed of a member (for example, iron) with a large magnetic permeability ($\mu$) so as to suppress magnetic flux leakage and concentrate the magnetic force action on the water to be treated and the like as much as possible.

(Operational Effect of Gas-Liquid Mixing Structure)

According to the above constitution, the water to be treated which passes through the upstream side large path 232 is compressed when passing through the contracting inclined path 233, the water pressure abruptly increases, and at the same time, the passing speed abruptly rises. The peaks of high pressure and high speed occur when the water to be treated reaches the small-diameter path 234. The water to be treated which passes through the small-diameter path 234 abruptly reduces in pressure and speed in the opening inclined path 235, and receives impact or the like of the collision with the following water to be treated to be a turbulent flow. Thereafter, the water to be treated passes through the downstream side large path 236, and goes out of the gas-liquid mixing structure 205. The diffused ozone is wrapped into the turbulent flow of the water to be treated to be bubbles in various sizes large and small and subjected to a stirring action. The water to be treated (ozone) flowing in the small-diameter path 234 and at least downstream of it is subjected to the above described stirring action and a magnetic force action by the function of the magnetic circuit 243. Specifically, increase of the water pressure of the water to be treated up to the pressure peak and decrease of the pressure immediately after it reaches the pressure peak, and supply of ozone to the water to be treated which reaches the pressure peak are performed in the magnetic field. The stirring action and the magnetic force action of the magnetic field generate a synergistic effect, as a result of which, ozone dissolves in the water to be treated and high-concentration ozonized water having a high dissolution degree is produced.

(Dissolution Accelerating Tank)

Referring to FIG. 26, the dissolution accelerating tank 206 will be described. The outside of the dissolution accelerating tank 206 is constituted of a cylindrical outer wall 255 with its upper and lower ends sealed with a top plate 253 and a bottom plate 254. At an undersurface of the top plate 253, a cylindrical inner wall 256 which hangs from the undersurface is provided. A space surrounded by the inner wall 256 is the storage chamber 258 for storing the water to be treated. The outside diameter of the inner wall 256 is set to be smaller than the outside diameter of the outer wall 255, and thereby, an inter-wall passage 259 of a predetermined width is formed between the inner wall 256 and the outer wall 255. On the other hand, a lower end of the inner wall 256 does not reach the bottom plate 254, and forms a space of a predetermined width between the bottom plate 254 and itself. The space functions as a lower end communication path 257. Specifically, the storage chamber 258 surrounded by the inner wall 256 communicates with the inter-wall passage 259 via the lower end communication path 257. Meanwhile, a plurality of communication holes $256h$, $256h$, ... are penetrated through the region near the top plate 253 in the inner wall 256, and the storage chamber 258 and the inter-wall passage 259 also communicate with each other through each of the communication holes $256h$. A slim and long lifting pipe 261 is raised in a substantially center of the top surface of the bottom plate 254. A lower end of a hollow part of the lifting pipe 261 communicates with a water inlet hole $254h$ which penetrates through the bottom plate 254, and an upper end of the hollow part communicates with the storage chamber 258 through a number of small holes $261h$, ... formed in an upper end of the lifting pipe 261. The upper end of the lifting pipe 261 is located slightly below the position of the communication hole $256h$ which the inner wall 256 has. A drain port $255h$ is penetrated through the outer wall 255 in the vicinity of the position at substantially a quarter of the height of the outer wall 255 from the top in the height direction of the outer wall 255. Namely, the inter-wall passage 259 communicates with the outside via the drain port $255h$.

At a substantially center of the top plate 253, a lifting hole $253h$ is penetrated. The lifting hole $253h$ communicates with an inside of a gas-liquid separating device 265 arranged outside the top plate 253. The gas-liquid separating device 265 functions as a degassing structure for separating and discharging the water to be treated lifted up from the storage chamber 258 through the lifting hole $253h$ and ozone escaping from the water to be treated. The ozone separated by the gas-liquid separating device 265 is decomposed and rendered harmless by an ozone decomposing device 267, and thereafter, released outside the device. The ozone dissolution degree in the water to be treated is extremely high, and therefore, the amount of ozone which escapes is extremely small, but in order to enhance safety, the ozone decomposing device 267 or the like is provided. The water to be treated which is fed into the storage chamber 258 by the lifting pipe 261 is lowered by being pressed by the following water to be treated. The water to be treated which reaches the lower end turns in the lower end communication passage 257 and rises in the inter-wall passage 259, and is discharged outside through the drain port 255h. Part of the water to be treated is lifted up into the gas-liquid separating device 265. In the meantime, ozone dissolves in the water to be treated by the action of aging assimilation, and ozonized water with a high concentration is produced. On the other hand, when ozone which remains undissolved, or has temporarily dissolved but escapes is present, such ozone rises into the gas-liquid separating device 265 and is separated there. Accordingly, most of the ozone which cannot dissolve completely can be removed from the water to be treated. As a result, the ozone dissolution degree of the water to be treated which passes through the dissolution accelerating tank 206 becomes dramatically high.

(Circulation Structure)

Referring to FIG. 21, the circulation structure will be described. The circulation structure 204 has the function of circulating the water to be treated (which has already become ozonized water from raw water) which has passed through the gas-liquid mixing structure 205, and passing it through the gas-liquid mixing structure 205 again. The reason of passing the water to be treated through the gas-liquid mixing structure 205 again is to further enhance the dissolution degree and concentration of ozone by injecting ozone again into the water to be treated in which ozone has been already dissolved. The circulation structure 204 has a pump 271 as a drive source, and the storage tank 202 and the dissolution accelerating tank 206 as main components. Specifically, the pump 271 pressure-feeds the water to be treated taken out of the storage tank 202 through a pipeline 270 to the gas-liquid mixing structure 205 through a check valve 272 and a pipeline 273. The water to be treated which passes through the gas-liquid mixing structure 205 by pressure feeding passes through a pipeline 274 and the dissolution accelerating tank 206 and is returned to the storage tank 202 through a pipeline 275. The circulation structure 204 is constituted to be able to carry out the above described process repeatedly as necessary. The number of circulations can be freely set to obtain the ozone dissolution degree, the ozone concentration and the like of the ozonized water to be produced. Reference numeral 276 denotes a valve which is provided halfway in the pipeline 275. The valve 276 is provided mainly for the purpose of controlling the hydraulic pressure of the water to be treated which is passed through the small-diameter path 234 (refer to FIG. 24) of the gas-liquid mixing structure 205 by the opening and closing of it.

It is convenient to constitute the sterilizing apparatus described thus far to be movable by loading it on a moving structure such as a truck shown in FIG. 28, or a manually-operated tractor, for example. Specifically, the sterilizing apparatus can be easily conveyed to a place requiring it by the function of the moving structure. Accordingly, for example, if the sterilizing apparatus loaded on a truck (moving structure) is prepared instead of providing a large-scaled feeding line of ozonized water, a sterilizing operation can be performed by conveying the sterilizing apparatus to a place requiring it in accordance with necessity.

(Experiment 5)

Referring to FIGS. 21 and 27, an experiment 5 will be described. The experiment 5 described here is mainly for the purpose of showing that a remarkable difference occurs to the dissolution degree and concentration of ozone due to the difference between the use method of the magnets described in the Background Art and the use method of the magnets according to the present invention. In this experimental example, the ozone producing apparatus (hereinafter, referred to as "the present apparatus") shown in FIG. 21 was used as the apparatus according to the present invention, and the ozone producing apparatus (hereinafter, referred to as "the comparative apparatus") shown in FIG. 27 was used as the apparatus to be the comparison target. The comparative apparatus is allowed to include basically the same structure as the structure of the present apparatus, but is made different in only the mounting position of the magnetic circuit 243. Therefore, in FIG. 27, the same reference numerals and characters as those used in FIG. 21 are used except for the magnetic circuit, and for the magnetic circuits shown in FIG. 27, the one at the upstream side of the gas-liquid mixing structure 205 is assigned with reference numeral and character 243a, and the one at the downstream side of it is assigned with reference numeral and character 243b, respectively. In summary, the present apparatus shown in FIG. 21 includes the gas-liquid mixing structure 205 integrated with the magnetic circuit 243, and the comparative apparatus shown in FIG. 27 is constituted so as to be able to attach and detach the magnetic circuit 243a to and from the pipeline at the upstream side of the gas-liquid mixing structure 205 and the magnetic circuit 243b to and from the pipeline at the downstream side of the same simultaneously or selectively. As the gas-liquid mixing structure 205, Model 384 made by MAZZEI INJECTOR CORPORATION in U.S.A was used, and the magnetic circuits of 7000 gausses were used.

(Concentration Comparison Experiment)

Figure 30:
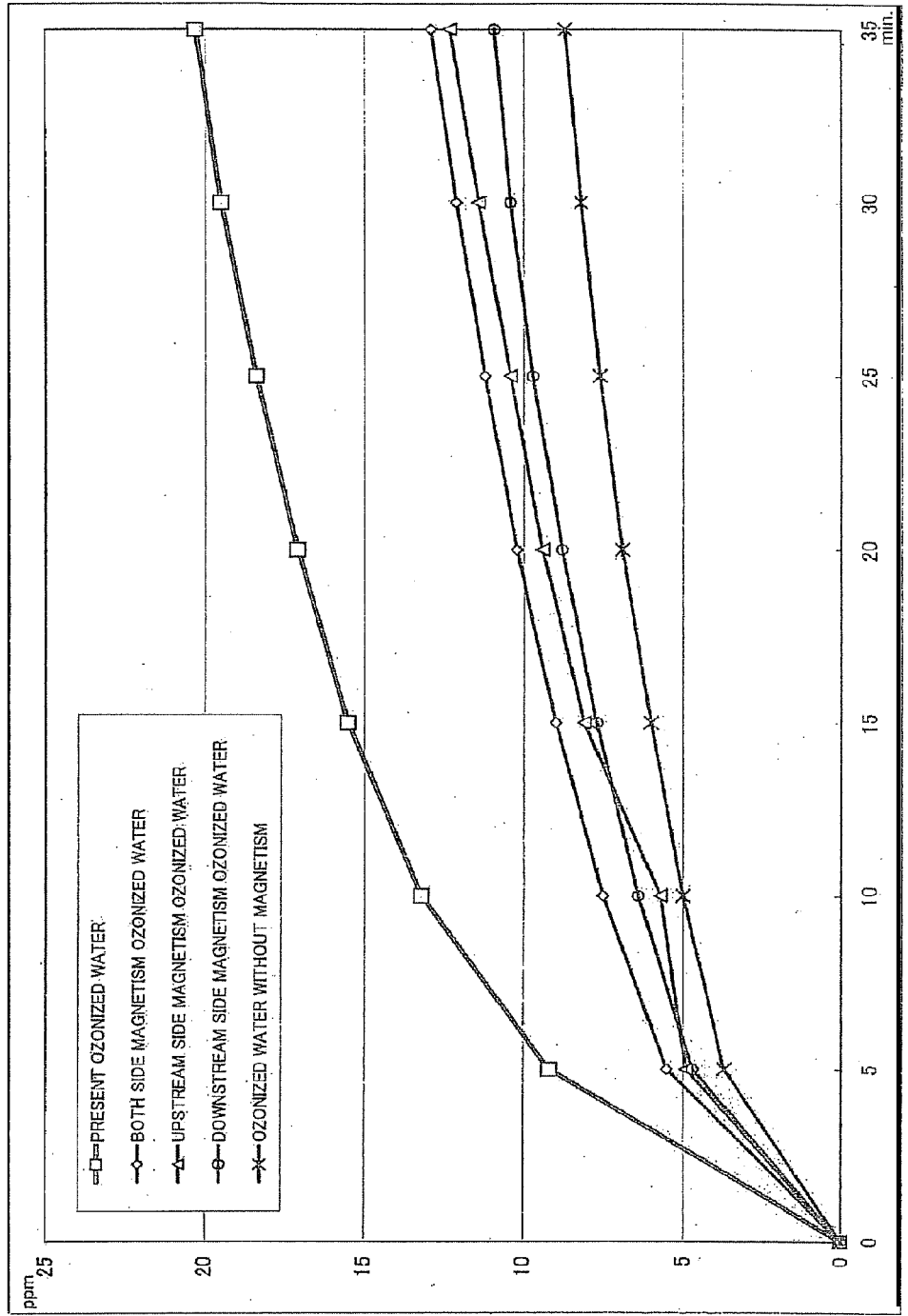
FIG. 30 is a graph showing the relationship between the ozone concentration of the ozonized water and the concentration rising time.
Figure 31:
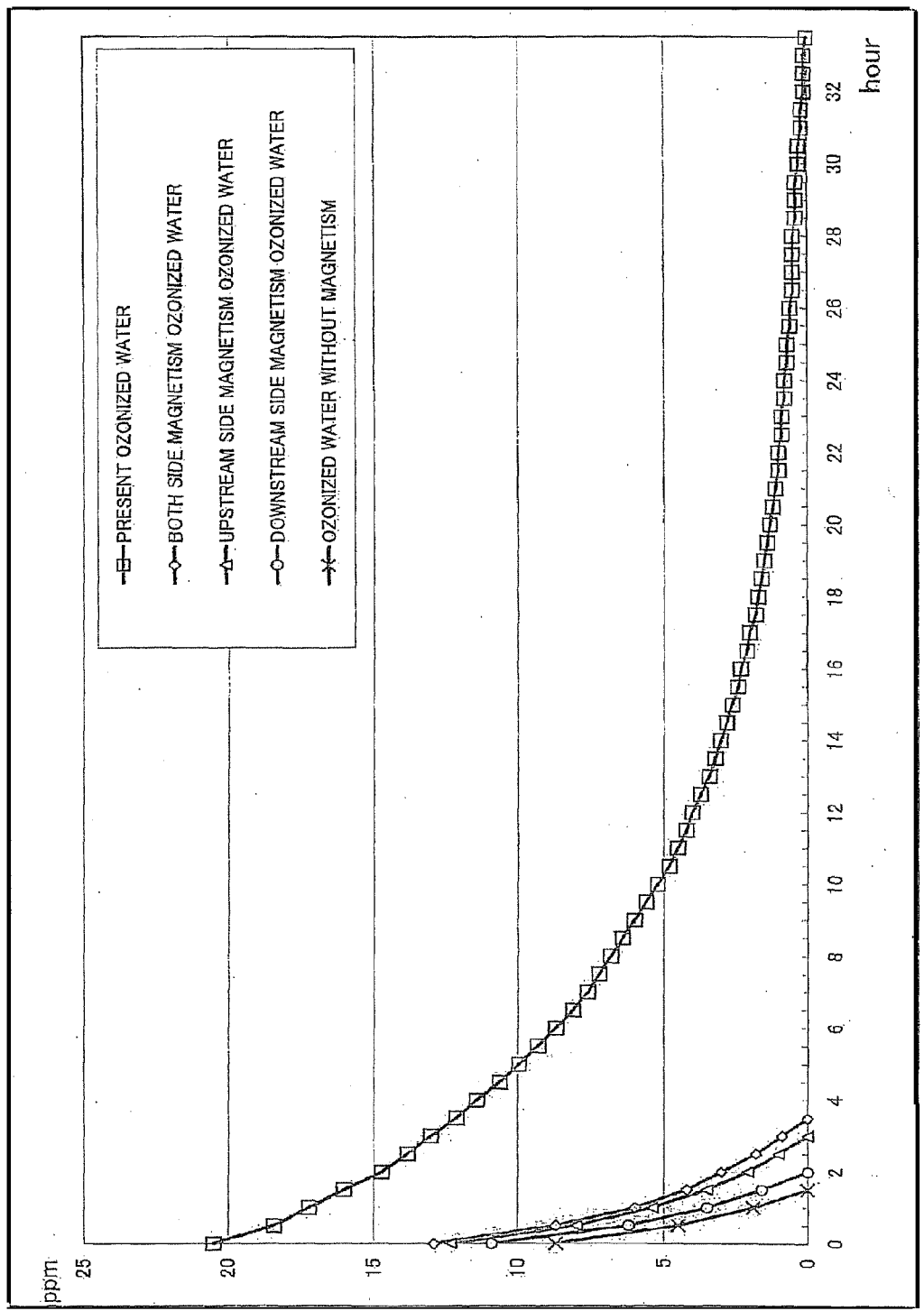
FIG. 31 is a graph showing the time required for the ozone concentration of the ozonized water in FIG. 30 to reach zero after stopping operation.

Referring to FIGS. 30 and 31, the concentration comparison experiment will be described. FIG. 30 is a graph that shows the relationship of the ozone concentration of the ozonized water and concentration rising time. FIG. 31 is a graph that shows the time required for the ozone concentration of the ozonized water shown in FIG. 30 to reach zero after stopping the operation of the producing apparatus. It shows that the longer the time before the ozone concentration reaches zero, the higher the ozone dissolution degree. In FIGS. 30 and 31, mark "□" represents the ozonized water produced by using the present apparatus (hereinafter, referred to as "present ozonized water"), mark "x" represents the ozonized water produced by using the gas-liquid mixing structure with only the magnetic circuits removed from the comparative apparatus (hereinafter, referred to as "ozonized water without magnetism"), mark "Δ" represents the ozonized water produced by the gas-liquid mixing structure 205 and the magnetic circuit 243a in the comparative apparatus (hereinafter, referred to as "upstream side magnetism ozonized water", mark "○" represents the ozonized water produced by the gas-liquid mixing structure 205 and the magnetic circuit 243b in the comparative apparatus (hereinafter, referred to as "downstream side magnetism ozonized water), and mark "◇" represents the ozonized water produced by the gas-liquid mixing structure 205 and both the magnetic circuit 243a and the magnetic circuit 243b in the comparison apparatus (hereinafter, referred to as "both side magnetism ozonized water"). The temperature of the water to be treated was 5° C., the ambient humidity was 36 to 43%, and the ambient temperature was 17° C.

As shown in FIG. 30, within 35 minutes of production time after starting the operation of the producing apparatus, the present ozonized water reached the ozone concentration of 20 ppm, whereas under the same conditions, the ozonized water without magnetism reached the ozone concentration of only about 8 ppm, the downstream side magnetism ozonized water reached the ozone concentration of only about 11 ppm, the upstream side magnetism ozonized water reached to the ozone concentration of only about 12 ppm, and the both side magnetism ozonized water reached the ozone concentration of only about 13 ppm. From this, it is firstly found out that the ozone concentration is enhanced by providing the magnetic circuit as compared with the case where it is not provided, and it is secondary found out that when comparing the case where the magnetic circuit is integrated with the gas-liquid mixing structure and the case where the magnetic circuit is provided at the spot other than the gas-liquid mixing structure, with the same magnetic circuits provided in both the cases, the ozonized water higher in concentration by at least 7 ppm can be produced in the former case than in the latter case. Specifically, the result that with respect to the ozone concentration, the present ozonized water is higher by substantially 54% ((20−13)/13×100) as compared with the both side magnetism ozonized water was obtained.

As shown in FIG. 31, while it took not less than 32 hours for the ozone concentration of the present ozonized water which reached the ozone concentration of 20 ppm to reduce to zero, it took only about 3.5 hours for the ozone concentration of the both side magnetism ozonized water to reduce to zero from 13 ppm, and this was the longest time of all the comparison target ozonized waters. Accordingly, the present ozonized water contained ozone for the time which is nearly ten times as long as that of the both side magnetism ozonized water. In other words, the present ozonized water kept the ozone, which was dissolved as a result of injecting the same amount of ozone and spending the same time period as the both side magnetism ozone water, for a time period nearly ten times as long as the time period for which the both side magnetism ozonized water kept the ozone. This plainly shows the high ozone dissolution degree of the present ozonized water.

(Ozone Bubble Particle Size Measurement Experiment)

Figure 32:
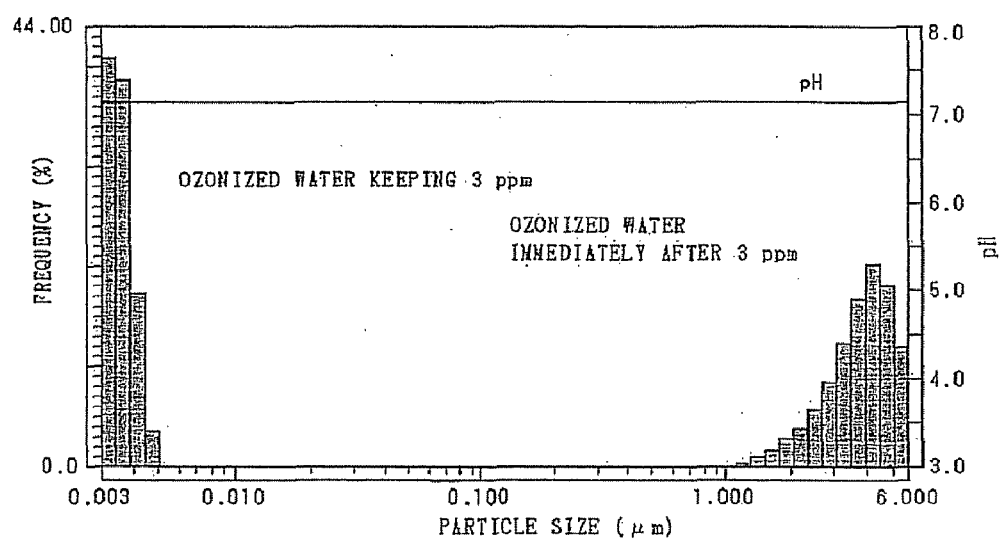
FIGS. 32 and 33 are graphs which show the particle size distribution of ozone bubbles contained in the ozonized water and pH measurement.
Figure 33:
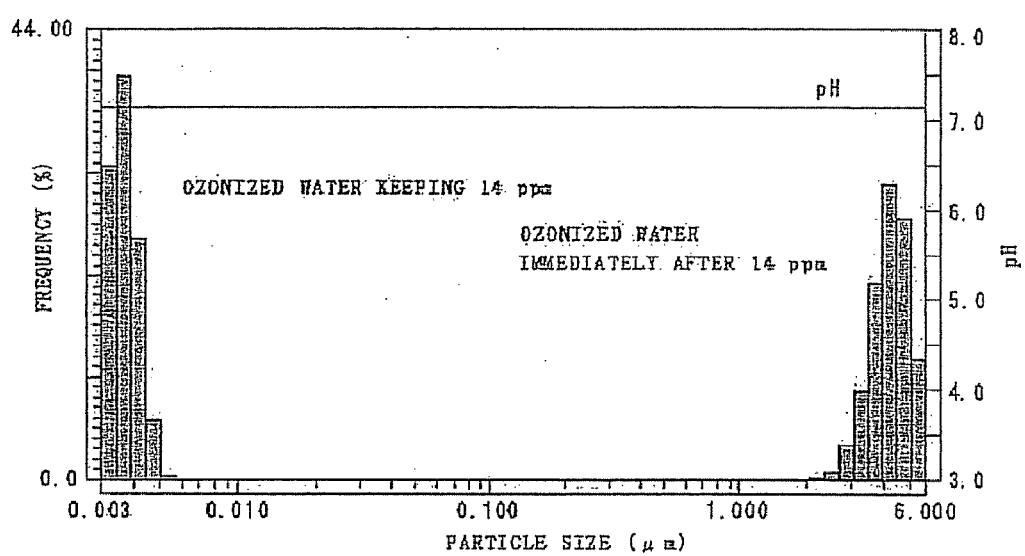

Referring to FIGS. 32 and 33, the particle size measurement experiment of the ozone bubbles contained in the present ozonized water will be described. FIGS. 32 and 33 are graphs that show the particle size distribution of the ozone bubbles contained in the present ozonized water (see the left side vertical axis). In this measurement experiment, four kinds of the present ozonized waters were set as the measurement target from the relationship of the ozone concentration and the ozone concentration keeping time. First, two kinds of ozone concentrations 3 ppm and 14 ppm were set, and next, the ozonized waters were divided into the ozonized waters immediately after reaching the respective concentrations (hereinafter, referred to as "the ozonized water immediately after 3 ppm" and "the ozonized water immediately after 14 ppm" respectively), and the ozonized waters keeping the concentrations for 15 minutes after reaching the concentrations (hereinafter, referred to as "the ozonized water keeping 3 ppm", and "the ozonized water keeping 14 ppm" respectively). Specifically, four kinds of ozonized waters, that are "the ozonized water immediately after 3 ppm", "the ozonized water keeping 3 ppm", "the ozonized water immediately after 14 ppm", and "the ozonized water keeping 14 ppm" are the measurement targets according to the measurement experiment. Here, as the raw water of the present ozonized water used in this measurement experiment, the pure water which was obtained by filtering tap water with the reverse osmosis membrane of absolute filtration of fine particle of 0.05 µm (50 nm) was used. The apparatus used for obtaining the pure water in this experiment was an ultra pure water device (model name: Model.UHP) made by SENA Co., Ltd. Since impurities of not less than 50 nm (for example, iron and magnesium) are contained in tap water, if the ozonized water which is produced from the non-filtered raw water is used as the measurement target, the impurities contained in it may be measured to cause a measurement error, and therefore, the impurities are removed by filtration in advance so that correct measurement of the bubble particle size of ozone can be made. The same thing can be said of raw water other than tap water, for example, well water and river water. The measurement instrument used for the particle size measurement of ozone bubbles was the dynamic light scattering type particle size distribution measurement instrument ((HORIBA, Ltd): model LB500). It goes without saying that if the means capable of correctly measuring the particle size of ozone bubbles without filtering impurities from raw water is available, measurement can be made by using the means.

First, based on FIG. 32, the ozonized water immediately after 3 ppm and the ozonized water keeping 3 ppm will be discussed. The graph at the right end of FIG. 32 shows the ozonized water immediately after 3 ppm, and the graph at the left end of the same shows the ozonized water keeping 0.3 ppm. It is found out that the ozonized water immediately after 3 ppm contains ozone bubbles each having a particle size of 1.3 µm (1300 nm) to 6.0 µm (6000 nm). On the other hand, it is found out that the ozonized water keeping 3 ppm contains ozone bubbles each having a particle size of 0.0034 µM (3.40 nm) to 0.0050 µm (5.00 nm).

Next, the ozonized water immediately after 14 ppm and the ozonized water keeping 14 ppm will be discussed based on FIG. 33. The graph at the right end of FIG. 33 shows the ozonized water immediately after 14 ppm, and the graph at the left end of the same shows the ozonized water keeping 14 ppm. It is found out that the ozonized water immediately after 14 ppm contains ozone bubbles each having a particle size of 2.3 µm (2300 nm) to 6.0 µm (6000 nm). On the other hand, it is found out that the ozonized water keeping 14 ppm contains ozone bubbles each having a particle size of 0.0034 µm (3.40 nm) to 0.0058 µm (5.80 nm).

The first point which has become apparent from the above described experiment is that even though the ozonized waters have the same concentration, the ozonized water immediately after reaching the concentration (immediately-after ozonized water) and the ozonized water keeping the concentration for a predetermined time (keeping ozonized water) have different particle sizes of the ozone bubbles (hereinafter, referred to as "bubble particle size" contained in them. In the case of ozonized water of 3 ppm, the minimum value of the particle size of a bubble of the immediately-after ozonized water has the value which is 260 times (1300/5.0) as large as the maximum value of the particle size of the bubble of the keeping ozonized water. Similarly, in the case of the ozonized water of 14 ppm, the minimum value of the particle size of a bubble of the immediately-after ozonized water has the value which is about 400 times (2300/5.8) as large as the maximum value of the particle size of the bubble of the keeping ozonized water. Specifically, by keeping the concentration for a predetermined time, that is, by circulating the ozonized water which is the water to be treated, the bubble particle size can be made small. The ozone bubbles with bubble particle sizes of less than 50 can be stably floated in aqueous solution. It has been found out that according to the ozonized water producing method according to the invention of the present application, the ozonized water containing ozone bubbles with the particle sizes R of less than 50 nm (0<R<50 nm), that is, the ozonized water with a high dissolution degree can be obtained. This is the second point that has become evident from the experiment. According to the experiment, the lowest actual measured value of the particle size R of the ozone bubble is 3.4 nm, and the value less than this has not been measured. The reason why such a value has not been measured is considered to be due to the limit of the measurement ability of the measuring device. Since the particle sizes R of the ozone bubbles become smaller after keeping the concentration as compared with immediately after reaching the concentration, it is easily imaginable that the ozone bubbles having the particle sizes R which are infinitely close to zero can exist in extension of reduction in particle size.

(pH Measurement Experiment)

The pH measurement experiment was conducted with respect to the above described four kinds of ozonized waters, that is, "the ozonized water immediately after 3 ppm", "the ozonized water keeping 3 ppm", "the ozonized water immediately after 14 ppm" and "the ozonized water keeping 14 ppm". The result is shown by the line graphs in FIGS. 32 and 33 (see the vertical axes at the right sides). Each ozone water showed about pH 7.3 before and after the ozone dissolution. Specifically, it has been found out that ozone dissolution hardly changes pH of the raw water. It has been found out that since well water and tap water substantially show neutrality (pH 6.5 to 7.5), the present ozonized water produced by the gas-liquid mixing method shows neutrality even if it is not doped with an additive for adjusting pH. When the raw water is alkaline, alkaline ozonized water can be produced since ozone dissolution does not change the pH of the ozonized water.

The above described experimental result will be summarized. The present ozonized water which was the target of the above described experiment is produced by gas-liquid mixture by mixing ozone into the raw water without adding any additive. Further, ozone dissolution degree is so high that ozone does not escape easily under atmospheric pressure. Therefore, the present ozonized water is safe if it is sprayed to, for example, livestock and human bodies in the respect of having no additive and no ozone escape. Since the ozone concentration can be made extremely high, an efficient cleaning and sterilizing effect and the like can be obtained by using the present ozonized water.

EXAMPLE

The effect was verified by the slaughter test on the pigs which were raised while the livestock and the pigpens were sterilized by using the above described ozonized water. The slaughter test refers to the test for determining what diseases the respiratory organs, digestive organs and the like suffered from by a veterinarian diagnosing the organs of pigs immediately after slaughter (butcher).

Ozonized water spraying in the pigpen was performed for about 20 to 90 seconds at a time, at spray intervals of 15 minutes to 2 hours inclusive in accordance with the difference in temperature due to seasonal change, characteristics of the pigs (breeding pigs, young pigs, baby pigs, and the like), the scale of the pigpen, and the like. The spraying amount was 0.3 to 0.5 litters per pigpen floor area of 3.3 m$^2$. The ozone concentration of the ozonized water was adjusted to be high so that the ozonized water in the state of at least 1 ppm reached the pig bodies, the floor surface of the pigpen or the like. The spraying angle and the average particle size of the ozonized water were adjusted so that the ozonized water spread over the pig bodies and the pigpen. Whereas the sterilizing effect of the ozonized water is as shown in the above described Table 1, the sterilizing effect of the ozonized water for the pig bodies (total number of about 3500) is as shown in Table 12, FIG. 34, and Table 13 and FIG. 35.

TABLE 12

|  | APRIL | MAY | JUNE | JULY | AUGUST | SEPTEMBER | OCTOBER | NOVEMBER |
| --- | --- | --- | --- | --- | --- | --- | --- | --- |
| RESPIRATORY SYSTEM | 85.1% | 83.3% | 78.2% | 76.0% | 74.6% | 60.2% | 56.6% | 28.6% |
| CIRCULATORY SYSTEM | 9.0% | 6.6% | 4.4% | 4.3% | 5.7% | 2.9% | 6.0% | 2.0% |
| DIGESTIVE SYSTEM | 43.1% | 42.4% | 32.6% | 29.9% | 36.0% | 20.3% | 19.3% | 16.2% |
| URINARY/GENITAL SYSTEM | 7.1% | 5.4% | 4.6% | 4.5% | 6.5% | 5.8% | 4.9% | 6.1% |
| MOTOR NERVOUS SYSTEM | 2.9% | 1.2% | 2.9% | 4.5% | 1.8% | 2.1% | 2.6% | 8.2% |

Figure 34:
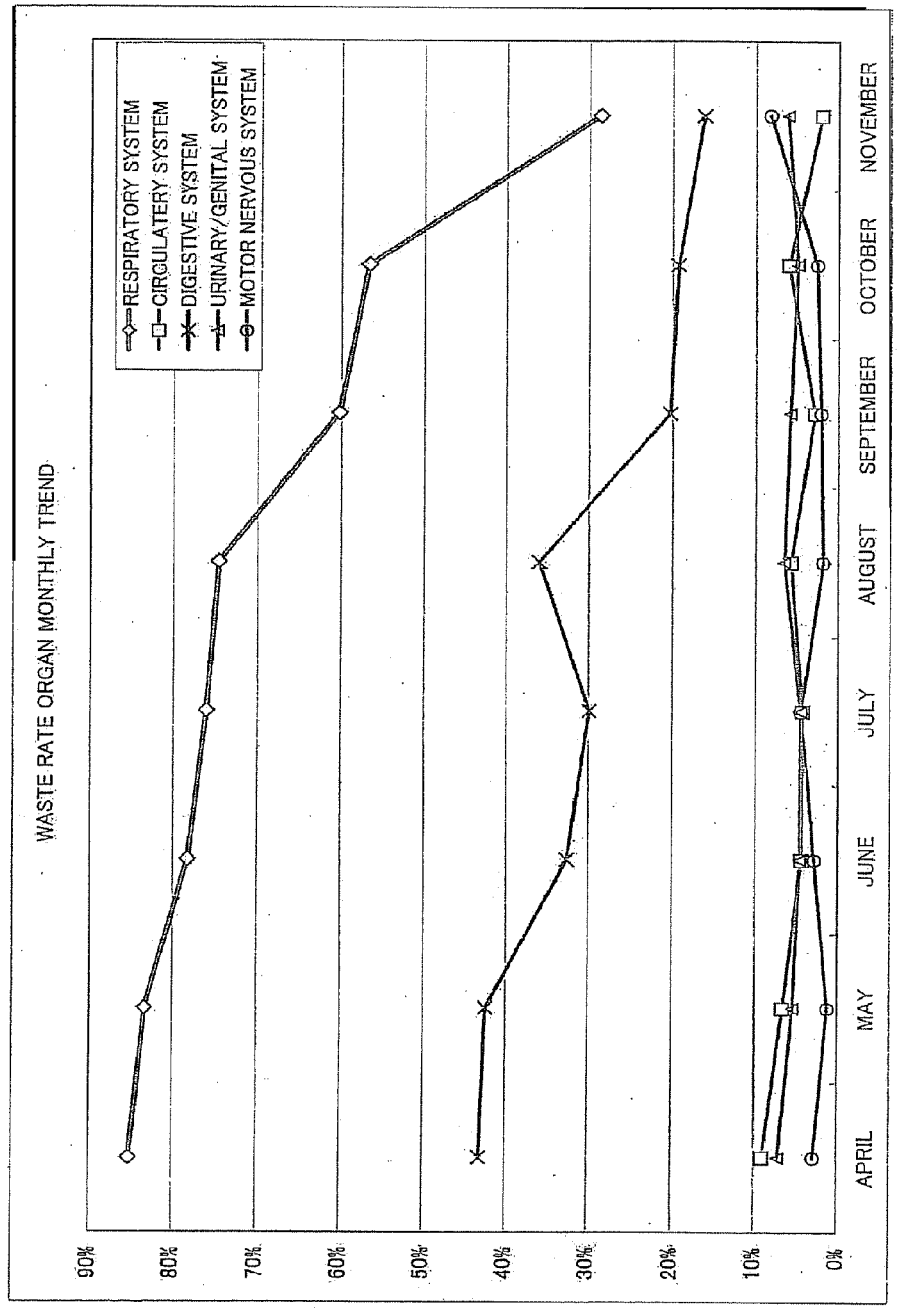
FIG. 34 is a graphic plot of the data from Table 12.

Table 12 shows the transition of the organ waste rates in five months (from April through August) before the introduction of the ozonized water sterilizing, and in three months (from September through November) after the introduction in accordance with the kinds of the organ systems. FIG. 34 is a graphic plot of the numerical values in Table 12. The organ waste rates of the organs of the circulatory system, urinary/genital system and the motor nervous system were substantially less than 10% regardless of before and after the introduction. On the other hand, the organ waste rate of the respiratory system which gradually reduced from April through August before the introduction was 74.6% in August, and abruptly reduced to 60.2% in September when the ozonized water sterilizing was introduced (reduction by 14.4%). Thereafter, the waste rate reduced to only 56.6% which was the reduction by several percent in October, but in November, it abruptly reduced to 28.6%. As compared with 74.6% before the introduction of the ozonized water sterilizing, the waste rate reduced to about a half (reduction by 46%) in three months. This is supposed to be the result that by spraying the ozonized water pathogenic bacteria, viruses and the like attached to powder dust of excrement and residual food floating in the pigpen were sterilized by the ozonized water and this prevented the infection of the respiratory systems.

On the other hand, the waste rate of the digestive organs was 36.0% in August before the introduction, but reduced to 20.3% in September, one month after the introduction (reduction by 15.7%). Thereafter, the waste rate did not change so much and was 19.3% in October, which was the reduction by only 1%, but it reduced to 16.2% in November. Accordingly, as compared with 36.0% before the introduction of the ozonized water sterilizing, the waste rate also reduced to substantially a half in three months. It is supposed to be the result that contamination of the food of the pigs with viruses was significantly reduced.

TABLE 13

|  | APRIL THROUGH AUGUST BEFORE INTRODUCTION | SEPTEMBER AFTER INTRODUCTION | OCTOBER AFTER INTRODUCTION | NOVEMBER AFTER INTRODUCTION |
| --- | --- | --- | --- | --- |
| SEP | 14.0% | 10.8% | 10.5% | 4.1% |
| PNEUMONIA | 37.1% | 15.8% | 24.7% | 10.2% |
| PLEURISY | 29.1% | 33.6% | 18.4% | 14.3% |
| HEPATITIS (PARASITE) | 1.9% | 0.4% | 2.2% | 0.0% |
| ENTERITIS | 9.7% | 1.2% | 5.2% | 2.0% |

Figure 35:
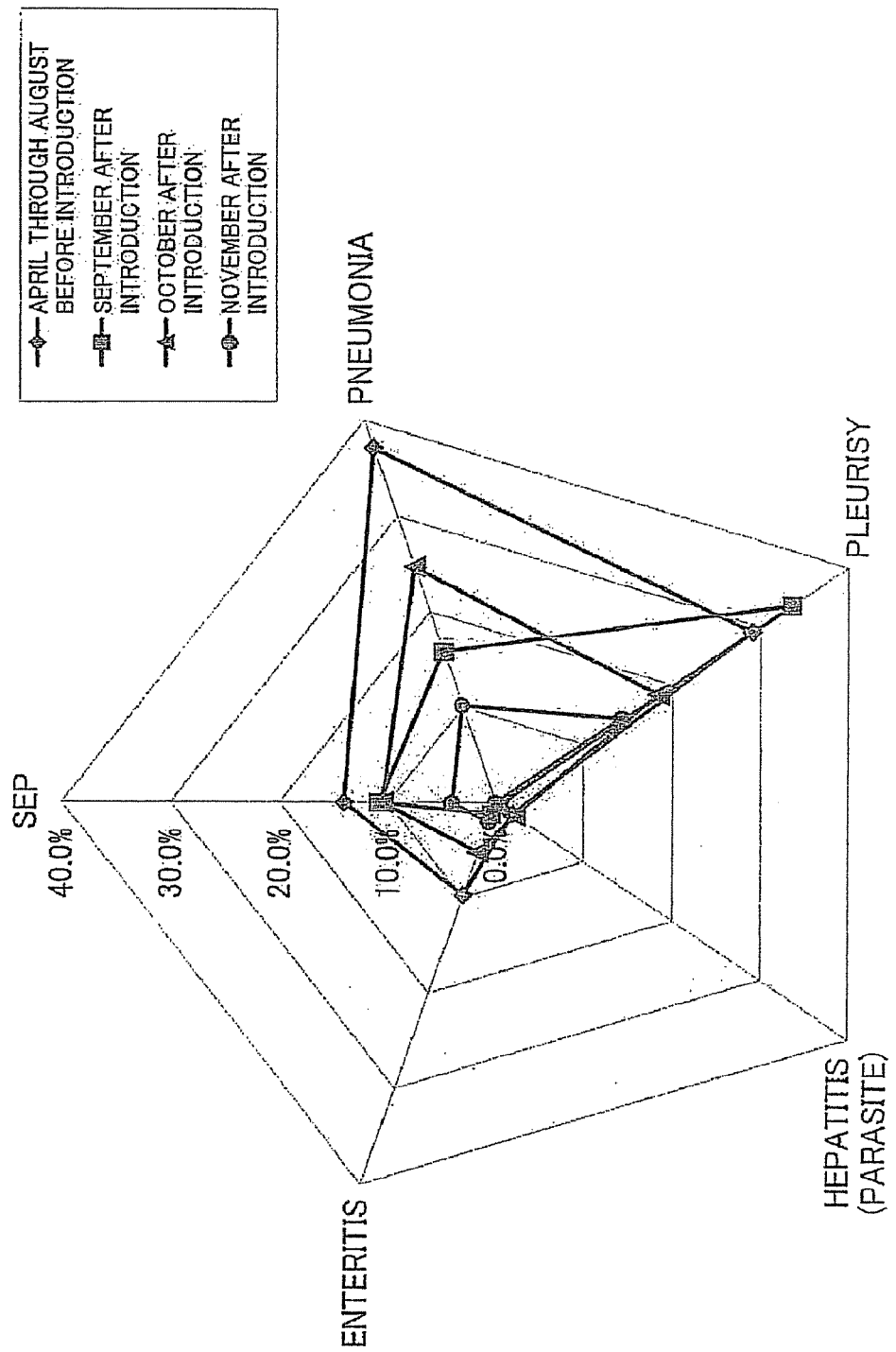
FIG. 35 is a coordinate graph showing the data in Table 13.

Table 13 shows the comparison of the transitions of incidence rates of SEP, pneumonia, pleurisy, hepatitis (parasite) and enteritis before and after the introduction of the ozonized water sterilizing. The coordinate graph shown in FIG. 35 is a graphic plot of the numerical values of Table 13. The incidence rate of SEP which was 14.1% before the introduction reduced to 4.1% in November three months after the introduction. It reduced to substantially one third. The incidence rate of pneumonia which was 37.1% before the introduction reduced to 10.2% in November, three months after the introduction. It reduced to substantially one fourth. The incidence rate of pleurisy reduced to 14.3% from 29.1% which was substantially a half. The incidence rate of hepatitis which was 1.9% before the introduction reduced to 0.4% one month after the introduction, but increased to 2.2% two months after the introduction. However, it became 0% three months after the introduction. The incidence rate of enteritis abruptly reduced to 1.2% one month after the introduction from 9.7% before the introduction, but also increased to 5.2% two months after the introduction. However, it reduced to 2.0% three months after the introduction.

As described above, it has been found that the sterilizing effect by introduction of the ozonized water sterilizing significantly reduces the organ waste rate and the disease incidence rate of the pig bodies. Specifically, adoption of the raising method of raising pigs while performing ozonized water sterilizing is effective in keeping pig bodies (livestock) healthy and provides hygienic and safe pork (livestock meat). Further, the above described embodiment relates to the pigs and pigpens, but since ozonized water is safe to man and livestock, the present invention seems to be effective for livestock other than pigs (for example, chickens and cows). The reason of performing ozonized water sterilizing is to clean the environment by reducing bacteria and viruses since a large amount of such bacteria and viruses which are the targets of the ozonized water sterilizing exist on the surfaces of the livestock, the livestock barns and the like and the atmosphere around them. This point is already described. Further, it has been found out that the ozonized water described thus far is useful as an antiseptic solution for effectively sterilizing livestock, the raising facility and the like by inactivating viruses and the like. Further, such ozonized water is suitable for inactivating viruses and the like attached to the facilities, instruments and the like for producing vaccines to be given to human bodies, livestock and the like. Animals such as guinea pigs to be used for producing vaccines may be raised in some cases.

Specifically, attenuated viruses, dead viruses and the like used for vaccine production are attached to the above described facilities, instruments, animals and the like, and float in the air in and around them in many cases. In order to inactivate such attenuated viruses, formalin is used at present. However, if formalin remains in the facilities, instruments and the like, there arises the fear of injuring the manufacturing workers and the like. Inactivation by using the ozonized water eliminates such a fear. On the other hand, the workers engaged in raising and sterilizing livestock and the like, persons and the like coming in and approaching the livestock and the livestock barns for some reason are exposed to the above described bacteria and viruses. Such bacteria and viruses include the bacteria and viruses which are highly likely to infect human beings such as Avian influenza virus, Nipah virus, Severe Acute Respiratory Syndrome (SARS). Accordingly, the above described infection can be effectively prevented by using the ozonized water (especially, neutral ozonized water) which is described thus far for human bodies (especially, hands, faces and legs) and members which contact and accompany the human bodies in relation with the livestock and livestock barns (for example, clothing such as working wear, working gloves, foot wear such as boots, cleaning tools such as brushes, containers for putting food in, scoops). When workers after working actually cleaned their hands and faces with neutral ozonized water continuously, it has been confirmed that the neutral ozonized water was able to keep the health condition of the skin favorable as an effective antiseptic solution for human bodies, and was usable as a so-called cosmetic liquid (lotion) which has a remarkable cosmetic effect.

EXPLANATION OF REFERENCE NUMBERS USED IN THE DRAWINGS

1 STERILIZING APPARATUS
1A STERILIZING APPARATUS
2 CONTROL DEVICE (CONTROLLER)
3 Water Intake Valve
4 PIPELINE
5 OZONIZED WATER PRODUCING APPARATUS
7 PRESSURE PUMP
9 NOZZLE (NOZZLE GROUP)
11 Raw Water Fragmenting Structure
11a CASING
11b PACKING
11c MAGNET (CARBON CHIP GROUP, ULTRASONIC WAVE GENERATING DEVICE)
13 Ozone Dissolving Structure
15 STORAGE TANK
16 PIPELINE
17 PIPELINE
19 OZONE SUPPLY STRUCTURE (OZONE SUPPLY DEVICE)
20 PIPELINE
21 CIRCULATION STRUCTURE
22 CHECK-VALVE
23 VALVE
31 FIRST VORTEX FLOW PUMP
31' SECOND VORTEX FLOW PUMP
31'A VORTEX FLOW PUMP 32 Pump Main Body
32a INTAKE PART
32b DISCHARGE PART
32d PRESSURE RAISING PASSAGE
32e INTAKE PATH
32f DISCHARGE PATH
32m MAGNET
33 IMPELLER
33a IMPELLER MAIN BODY
33b BLADE PIECE
33c BLADE GROOVE
33d ROTARY SHAFT
34 OZONE RETURN PART
34a RETURN PATH
35 EJECTOR
35A EJECTOR
36 VENTURI TUBE
36a INLET PATH
36b OUTLET PATH
36c SMALL-DIAMETER PATH
36m MAGNET
37 OZONE SUPPLY PIPE
37a SUPPLY PATH
38 SMALL-DIAMETER PATH
41 STATIC MIXER
41a STREAM TUBE
41b BAFFLE BOARD GROUP
42 PIPELINE
46 PIPELINE
51 STATIC MIXER
52 PIPELINE
55 CYCLONE
56 CYCLONE MAIN BODY
56a UPPER SPACE
57 GAS-LIQUID SEPARATING DEVICE
61 OZONIZED WATER RETURN PIPE
63 TEMPERATURE KEEPING DEVICE
65 OZONE RETURN PIPE
70 PIPELINE
71 CHECK-VALVE
101 PIGPEN
103 WATER SUPPLY LINE
104 ELECTROMAGNETIC VALVE
104a ELECTROMAGNETIC VALVE
104b ELECTROMAGNETIC VALVE
105 SPRAY LINE
107 RETURN LINE
107V LINE VALVE
109 FILTER
121 FLUID SENSOR
123 PRESSURE SENSOR
150 CAGE
153 NOZZLE
155 STERILIZING PASSAGE
157 NOZZLE (NOZZLE GROUP)
159 NOZZLE (NOZZLE GROUP)
161 BLOW DEVICE
163 AIR
165 VENTILATION FAN
201 OZONE WATER PRODUCING APPARATUS
202 STORAGE TANK
203 OZONE SUPPLY STRUCTURE
204 CIRCULATION STRUCTURE
205 GAS-LIQUID MIXING STRUCTURE
206 DISSOLUTION ACCELERATING TANK
207 TEMPERATURE KEEPING STRUCTURE
231 VENTURI TUBE
232 UPSTREAM SIDE LARGE-DIAMETER PATH
233 CONSTRICTING INCLINED PATH
234 SMALL-DIAMETER PATH
235 OPENING INCLINED PATH
236 DOWNSTREAM SIDE LARGE-DIAMETER PATH
239 OZONE SUPPLY PIPE
243 MAGNETIC CIRCUIT
245 ONE MAGNET PIECE
246 OTHER MAGNET PIECE
265 GAS-LIQUID SEPARATING DEVICE
267 OZONE DECOMPOSING DEVICE

The invention claimed is:

1. A livestock sterilizing method, comprising:
an ozonized water producing step of producing ozonized water with a particle size R of a contained ozone bubble satisfying 0 nm<R<50 nm, an ozone concentration of 3 ppm to 20 ppm, and a pH of 6.5 to 7.5, by a gas-liquid mixing method; and
a step of sterilizing livestock by using the ozonized water produced in the ozonized water producing step, whereby ozone escape from said ozonized water is substantially inhibited.

2. The livestock sterilizing method according to claim 1, wherein said ozonized water producing step causes a magnetic force to act on water to be treated and ozone when mixing the ozone into the water to be treated.

3. The livestock sterilizing method according to claim 2, wherein in a magnetic field, hydraulic pressure of the water to be treated is increased until it reaches a pressure peak, and is reduced immediately after it reaches the pressure peak, and ozone is supplied to the water to be treated which reaches the pressure peak.

4. The livestock sterilizing method according to claim 3, wherein the water to be treated is passed through a Venturi tube having a small-diameter path, and ozone is supplied through an ozone supply pipe having an open end disposed at a position facing the small-diameter path, and wherein a magnetic force is caused to act on at least one of the small-diameter path and/or a vicinity of the small-diameter path of the Venturi tube.

5. The livestock sterilizing method according to claim 4, wherein the water to be treated which has passed said Venturi tube is circulated, and is caused to pass through said Venturi tube at least once again while ozone is being supplied.

6. The livestock sterilizing method according to claim 5, wherein said circulated water to be treated is temporarily stored in a storage tank.

7. The livestock sterilizing method according to claim 6, wherein the water to be treated stored in said storage tank is temporarily taken out and kept at a temperature in a range of 5° C. to 15° C.

8. The livestock sterilizing method according to claim 5, wherein the water to be treated after ozone is mixed therein is temporarily stored in a dissolution accelerating tank to accelerate ozone dissolution.

9. The livestock sterilizing method according to claim 8, wherein ozone escaping from the water to be treated which is stored in said dissolution accelerating tank is discharged to an outside of the dissolution accelerating tank.

10. The livestock sterilizing method according to claim 1, wherein at least one of livestock facility and/or a livestock tool are/is sterilized at a same time by using the ozonized water for sterilizing the livestock.

11. A livestock sterilizing method, comprising:
an ozonized water producing step of producing ozonized water with a particle size R of a contained ozone bubble satisfying 0 nm<R<50 nm and an ozone concentration of 3 ppm to 20 ppm by a gas-liquid mixing method;

a step of controlling a temperature of the ozonized water in a range of 5° C. to 15° C.; and a step of sterilizing livestock by using the ozonized water produced in the ozonized water producing step, whereby ozone escape from said ozonized water is substantially inhibited.

12. The livestock sterilizing method according to claim 11, wherein said ozonized water producing step causes a magnetic force to act on water to be treated and ozone when mixing the ozone into the water to be treated.

13. The livestock sterilizing method according to claim 12, wherein in a magnetic field, hydraulic pressure of the water to be treated is increased until it reaches a pressure peak, and is reduced immediately after it reaches the pressure peak, and ozone is supplied to the water to be treated which reaches the pressure peak.

14. The livestock sterilizing method according to claim 13, wherein the water to be treated is passed through a Venturi tube having a small-diameter path, and ozone is supplied through an ozone supply pipe having an open end disposed at a position facing the small-diameter path, and wherein a magnetic force is caused to act on at least one of the small-diameter path and/or a vicinity of the small-diameter path of the Venturi tube.

15. The livestock sterilizing method according to claim 14, wherein the water to be treated which has passed said Venturi tube is circulated, and is caused to pass through said Venturi tube at least once again while ozone is being supplied.

16. The livestock sterilizing method according to claim 15, wherein said circulated water to be treated is temporarily stored in a storage tank.

17. The livestock sterilizing method according to claim 16, wherein the water to be treated stored in said storage tank is temporarily taken out and kept at a temperature in a range of 5° C. to 15° C.

18. The livestock sterilizing method according to claim 15, wherein the water to be treated after ozone is mixed therein is temporarily stored in a dissolution accelerating tank to accelerate ozone dissolution.

19. The livestock sterilizing method according to claim 18, wherein ozone escaping from the water to be treated which is stored in said dissolution accelerating tank is discharged to an outside of the dissolution accelerating tank.

20. The livestock sterilizing method according to claim 11, wherein at least one of livestock facility and/or a livestock tool are/is sterilized at a same time by using the ozonized water for sterilizing the livestock.

21. A livestock sterilizing method, comprising:

an ozonized water producing step of producing ozonized water with a particle size R of a contained ozone bubble satisfying 0 nm<R<50 nm, an ozone concentration of 3 ppm to 20 ppm, and a pH of 6.5 to 7.5, by a gas-liquid mixing method;

a step of controlling a temperature of the ozonized water in a range of 5° C. to 15° C.; and a step of sterilizing livestock by using the ozonized water produced in the ozonized water producing step, whereby ozone escape from said ozonized water is substantially inhibited.

22. The livestock sterilizing method according to claim 21, wherein said ozonized water producing step causes a magnetic force to act on water to be treated and ozone when mixing the ozone into the water to be treated.

23. The livestock sterilizing method according to claim 22, wherein in a magnetic field, hydraulic pressure of the water to be treated is increased until it reaches a pressure peak, and is reduced immediately after it reaches the pressure peak, and ozone is supplied to the water to be treated which reaches the pressure peak.

24. The livestock sterilizing method according to claim 23, wherein the water to be treated is passed through a Venturi tube having a small-diameter path, and ozone is supplied through an ozone supply pipe having an open end disposed at a position facing the small-diameter path, and wherein a magnetic force is caused to act on at least one of the small-diameter path and/or a vicinity of the small-diameter path of the Venturi tube.

25. The livestock sterilizing method according to claim 24, wherein the water to be treated which has passed said Venturi tube is circulated, and is caused to pass through said Venturi tube at least once again while ozone is being supplied.

26. The livestock sterilizing method according to claim 25, wherein said circulated water to be treated is temporarily stored in a storage tank.

27. The livestock sterilizing method according to claim 26, wherein the water to be treated stored in said storage tank is temporarily taken out and kept at a temperature in a range of 5° C. to 15° C.

28. The livestock sterilizing method according to claim 25, wherein the water to be treated after ozone is mixed therein is temporarily stored in a dissolution accelerating tank to accelerate ozone dissolution.

29. The livestock sterilizing method according to claim 28, wherein ozone escaping from the water to be treated which is stored in said dissolution accelerating tank is discharged to an outside of the dissolution accelerating tank.

30. The livestock sterilizing method according to claim 21, wherein a livestock facility and/or a livestock tool are/is sterilized at a same time by using the ozonized water for sterilizing the livestock.

31. A livestock sterilizing method, comprising:

an ozonized water producing step of producing ozonized water with a particle size R of a contained ozone bubble satisfying 0 nm<R<50 nm, an ozone concentration of 3 ppm to 20 ppm, and a pH of 6.5 to 7.5, by a gas-liquid mixing method; and a step of sterilizing livestock by using the ozonized water produced in the ozonized water producing step;

said step of sterilizing livestock including a step of pressurizing the ozonized water produced in the ozonized water producing step to predetermined pressure and spraying the pressurized ozonized water from a nozzle or a nozzle group to pour it on livestock so that ozone escaping from said ozonized water is substantially inhibited.

32. The livestock sterilizing method according to claim 31, wherein the predetermined pressure of the ozonized water at a time of pressurizing and spraying said ozonized water is 0.2 MPa to 0.8 MPa.

33. The livestock sterilizing method according to claim 32, wherein an average particle size of the ozonized water which is sprayed in said spraying step is 40 mm to below 200 mm or 200 mm to 1000 mm.

34. The livestock sterilizing method according to claim 31, further comprising a step of returning residual ozonized water, which is not sprayed in said spraying step and remains, into said storage tank by pressure feeding.

35. The livestock sterilizing method according to claim 34, further comprising:

a step of performing ozonized water spraying after returning the residual ozonized water which is outside said storage tank to said storage tank before start of the ozonized water spraying, when starting the ozonized water spraying again after temporarily stopping the ozonized water spraying in said spraying step.

36. The livestock sterilizing method according to claim 31, wherein said spraying step includes a step of directly spraying the ozonized water to a pubic region of livestock.

37. The livestock sterilizing method according to claim 31, wherein said spraying step includes a step of spraying said ozonized water from a position higher than and a position lower than the livestock while letting the livestock move in a column, and a step of performing dewatering by air blow after finishing the ozonized water spraying.

38. The livestock sterilizing method according to claim 37, wherein said air blow is performed for livestock at an angle of 20 degrees to 70 degrees with respect to horizontality from above a front with respect to the livestock.

39. The livestock sterilizing method according to claim 31, wherein at least one of livestock facility and/or a livestock tool are/is sterilized at a same time by using the ozonized water for sterilizing the livestock.

40. A livestock sterilizing method, comprising:
an ozonized water producing step of producing ozonized water with a particle size R of a contained ozone bubble satisfying 0 nm<R<50 nm and an ozone concentration of 3 ppm to 20 ppm by a gas-liquid mixing method;
a step of controlling a temperature of the ozonized water in a range of 5° C. to 15° C.; and
a step of sterilizing livestock by using the ozonized water produced in the ozonized water producing step;
said step of sterilizing livestock including
a step of pressurizing the ozonized water produced in the ozonized water producing step to predetermined pressure and spraying the pressurized ozonized water from a nozzle or a nozzle group to pour it on livestock so that ozone escaping from said ozonized water is substantially inhibited.

41. The livestock sterilizing method according to claim 40, wherein the predetermined pressure of the ozonized water at a time of pressurizing and spraying said ozonized water is 0.2 MPa to 0.8 MPa.

42. The livestock sterilizing method according to claim 41, wherein an average particle size of the ozonized water which is sprayed in said spraying step is 40 mm to below 200 mm or 200 mm to 1000 mm.

43. The livestock sterilizing method according to claim 40, further comprising a step of returning residual ozonized water, which is not sprayed in said spraying step and remains, into said storage tank by pressure feeding.

44. The livestock sterilizing method according to claim 43, further comprising:
a step of performing ozonized water spraying after returning the residual ozonized water which is outside said storage tank to said storage tank before start of the ozonized water spraying, when starting the ozonized water spraying again after temporarily stopping the ozonized water spraying in said spraying step.

45. The livestock sterilizing method according to claim 40, wherein said spraying step includes a step of directly spraying the ozonized water to a pubic region of livestock.

46. The livestock sterilizing method according to claim 40, wherein said spraying step includes a step of spraying said ozonized water from a position higher than and a position lower than the livestock while letting the livestock move in a column, and a step of performing dewatering by air blow after finishing the ozonized water spraying.

47. The livestock sterilizing method according to claim 46, wherein said air blow is performed for livestock at an angle of 20 degrees to 70 degrees with respect to horizontality from above a front with respect to the livestock.

48. The livestock sterilizing method according to claim 40, wherein at least one of livestock facility and/or a livestock tool are/is sterilized at a same time by using the ozonized water for sterilizing the livestock.

49. A livestock sterilizing method, comprising:
an ozonized water producing step of producing ozonized water with a particle size R of a contained ozone bubble satisfying 0 nm<R<50 nm, an ozone concentration of 3 ppm to 20 ppm, and a pH of 6.5 to 7.5, by a gas-liquid mixing method;
a step of controlling a temperature of the ozonized water in a range of 5° C. to 15° C.; and
a step of sterilizing livestock by using the ozonized water produced in the ozonized water producing step;
said step of sterilizing livestock including
a step of pressurizing the ozonized water produced in the ozonized water producing step to predetermined pressure and spraying the pressurized ozonized water from a nozzle or a nozzle group to pour it on livestock so that ozone escaping from said ozonized water is substantially inhibited.

50. The livestock sterilizing method according to claim 49, wherein the predetermined pressure of the ozonized water at a time of pressurizing and spraying said ozonized water is 0.2 MPa to 0.8 MPa.

51. The livestock sterilizing method according to claim 50, wherein an average particle size of the ozonized water which is sprayed in said spraying step is 40 mm to below 200 mm or 200 mm to 1000 mm.

52. The livestock sterilizing method according to claim 49, further comprising:
a step of returning residual ozonized water, which is not sprayed in said spraying step and remains, into said storage tank by pressure feeding.

53. The livestock sterilizing method according to claim 52, further comprising:
a step of performing ozonized water spraying after returning the residual ozonized water which is outside said storage tank to said storage tank before start of the ozonized water spraying, when starting the ozonized water spraying again after temporarily stopping the ozonized water spraying in said spraying step.

54. The livestock sterilizing method according to claim 49, wherein said spraying step includes a step of directly spraying the ozonized water to a pubic region of livestock.

55. The livestock sterilizing method according to claim 49, wherein said spraying step includes a step of spraying said ozonized water from a position higher than and a position lower than the livestock while letting the livestock move in a column, and a step of performing dewatering by air blow after finishing the ozonized water spraying.

56. The livestock sterilizing method according to claim 55, wherein said air blow is performed for livestock at an angle of 20 degrees to 70 degrees with respect to horizontality from above a front with respect to the livestock.

57. The livestock sterilizing method according to claim 49, wherein at least one of livestock facility and/or a livestock tool are/is sterilized at a same time by using the ozonized water for sterilizing the livestock.

* * * * *